US011116499B1

(12) United States Patent
Blair et al.

(10) Patent No.: US 11,116,499 B1
(45) Date of Patent: Sep. 14, 2021

(54) LOW PROFILE STAPLE AND METHODS FOR USING THE SAME

(71) Applicant: MedShape, Inc., Atlanta, GA (US)

(72) Inventors: Jeremy Webster Blair, Atlanta, GA (US); Courtney Lynne Kline, Atlanta, GA (US)

(73) Assignee: MEDSHAPE, INC., Atlanta, GA (US)

( * ) Notice: Subject to any disclaimer, the term of this patent is extended or adjusted under 35 U.S.C. 154(b) by 0 days.

(21) Appl. No.: 17/004,789

(22) Filed: Aug. 27, 2020

Related U.S. Application Data

(63) Continuation-in-part of application No. 16/393,489, filed on Apr. 24, 2019, which is a continuation of application No. 16/058,638, filed on Aug. 8, 2018, now Pat. No. 10,307,156, and a continuation-in-part of application No. 29/659,375, filed on Aug. 8, 2018, now Pat. No. Des. 895,113.

(51) Int. Cl.
*A61B 17/064* (2006.01)
*A61B 17/00* (2006.01)

(52) U.S. Cl.
CPC ...... *A61B 17/0642* (2013.01); *A61B 17/0644* (2013.01); *A61B 2017/00867* (2013.01); *A61B 2017/0645* (2013.01)

(58) Field of Classification Search
CPC .............. A61B 17/064; A61B 17/0642; A61B 17/0644
USPC ........................................... 606/75; 227/902
See application file for complete search history.

(56) References Cited

U.S. PATENT DOCUMENTS

| 2,632,356 | A | 3/1953 | Thiel |
| D227,976 | S | 7/1973 | Gerald |
| D281,814 | S | 12/1985 | Pratt |
| 5,662,655 | A | 9/1997 | Laboureau et al. |
| 6,187,009 | B1 | 2/2001 | Herzog et al. |
| D586,915 | S | 2/2009 | Grim et al. |
| 7,722,610 | B2 | 5/2010 | Viola et al. |
| D625,591 | S | 10/2010 | MacDonald et al. |
| 9,402,624 | B1 | 8/2016 | Scott et al. |
| D773,665 | S | 12/2016 | Cheney et al. |
| 9,675,395 | B2 | 6/2017 | Averous et al. |
| D804,666 | S | 12/2017 | Guo et al. |
| 10,117,647 | B2 * | 11/2018 | Cheney ............... A61B 17/0642 |
| 10,307,156 | B1 * | 6/2019 | Blair .................... A61B 17/0642 |
| D857,199 | S | 8/2019 | Cheney et al. |
| D870,284 | S | 12/2019 | Hollis et al. |
| 10,568,627 | B2 | 2/2020 | Guo et al. |
| 10,610,218 | B2 | 4/2020 | Palmer et al. |
| 2006/0058802 | A1 * | 3/2006 | Kofoed ................ A61B 17/562 606/75 |
| 2008/0161808 | A1 * | 7/2008 | Fox ..................... A61B 17/0642 606/75 |
| 2008/0167666 | A1 | 7/2008 | Fiere |
| 2008/0319443 | A1 * | 12/2008 | Focht ................. A61B 17/0642 606/75 |

(Continued)

*Primary Examiner* — Eric S Gibson
(74) *Attorney, Agent, or Firm* — Morris, Manning & Martin, LLP; Bryan D. Stewart

(57) ABSTRACT

According to particular embodiments, the present staple includes a low-profile bridge and has the capacity for high sustained compression. In some embodiments, the staple includes a bridge with a continuous cross-section, and one or more pairs of legs with teeth cut therein, the inner legs and outer legs each including an angle of about 16 degrees.

20 Claims, 46 Drawing Sheets

(56) References Cited

U.S. PATENT DOCUMENTS

| | | | |
|---|---|---|---|
| 2010/0063506 A1* | 3/2010 | Fox | A61F 2/28 606/75 |
| 2011/0118842 A1 | 5/2011 | Bernard | |
| 2013/0123863 A1* | 5/2013 | Hollis | A61B 17/0642 606/328 |
| 2013/0231667 A1* | 9/2013 | Taylor | A61B 17/0642 606/75 |
| 2013/0267956 A1* | 10/2013 | Terrill | A61B 17/0642 606/75 |
| 2014/0018809 A1* | 1/2014 | Allen | A61B 17/8004 606/75 |
| 2014/0097228 A1 | 4/2014 | Taylor | |
| 2014/0277516 A1 | 9/2014 | Miller | |
| 2014/0358187 A1 | 12/2014 | Taber | |
| 2015/0133940 A1* | 5/2015 | Palmer | A61B 17/7266 606/75 |
| 2015/0313592 A1* | 11/2015 | Coillard-Lavirotte | A61B 17/0642 606/75 |
| 2016/0000434 A1* | 1/2016 | Cocaign | A61B 17/0684 606/75 |
| 2016/0030039 A1* | 2/2016 | Seavey | A61B 17/16 206/210 |
| 2016/0066907 A1* | 3/2016 | Cheney | A61B 17/0684 606/75 |
| 2016/0135808 A1* | 5/2016 | Anderson | A61B 17/0644 606/219 |
| 2016/0199060 A1* | 7/2016 | Morgan | A61B 17/068 227/175.1 |
| 2016/0235460 A1 | 8/2016 | Wahl | |
| 2016/0338697 A1* | 11/2016 | Biedermann | A61B 17/064 |
| 2017/0065275 A1* | 3/2017 | Cheney | A61B 17/0642 |
| 2017/0202552 A1 | 7/2017 | Coleman | |
| 2017/0252036 A1 | 9/2017 | Palmer | |
| 2018/0008263 A1 | 1/2018 | Goldstein | |
| 2019/0000451 A1 | 1/2019 | Majors | |
| 2019/0105040 A1 | 4/2019 | Gordon | |
| 2019/0150921 A1 | 5/2019 | Fonte | |
| 2019/0192140 A1 | 6/2019 | Ducharme | |
| 2019/0192160 A1 | 6/2019 | Stamp | |
| 2019/0357951 A1 | 11/2019 | Rogers | |

* cited by examiner

LOW PROFILE STAPLE AND METHODS FOR USING THE SAME

CROSS REFERENCE TO RELATED APPLICATIONS

This application is a continuation-in-part of and claims the benefit under 35 U.S.C. § 120 to:

U.S. Design patent application Ser. No. 29/659,375, filed Aug. 8, 2018, entitled "LOW PROFILE STAPLE;" and U.S. patent application Ser. No. 16/393,489, filed Apr. 24, 2019, entitled "LOW PROFILE STAPLE AND METHODS FOR USING SAME," which is a continuation of U.S. patent application Ser. No. 16/058,638, now U.S. Pat. No. 10,307,156, filed Aug. 8, 2018, entitled "LOW PROFILE STAPLE AND METHODS FOR USING SAME," each of which is incorporated herein by reference as if set forth in their entireties.

BACKGROUND

Generally, surgical staples are used in some orthopedic indications for holding two bone segments together. Typically, segments of the same bone are separated (e.g., broken, fractured, etc.) and legs of a staple are inserted into each bone segment to compress ends of two (or more) segments of a broken bone together to promote healing of the bone (e.g., such that the bone segments heal back together).

As will be understood, staples can compress bone segments together based on stored strain profiles of the staples. At minimum, such compression can limit the distance between broken bone segments, thereby possibly helping reduce bone healing time by eliminating gaps that need to be filled by the bones/body when healing. Further, such compression may help increase/speed bone growth.

As will also be understood, space within a body is limited and lower profile staples are desirable. However, in creating a low-profile staple (e.g., a staple that has minimum rise above the surface of a bone when the staple is fully inserted), the amount of stored strain (e.g., amount of compression the staple can impart when inserted) may be limited due to certain design constraints. Further, such low-profile staples may include localized strain concentrations (at corners and the like), which may increase risk of fatigue failure.

Therefore, there exists a need for a low profile surgical staple that has the capacity for high sustained compression and that minimizes localized strain concentrations.

BRIEF SUMMARY OF THE DISCLOSURE

Briefly described, and according to one embodiment, aspects of the present disclosure generally relate to an improved low profile staple with high sustained compression and improved fatigue performance (e.g., minimized localized strain concentrations).

According to a first aspect, a staple comprising: A) a first leg connected to a bridge at a first shoulder; and B) a second leg connected to the bridge at a second shoulder, wherein: 1) the bridge comprises a central bridge portion between a radial point of the first shoulder and a radial point of the second shoulder, the central bridge portion comprising: i) a substantially continuous cross-section; ii) a first edge and a second edge; and iii) a constant width that is greater than a thickness of the central bridge portion and a non-breaking surface between the first edge and the second edge.

According to a second aspect, the staple of the first aspect or any other aspect, wherein one or more of the first leg and the second leg comprises a proximal end and a distal end and each distal end includes a wedge-shaped tip.

According to a third aspect, the staple of the second aspect or any other aspect, wherein one or more of the first leg and the second leg comprises an inner surface and a plurality of teeth, wherein each of the plurality of teeth are cut out of a respective leg such that a point of each tooth lies substantially in the same plane as the inner surface of the respective leg;

According to a fourth aspect, the staple of the third aspect or any other aspect, wherein the staple comprises nitinol.

According to a fifth aspect, the staple of the fourth aspect or any other aspect, wherein: A) a length of the central bridge portion is at least 9 mm; and B) a radius of the non-breaking surface of the bridge is at least 8 mm.

According to a sixth aspect, the staple of the fifth aspect or any other aspect, wherein the length of the central bridge portion is at least 13 mm.

According to a seventh aspect, the staple of the sixth aspect or any other aspect, wherein the constant width of the central bridge portion is approximately 3.0-7.5 mm.

According to an eighth aspect, the staple of the seventh aspect or any other aspect, wherein the thickness of the central bridge portion is approximately 0.5-2.9 mm.

According to a ninth aspect, the staple of the eighth aspect or any other aspect, wherein the first inner leg forms an angle of greater than approximately 16 degrees with the second inner leg in a relaxed position.

According to a tenth aspect, the staple of the ninth aspect or any other aspect, wherein the first inner leg is substantially parallel with the second inner leg in a stressed position.

According to an eleventh aspect, the staple of the tenth aspect or any other aspect, wherein strain is distributed substantially evenly throughout the bridge in the stressed position.

According to a twelfth aspect, the staple of the eleventh aspect or any other aspect, wherein the staple comprises two legs.

According to a thirteenth aspect, the staple of the twelfth aspect or any other aspect, wherein the staple comprises more than two legs.

According to a fourteenth aspect, the staple of the thirteenth aspect or any other aspect, wherein the staple comprises four legs.

According to a fifteenth aspect, the staple of the fourteenth aspect or any other aspect, wherein the staple comprises more than four legs.

According to a sixteenth aspect, a method of using a surgical staple, the method comprising: A) deforming a nitinol staple from a first position to a second position for inserting the nitinol staple into tissue of a patient, wherein: 1) the nitinol staple comprises: i) a bridge comprising a central bridge portion between a radial point of a first shoulder and a radial point of a second shoulder, the central bridge portion comprising: a) a substantially continuous cross-section; b) a first edge and a second edge; and c) a constant width that is greater than a thickness of the central bridge portion and a non-breaking surface between the first edge and the second edge; and ii) two or more legs integrally formed with the bridge; 2) in the first position, each of the two or more legs forms an angle of greater than approximately 16 degrees with at least one other leg of the two or more legs; 3) in the second position, each of the two or more legs are substantially parallel with the at least one other leg of the two or more legs and strain is distributed substantially evenly throughout the bridge; and 4) the nitinol staple, when inserted into the tissue of the patient, exerts compressive force on the tissue of the patient.

According to a seventeenth aspect, the method of the sixteenth aspect or any other aspect, wherein one or more of the two or more legs comprises an inner surface and a plurality of teeth, wherein each of the plurality of teeth are cut out of a respective leg such that a point of each tooth lies substantially in the same plane as the inner surface of the respective leg;

According to an eighteenth aspect, the method of the seventeenth aspect or any other aspect, wherein: A) a length of the central bridge portion is at least 9 mm; and B) a radius of the non-breaking surface of the bridge is at least 8 mm.

According to a nineteenth aspect, the method of the eighteenth aspect or any other aspect, wherein the nitinol staple comprises two legs.

According to a twentieth aspect, the method of the nineteenth aspect or any other aspect, wherein the nitinol staple comprises four legs.

These and other aspects, features, and benefits of the claimed invention(s) will become apparent from the following detailed written description of the disclosed embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
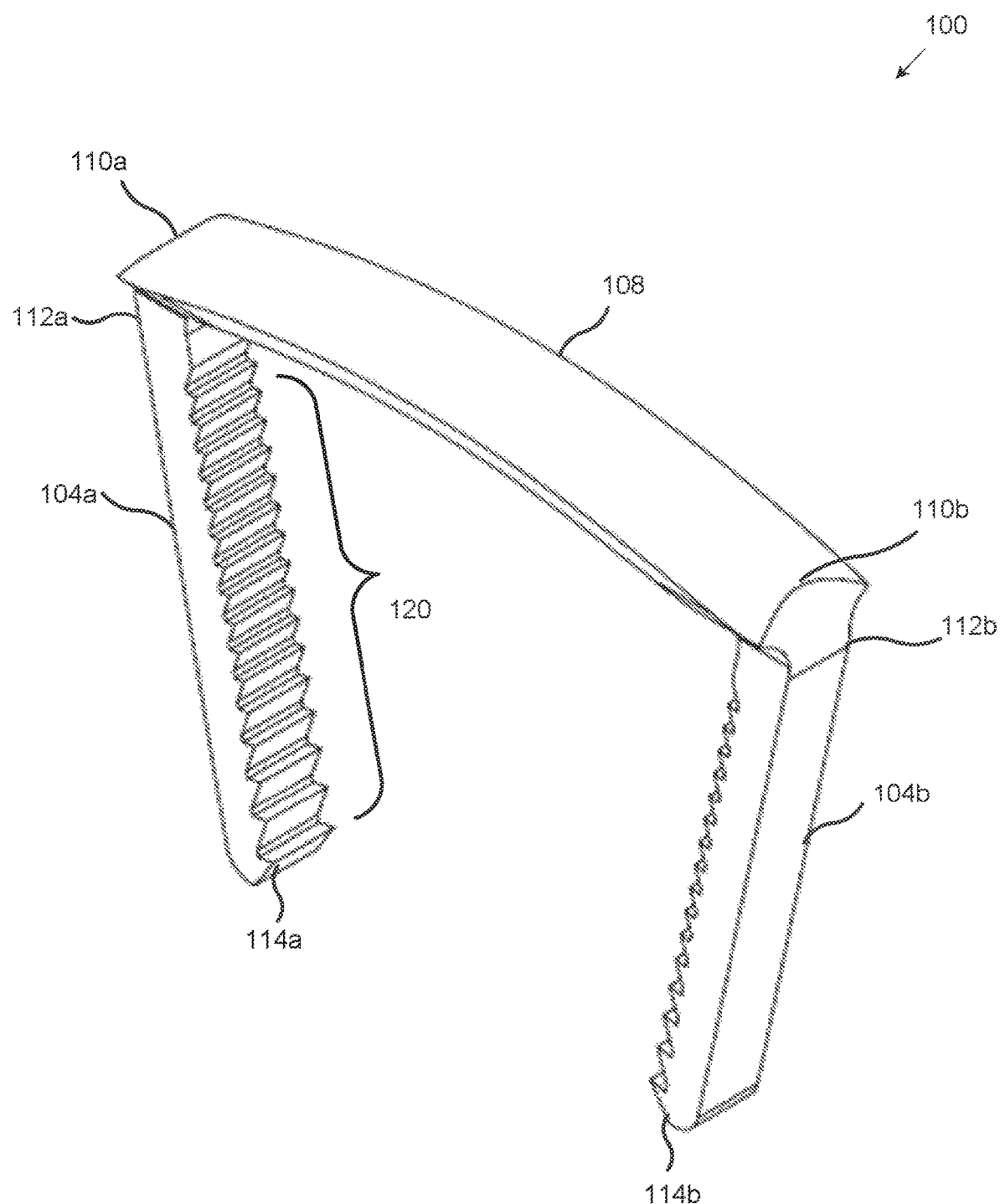
FIG. 1 illustrates a perspective view of an exemplary staple, according to one embodiment of the present disclosure.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Overview

According to particular embodiments, the present staple includes a low-profile bridge that has the capacity for high sustained compression and improved fatigue performance (e.g., minimized localized strain concentrations). In some embodiments, the staple includes a bridge with a continuous cross-section, legs with teeth cut therein (e.g., opposed to protruding from, as discussed herein), and legs with an angle of about 24 degrees (e.g., 12 degrees from vertical).

Some existing staples may include bridges with a discontinuous cross-section, which may limit the arch/radius of the bridge and likewise limit the angle at which the legs are positioned. As will be understood, the amount of compression a staple can impart on bone segments is related to the arch/radius of the bridge and angle in which the legs are positioned. In general, the greater the angle of the legs from vertical, the greater sustained compression the staple can impart on bone segments.

For example, a particular bone staple is manufactured with an arched bridge of a particular radius and legs of a particular angle from vertical. Continuing with this example, for insertion into one or more bone segments, the staple is deformed such that the bridge is substantially flattened/straightened from its resting arched position and the legs are substantially parallel/perpendicular to the substantially flattened bridge (e.g., the legs are at 0 degrees from vertical or are vertical). In this position, in this example, the staple stores strain as the bridge and legs attempt to return to their first position. As will be understood, the amount of stored strain is related to the arch/radius of the bridge and the angle of the legs. Therefore, the greater the arch/radius of the bridge and the greater the angle of the legs, the more stored strain in the staple and the more potential sustained compression force the staple can impart on bone segments upon insertion.

In another example, a particular bone staple is manufactured and/or packaged (e.g., in an insertion device) in a deformed state. Continuing with this example, the particular bone staple remains in the deformed state until the particular bone staple is implanted into a target site (e.g., via discharge from an insertion device). In the same example, upon implantation, the particular bone staple self-configures (e.g., due to stored strain) to a non-deformed state, such as a first position described herein.

As will be recognized by one of ordinary skill in the art, the staples disclosed herein have a number of advantages over previously designed staples.

First, various embodiments of the staples disclosed herein have a bridge with a continuous, low profile cross-section. Such a cross-section enables the bridge to have more stored strain and minimized localized strain than a bridge with a discontinuous cross-section (e.g., facets, different cross-sections in various portions of the bridge, etc.).

Second, some embodiments of the staples disclosed herein include teeth that are cut out of the legs (opposed to protruding therefrom). In these embodiments (and others), the legs may be wider/thicker than other staples, but have a similar structure for the teeth. As will be understood, wider/thicker legs may result in increased stiffness as compared to staples with less wide/thick legs. As will also be understood, stiff legs (along with a constant-cross-section bridge) may help distribute stored strain of a particular staple substantially evenly along the bridge portion, minimizing or eliminating stress concentrations at the interface of the legs and bridge (or at corners or surface features of a non-continuous cross-section bridge).

Third, a combination of the above elements and advantages may result in a staple that is lower profile (along the entire bridge), has higher sustained compression (and higher compression force on a patient's tissue) for longer periods of time (compared to other staples), and a staple that has high durability (lower fatigue failure/improved fatigue performance) than other staples.

As will be understood, the exemplary staples discussed herein may be manufactured from any suitable material, including, but not limited to, stainless steel, titanium, nitinol, biocompatible materials, and/or combinations of any of the previously mentioned materials.

Various aspects of the instant staple will be discussed in the following sections.

Exemplary Staple

Referring now to the figures, for the purposes of example and explanation of the fundamental processes and components of the disclosed staple, reference is made to FIG. 1, which illustrates an exemplary staple 100, according to one embodiment of the present disclosure. In various embodiments, the staple 100 includes a bridge 108 and two legs (104a, 104b). The staple 100 size (bridge×leg length) may be greater than, less than or equal to about 8 mm×8 mm, 10 mm×10 mm, 12 mm×12 mm, 14 mm×14 mm, 18 mm×18 mm, 18 mm×20 mm, 20 mm×18 mm, 20 mm×22 mm, or 26 mm×20 mm.

Figure 8:
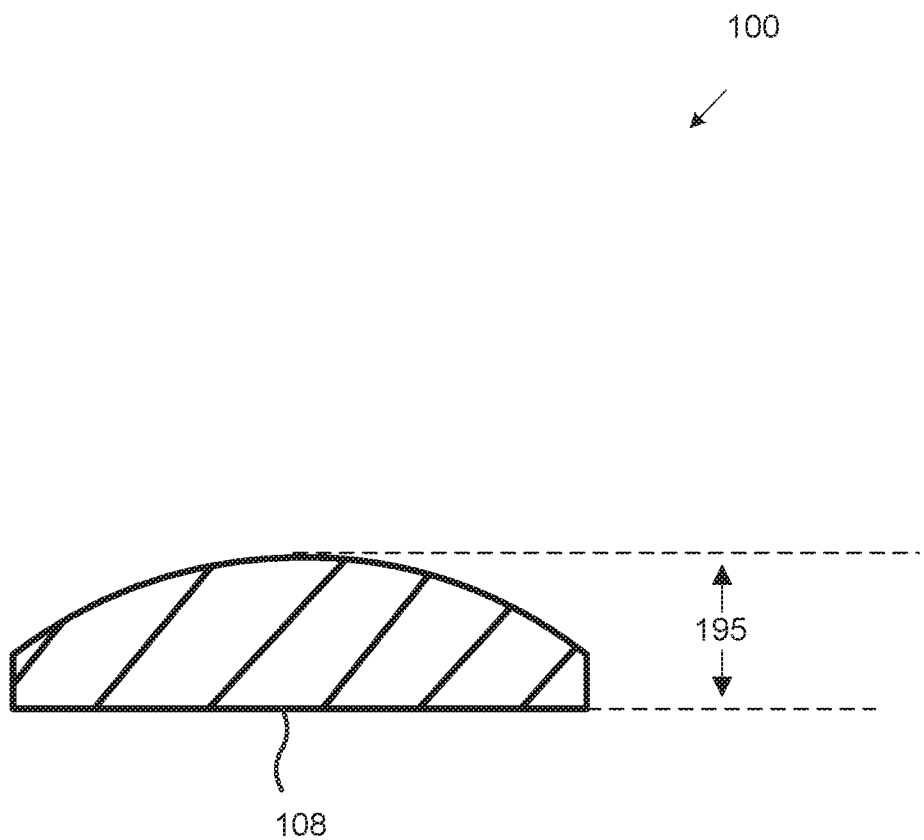
FIG. 8 illustrates a cross-sectional view of the exemplary bridge shown in FIG. 7, according to one embodiment of the present disclosure.
Figure 9:
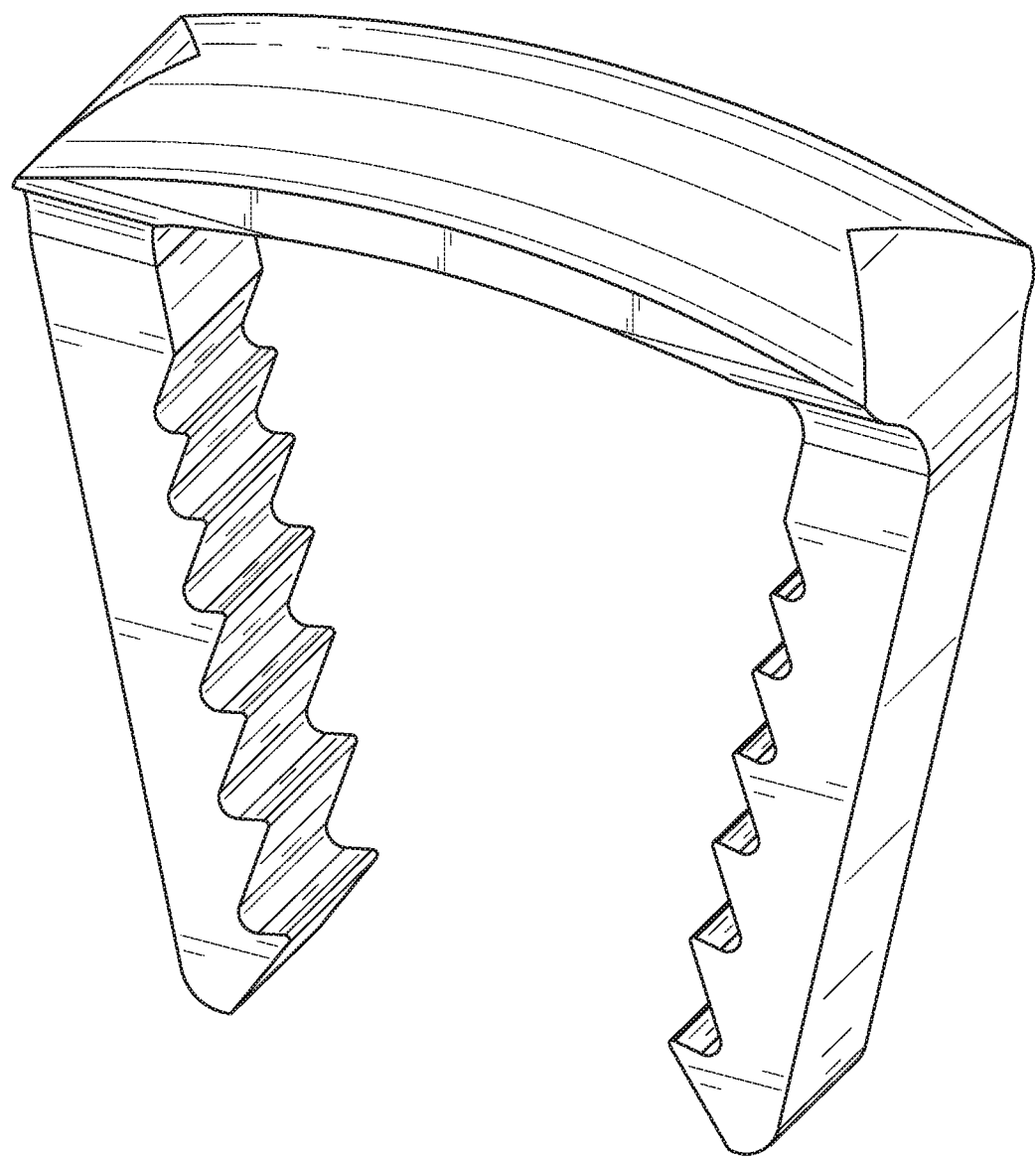
FIG. 9 is a perspective view of an exemplary low profile staple, according to one embodiment of the present disclosure.
Figure 10:
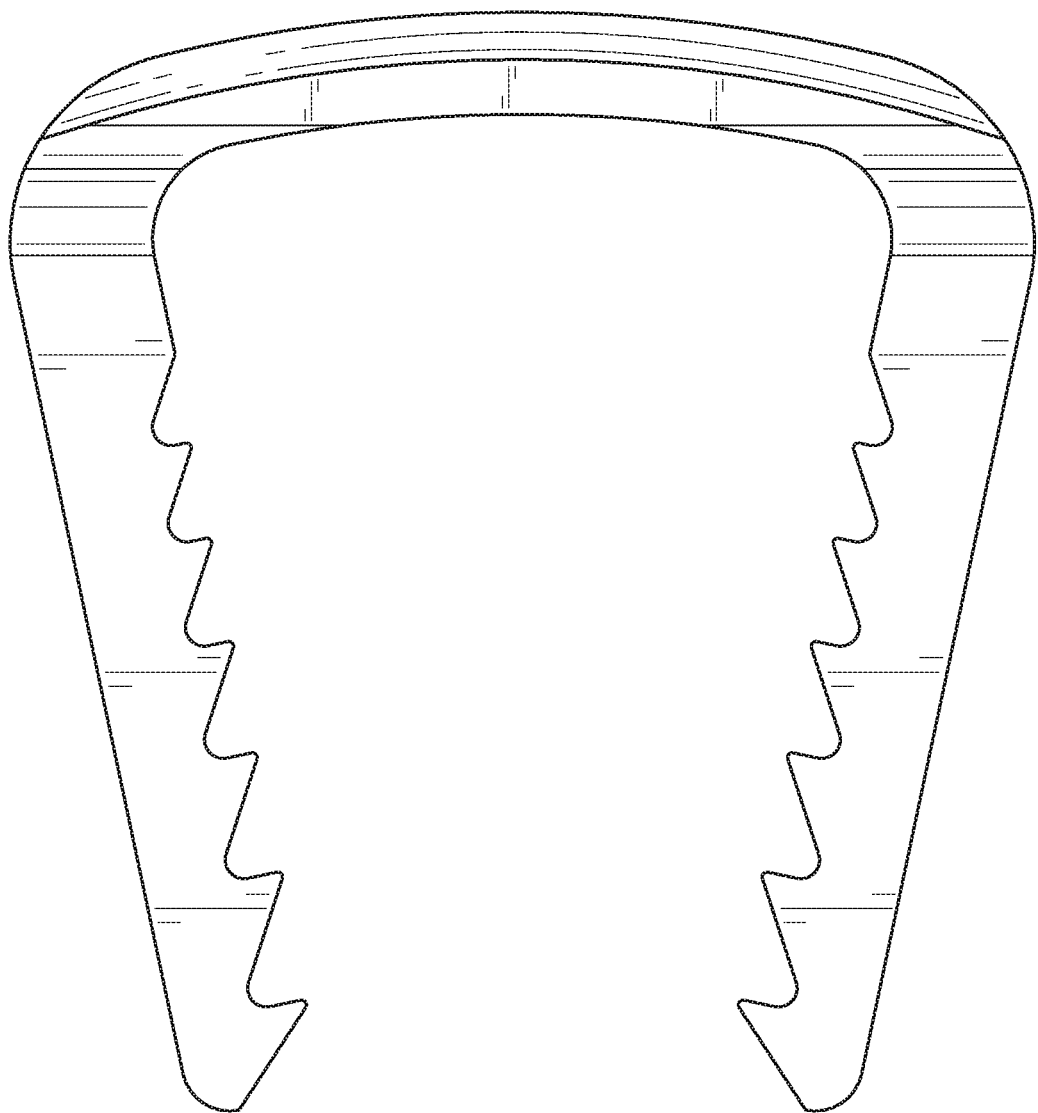
FIG. 10 is a front view of an exemplary low profile staple, according to one embodiment of the present disclosure.
Figure 11:
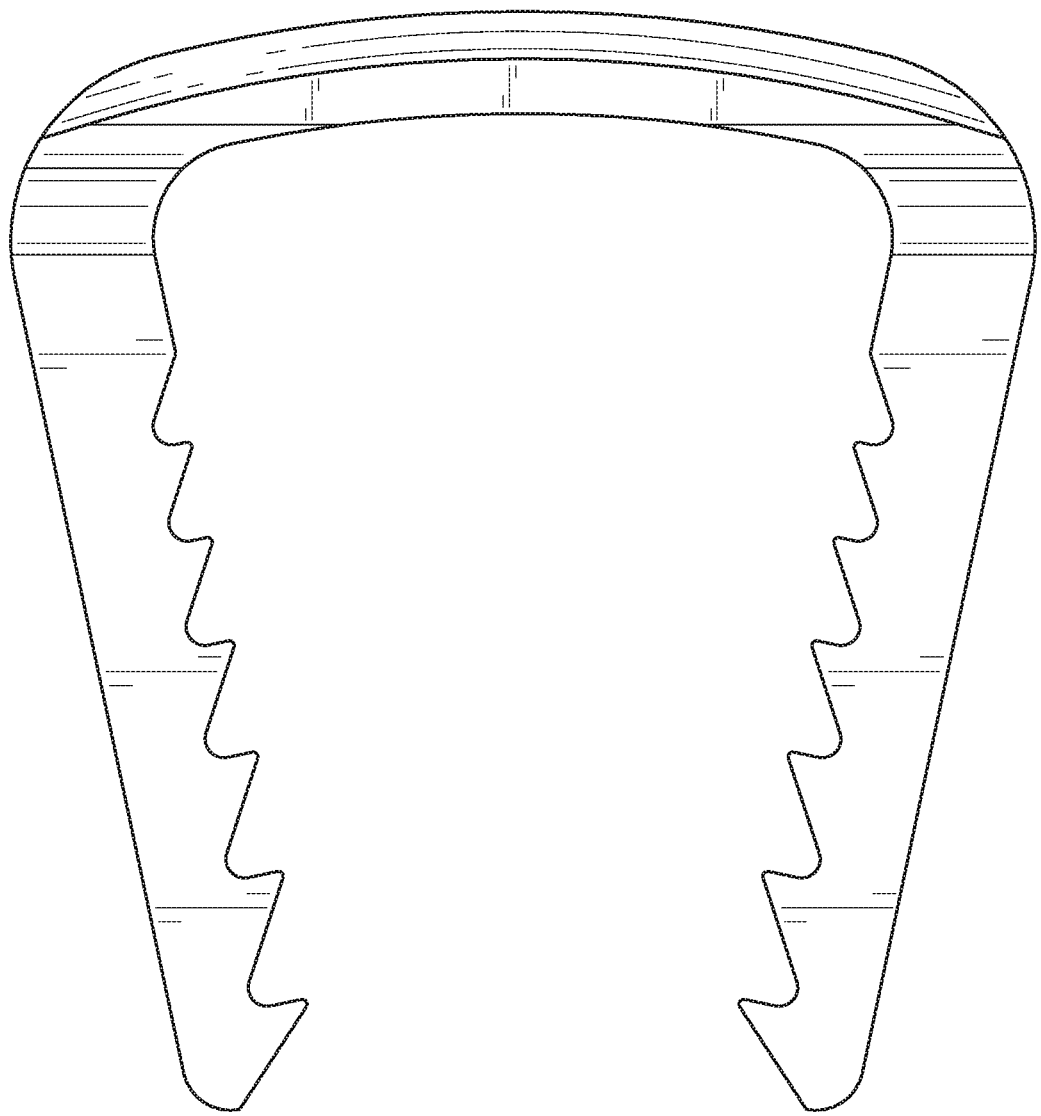
FIG. 11 is a back view of an exemplary low profile staple, according to one embodiment of the present disclosure.
Figure 12:
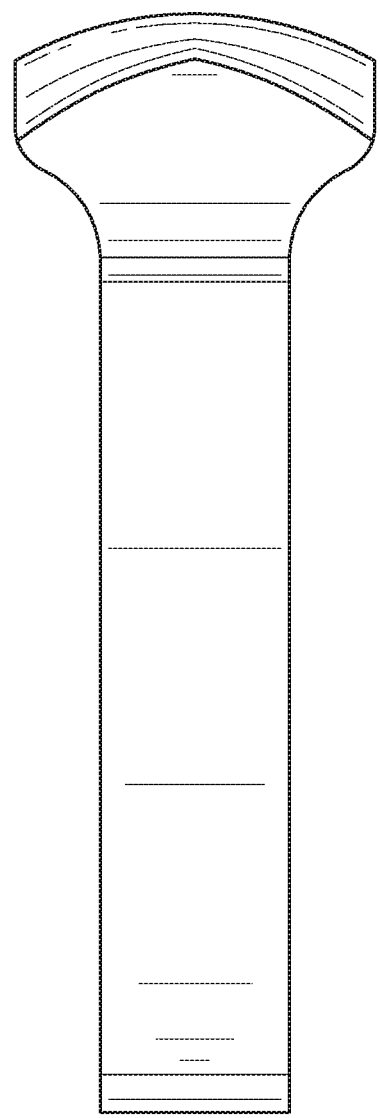
FIG. 12 is a side view of an exemplary low profile staple, according to one embodiment of the present disclosure.
Figure 13:
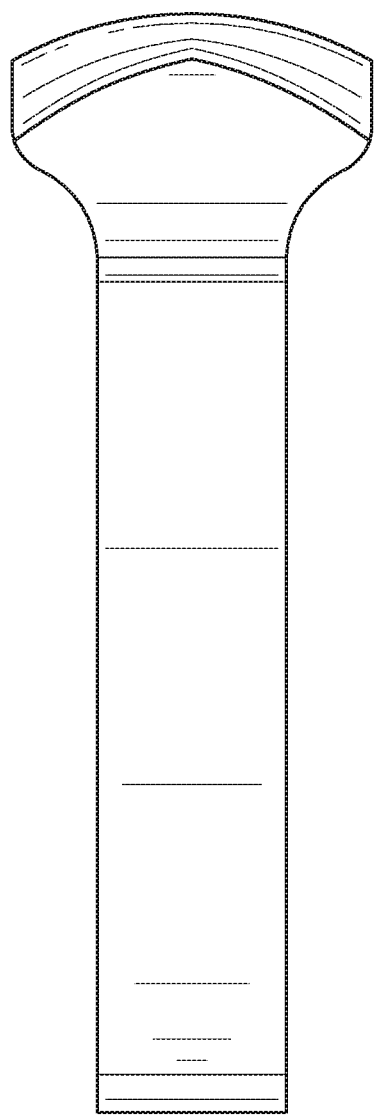
FIG. 13 is a side view of an exemplary low profile staple, according to one embodiment of the present disclosure.
Figure 14:
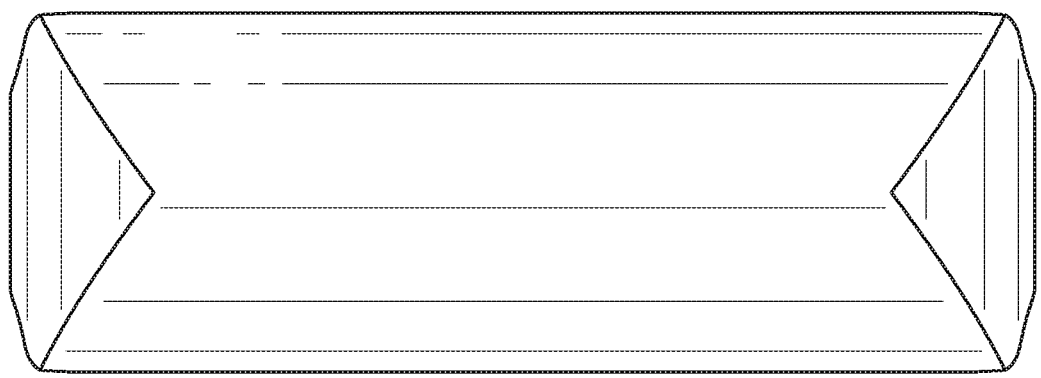
FIG. 14 is a top view of an exemplary low profile staple, according to one embodiment of the present disclosure.
Figure 15:
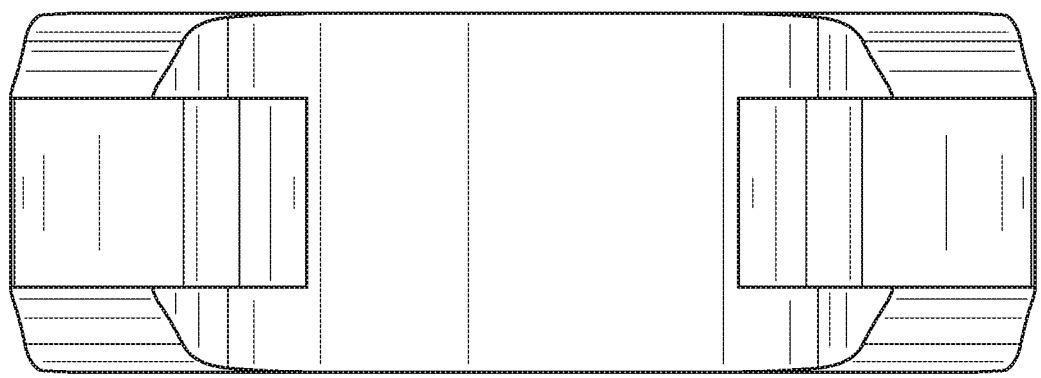
FIG. 15 is a bottom view of an exemplary low profile staple, according to one embodiment of the present disclosure.
Figure 16:
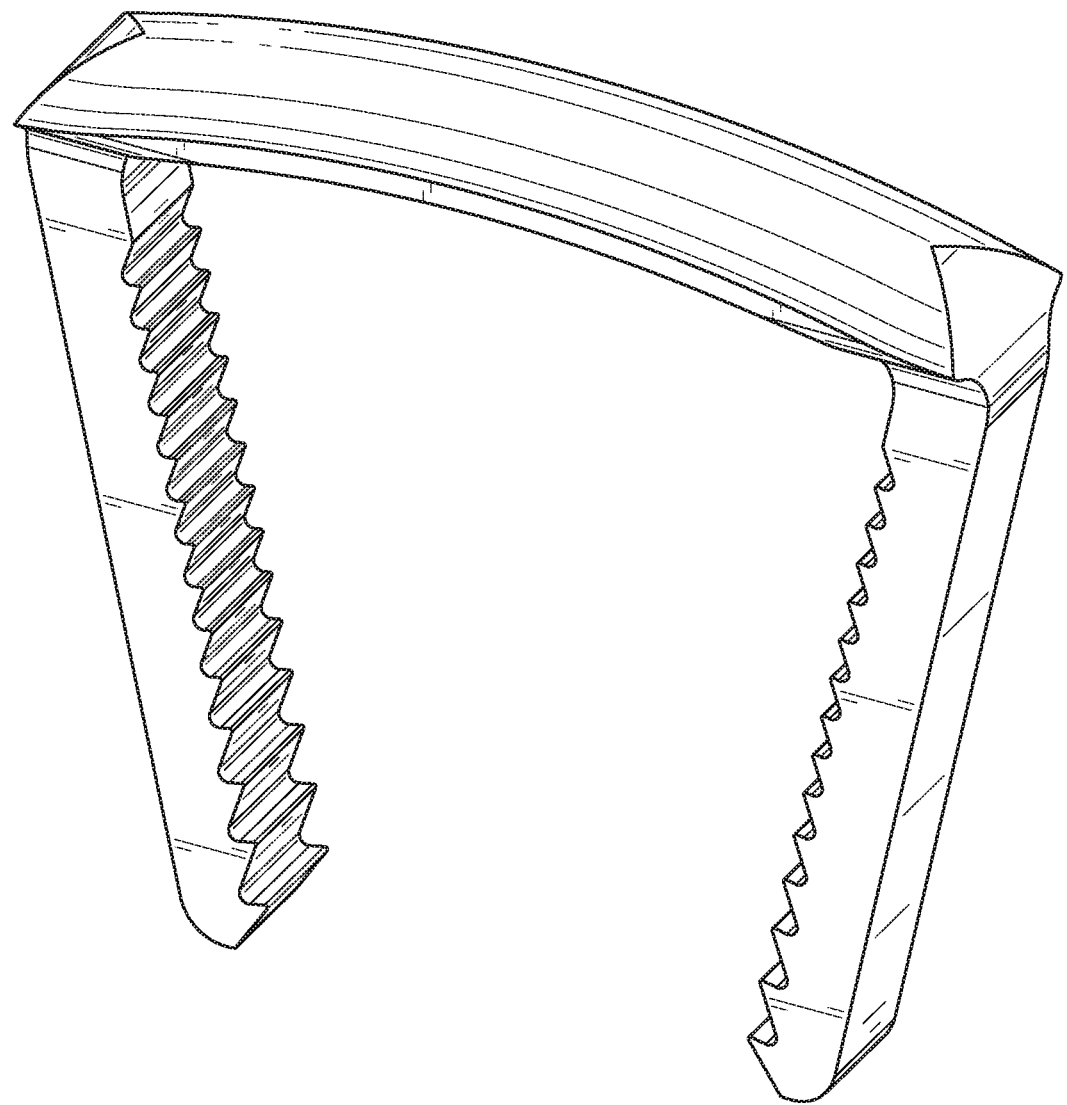
FIG. 16 is a perspective view of an exemplary low profile staple, according to one embodiment of the present disclosure.
Figure 17:
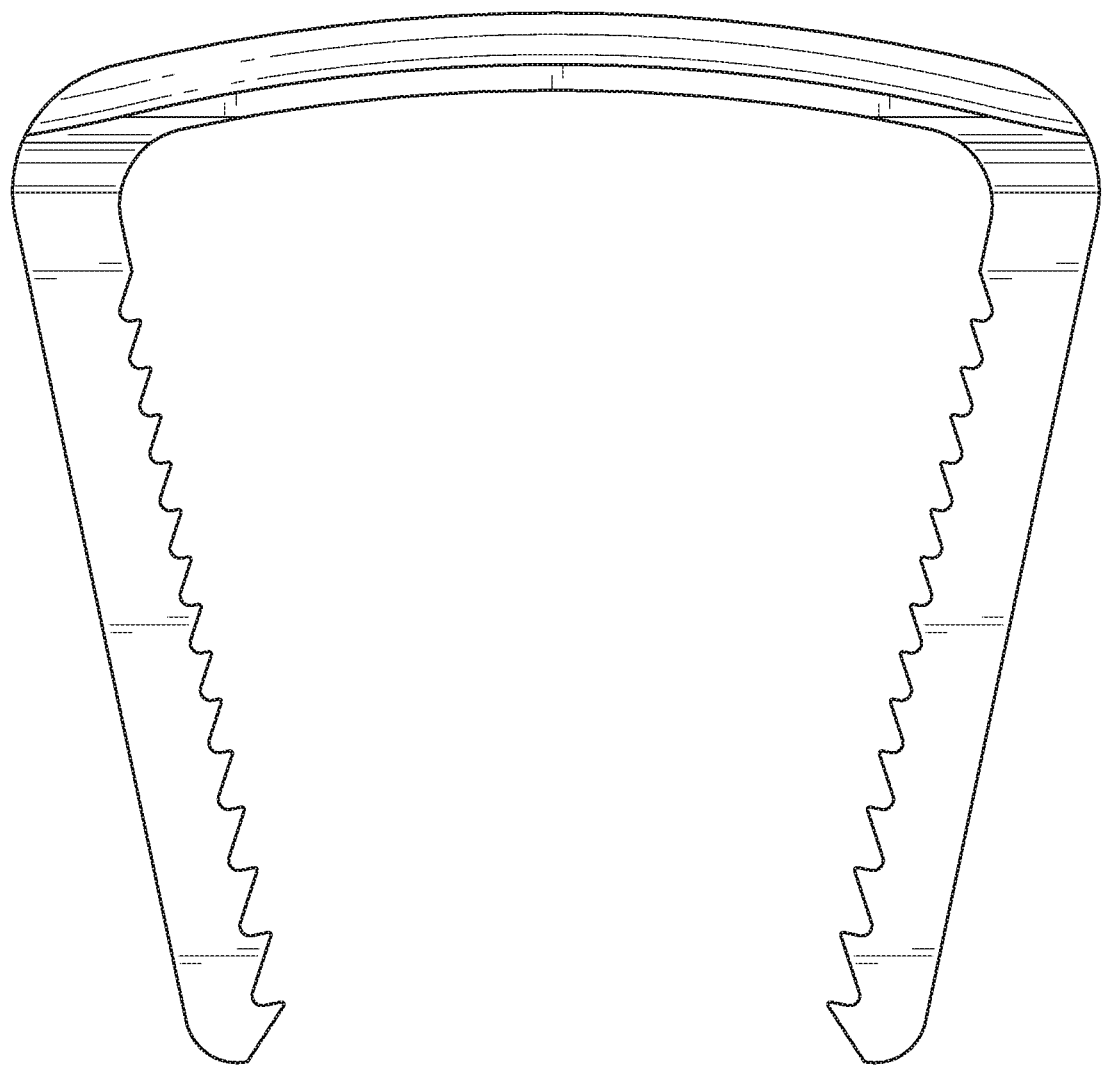
FIG. 17 is a front view of an exemplary low profile staple, according to one embodiment of the present disclosure.
Figure 18:
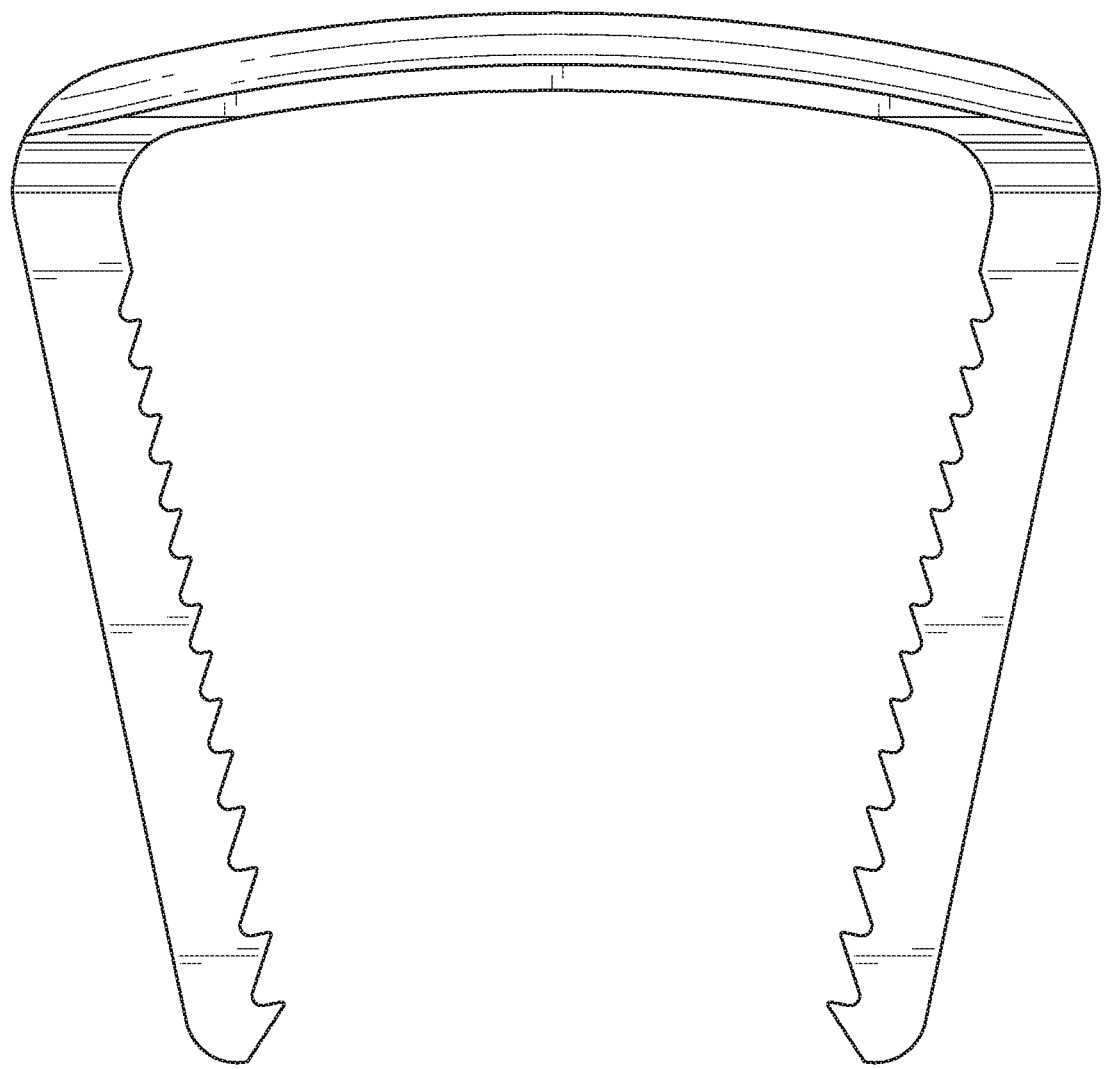
FIG. 18 is a back view of an exemplary low profile staple, according to one embodiment of the present disclosure.
Figure 19:
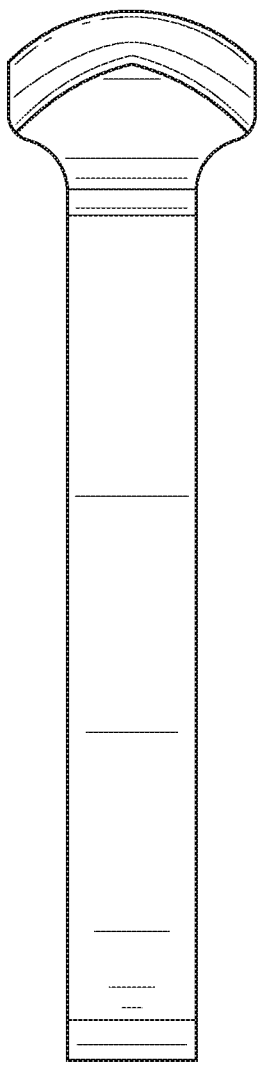
FIG. 19 is a side view of an exemplary low profile staple, according to one embodiment of the present disclosure.
Figure 20:
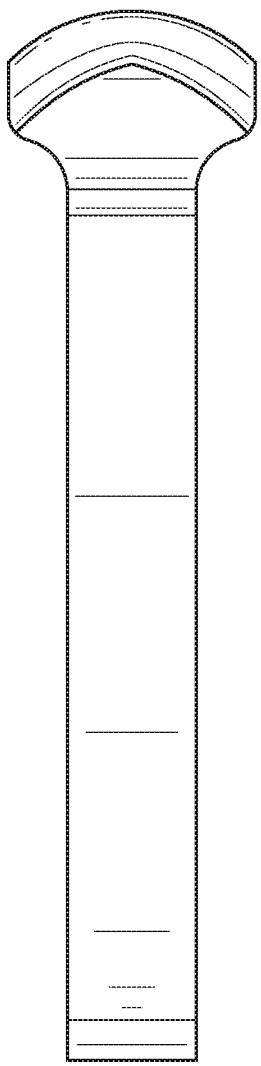
FIG. 20 is a side view of an exemplary low profile staple, according to one embodiment of the present disclosure.
Figure 21:
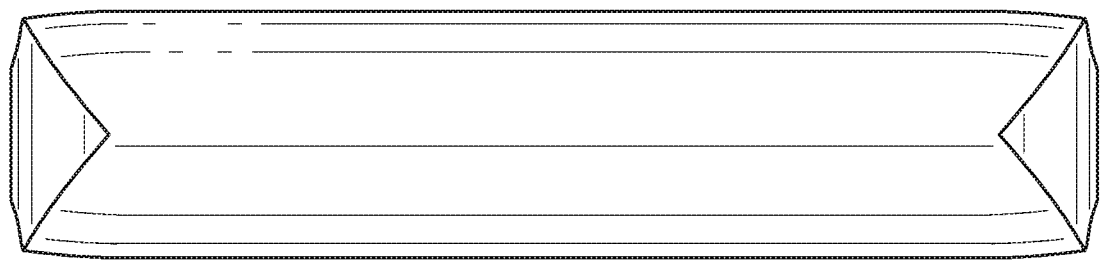
FIG. 21 is a top view of an exemplary low profile staple, according to one embodiment of the present disclosure.
Figure 22:
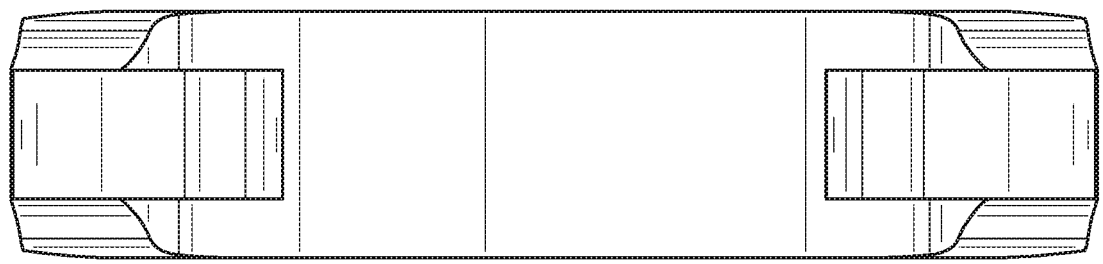
FIG. 22 is a bottom view of an exemplary low profile staple, according to one embodiment of the present disclosure.

In particular embodiments, the bridge 108 has a first end 110a and a second end 110b and includes a substantially constant cross-section between the first end 110a and the second end 110b (as further discussed in relation to FIG. 8). In at least one embodiment, the bridge 108 is substantially smooth across a top surface (e.g., between ends 110a and 110b). In some embodiments, the bridge 108 includes one or more particular radii, which will be further discussed regarding FIG. 5.

In various embodiments, the staple 100 includes legs 104a and 104b that are integrally formed with the bridge 108. In some embodiments, the legs 104a and 104b may be generally straight from a proximal end (112a, 112b) to a distal end (114a, 114b) and may have a generally rectangular cross-section. In some embodiments, the legs (104a, 104b) may have any suitable shape (e.g. generally cylindrical, serpentine, obround, oval, tubular, etc.).

As shown in the embodiment of FIG. 1, each of the legs 104a and 104b include a distal end (114a, 114b). As shown, each of the distal ends 114a and 114b are formed into a wedge-like shape for easier insertion of a staple leg into tissue (e.g., bone). The distal ends 114a and 114b may form any suitable shape (e.g., points, rounded edges, blocked edges, etc.).

In various embodiments, the staple 100 may have a plurality of teeth 120 cut into the legs 104a and 104b. In some embodiments, the teeth 120 may be located on the internal face of the legs (104a, 104b). In various embodiments, the teeth 120 may extend along the entire length of the legs 104a and 104b. In some embodiments, the teeth 120 may extend along a partial length of the legs 104a and 104b. In various embodiments, the teeth 120 may be wedge-shaped, curved, straight or any combination thereof. As will be understood, a staple may include two or more legs (e.g., three, four, etc.) and each leg may have a different (or the same) number of teeth. In further embodiments, each staple leg may have different sized or shaped teeth (e.g., a staple with four legs may include teeth of a first shape along an inner pair of legs and teeth of a second shape long an outer pair of legs).

Figure 2:
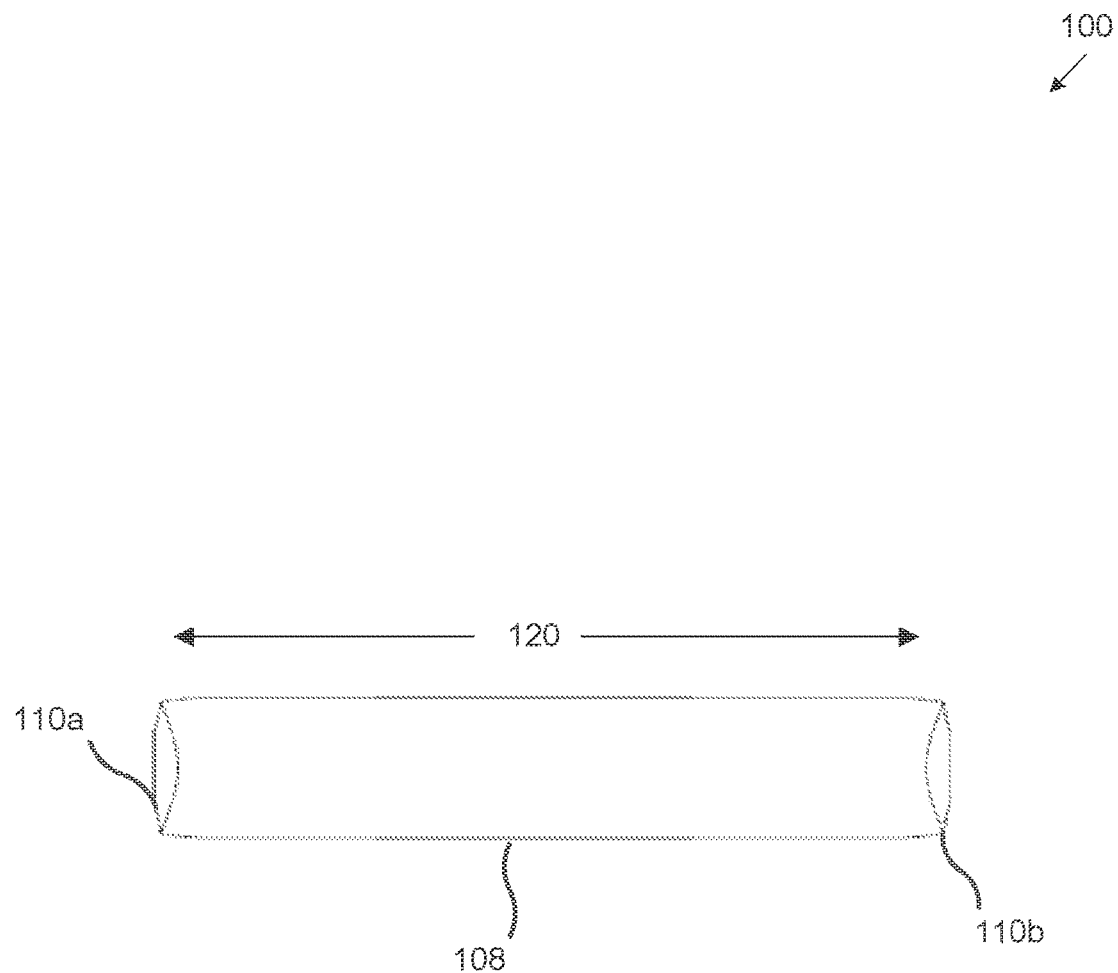
FIG. 2 illustrates a top view of an exemplary staple, according to one embodiment of the present disclosure.

FIG. 2 is a top view of a staple 100, according to one embodiment of the present disclosure. In various embodiments, the top of the staple 100 includes the bridge 108, which may be curved between two ends 110a and 110b (curvature not shown in FIG. 2), with a smooth top surface and low profile cross-section that is substantially constant throughout the entire bridge 108.

In some embodiments, the bridge 108 includes a length 120 that may be greater than, less than or equal to about 8 mm to 35 mm. In particular embodiments, the bridge 108 has a length 120 that may be greater than, less than or equal to about 8.82 mm, 10.82 mm, 12.82 mm, 14.83 mm, 19.11 mm, 21.11 mm, or 27.12 mm.

Figure 3:
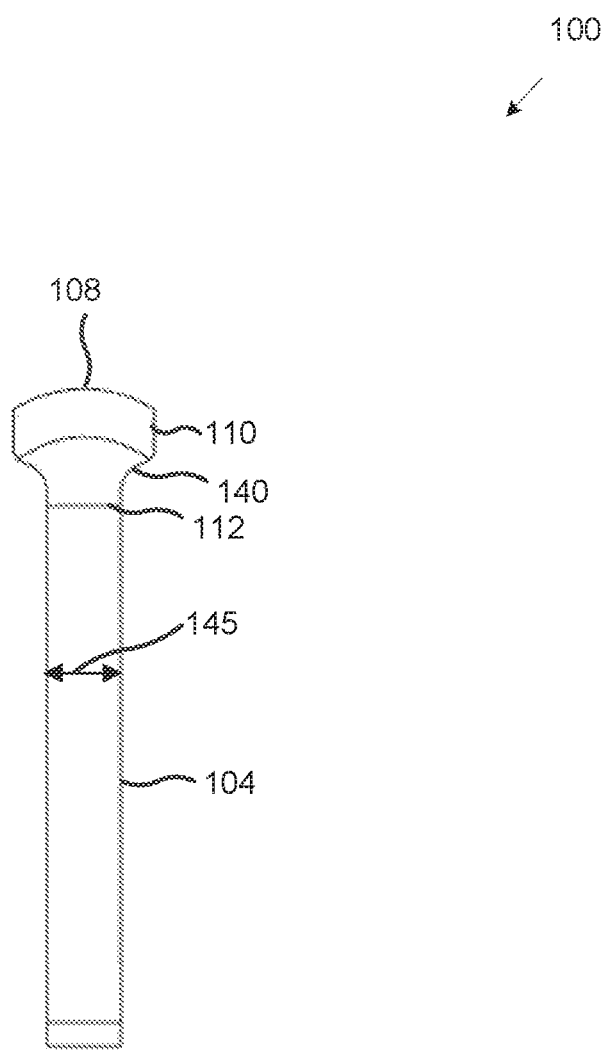
FIG. 3 illustrates a side view of an exemplary staple, according to one embodiment of the present disclosure.

FIG. 3 is a side view of a staple 100, according to one embodiment of the present disclosure. In the embodiment shown, the staple 100 includes a bridge 108 having an end 110 and a leg 104. In various embodiments, the bridge 108 is smooth and with a low-profile geometry that enables more curvature of the bridge, which may create greater sustained compression when the staple is inserted into tissue (as further discussed herein). In some embodiments, the top and bottom portion of the bridge 108 is generally arched in shape.

In various embodiments, the staple 100 may have a leg 104 connected to the bottom portion of bridge 108 near the proximal end 112 of the leg 104. In some embodiments, there is a transitional area that is sloped from the proximal end 112 of the leg 104 to the bridge 108. In some embodiments, this transitional area may have a radius that may be greater than, less than, or equal to about 1.00 mm. In at least one embodiment, the staple includes a shoulder 140 that transitions from the width of the bridge 108 to the depth 145 of the leg 104.

In some embodiments, the shoulder 140 may have one or more radii that may be greater than, less than, or equal to about 0.50 mm to 1.50 mm. In particular embodiments, the shoulder 140 has one or more radii that may be greater than, less than, or equal to about 0.50 mm, 1.00 mm, 1.50 mm, 2.00 mm, or 2.50 mm.

In some embodiments, the leg 104 may have a depth 145 that may be greater than, less than, or equal to about 1.00 mm to 3.00 mm. In particular embodiments, the leg 104 has a depth 145 that may be greater than, less than, or equal to about 1.5 mm, 2 mm, 2.5 mm, etc.

Figure 4:
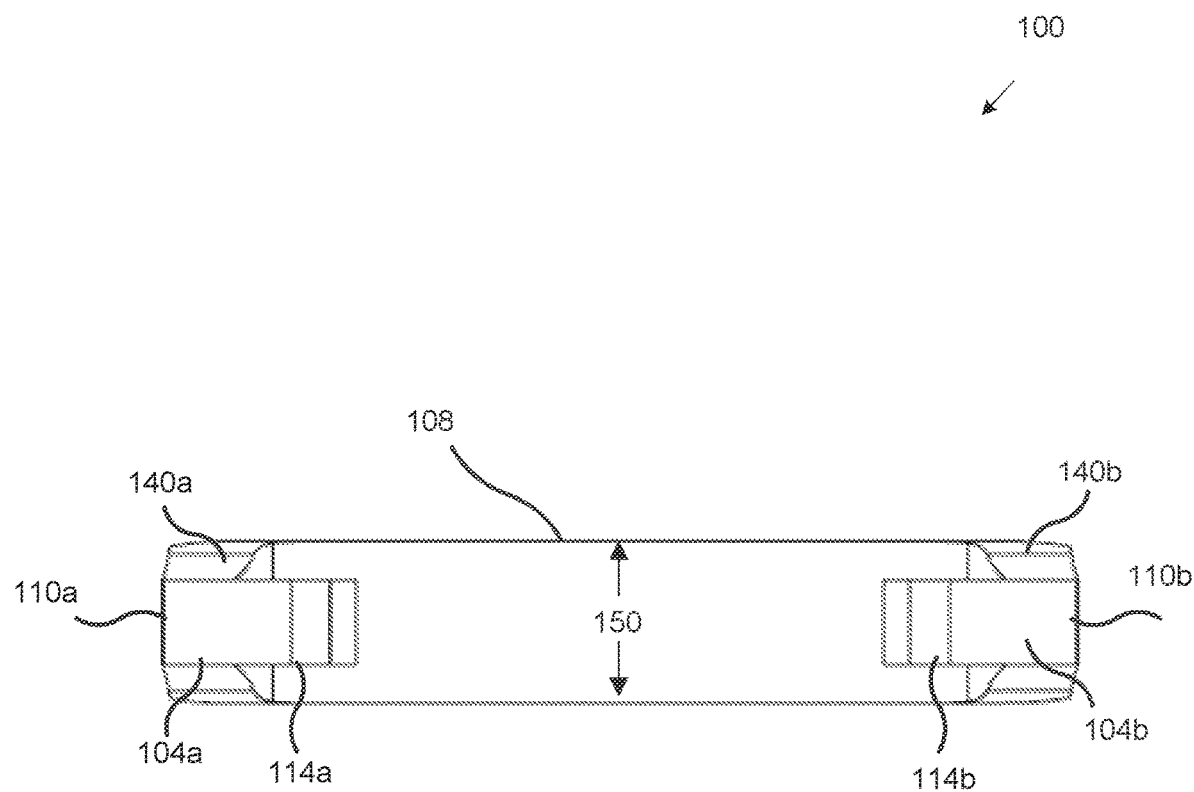
FIG. 4 illustrates a bottom view of an exemplary staple, according to one embodiment of the present disclosure.

FIG. 4 is a bottom view of a staple 100, according to one embodiment of the present disclosure. As depicted, the staple 100 includes a bridge 108 having two ends (110a, 110b) and legs (104a, 104b).

In various embodiments, the staple 100 includes a first shoulder 140a and a second shoulder 140b. As shown, the width of the bridge 150 is greater than a depth of the legs 104a and 104b (as described in relation to FIG. 3). As such, the first shoulder 140a and second shoulder 140b transition from the width of the bridge 150 to the depth of the legs 104a and 104b.

In some embodiments, midpoints of the legs 104a and 104b are located at a midpoint of the bridge 108 (e.g., the legs are positioned along a centerline of the bridge). In these embodiments (and others), the shoulders 140a and 140b include a slope, arch, or other transition from each edge of the bridge 108 to an edge of each of the legs 104a and 104b. In particular embodiments, the transition from the width of the bridge 108 to the depth of the legs 104a and 104b is substantially gradual and constant (e.g., a gradual slope or a constant radius arch). In some embodiments, the slope includes more than one slope of varying pitch or multiple arches of varying radii.

In some embodiments, the bridge 108 includes a width 150 that may be greater than, less than, or equal to about 1.00 mm to 5.00 mm. In particular embodiments, the bridge 108 has a width 150 that may be greater than, less than, or equal to about 3.80 mm and/or 4.80 mm.

Figure 5:
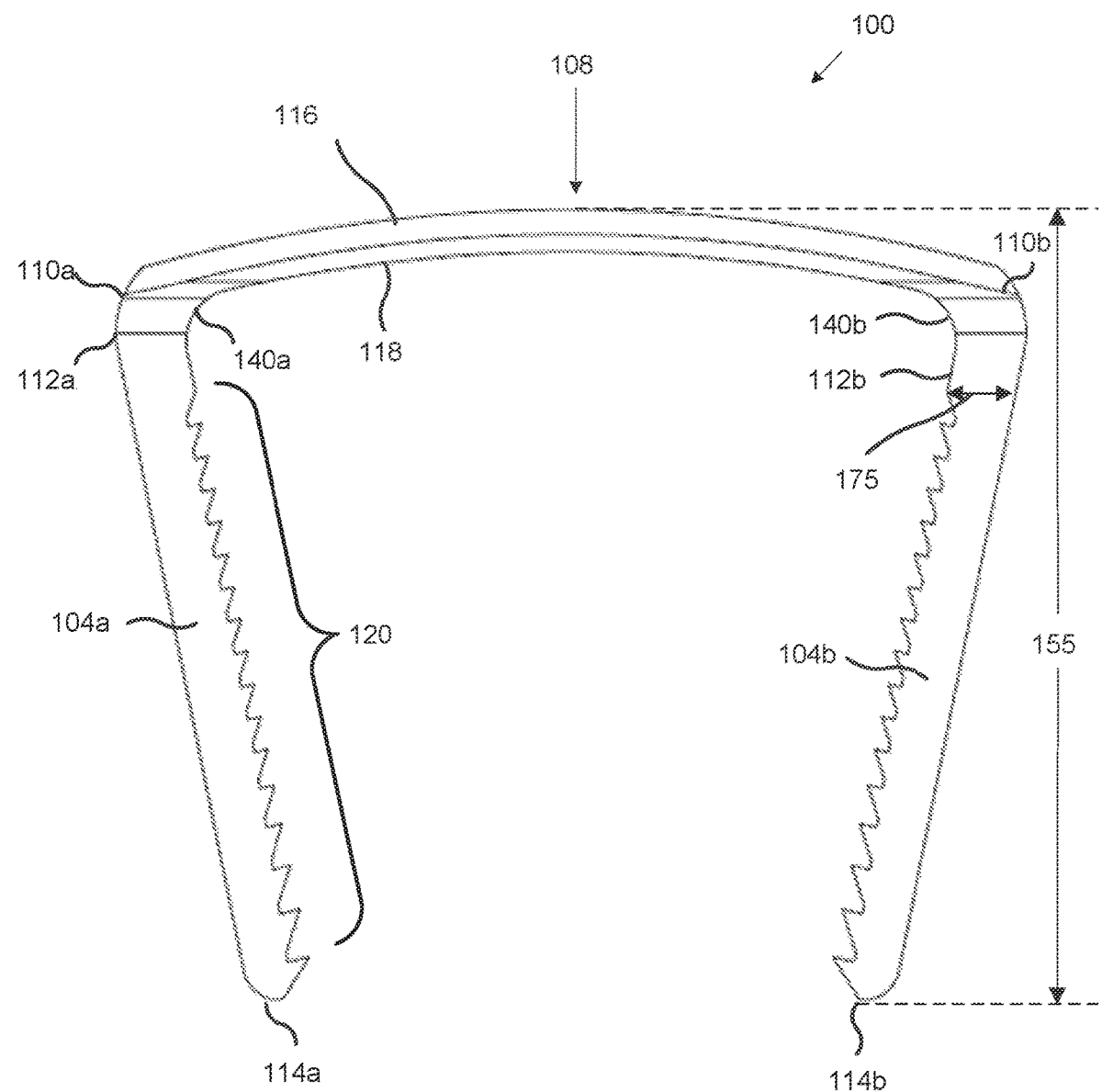
FIG. 5 illustrates a front view of an exemplary staple, according to one embodiment of the present disclosure.

FIG. 5 is a front view of a staple 100, according to one embodiment of the present disclosure. In various embodiments, the staple 100 may have a bridge component 108 having two ends (110a, 110b) and legs (104a, 104b).

As discussed herein, according to particular embodiments, the bridge 108 is smooth with a constant radius across a top surface of the entire bridge (e.g., between ends 110a and 110b). As shown in FIG. 5, the bridge 108 includes a top radius 116 and a bottom radius 118, with a transition between the two.

In some embodiments, the bridge 108 may have a top radius 116 that may be greater than, less than, or equal to about 8.00 mm to 60.00 mm. In particular embodiments, the bridge 108 has a top radius 116 that may be greater than, less than, or equal to about 11.24 mm, 16.06 mm, 20.88 mm, 25.69 mm, 31.75 mm, 36.56 mm, and/or 51.01 mm.

According to at least one embodiment, the bridge 108 may have a bottom radius 118 that may be greater than, less than, or equal to a range from about 8.00 mm to 60.00 mm. In particular embodiments, the bridge 108 may have a bottom radius 118 that may be greater than, less than, or equal to about 10.24 mm, 14.98 mm, 19.71 mm, 24.44 mm, 30.33 mm, 35.06 mm, and/or 49.26 mm.

In some embodiments, the curvature of the bridge (along with other features) may help distribute strain substantially equally long the length of the bridge. In at least one embodiment, the curvature of the bridge may help distribute strain equally between the legs (104a, 104b), shoulders (140a, 140b) and the bridge 108.

In various embodiments, the bridge 108 first end 110a includes a first shoulder 140a and the second end 110b includes a second shoulder 140b.

In various embodiments, the staple 100 legs (104a, 104b) extend downward from the bridge 108 and have smooth outer surfaces with a plurality of teeth 120 found in the inner surfaces. In various embodiments, each leg has a proximal (112a, 112b) and distal end, wherein the distal ends (114a, 114b) include bone penetrating features.

In one embodiment, the legs 104a and 104b have a particular length 155 as measured from the bottom of leg to the top of the bridge 108. In the embodiment shown, the legs 104a and 104b have substantially the same length. In some embodiments, legs 104a and 104b may have different lengths, depending on the application of the staple 100.

In some embodiments, the legs (104a, 104b) may have a length 155 greater than, less than, or equal to about 9.00 mm to 24.00 mm. In particular embodiments, the legs (104a, 104b) have a length greater than, less than, or equal to about 9.48 mm, 11.62 mm, 13.77 mm, 15.90 mm, 20.23 mm, 20.41 mm, 22.19 mm, 22.93 mm, or 24.33 mm.

In one or more embodiments, the legs (104a, 104b) may have a width 175 that may be greater than, less than, or equal to 1.00 mm to 3.00 mm. In particular embodiments, the legs (104a, 104b) have a width 175 that may be greater than, less than, or equal to 1.50 mm or 2.00 mm.

Figure 6:
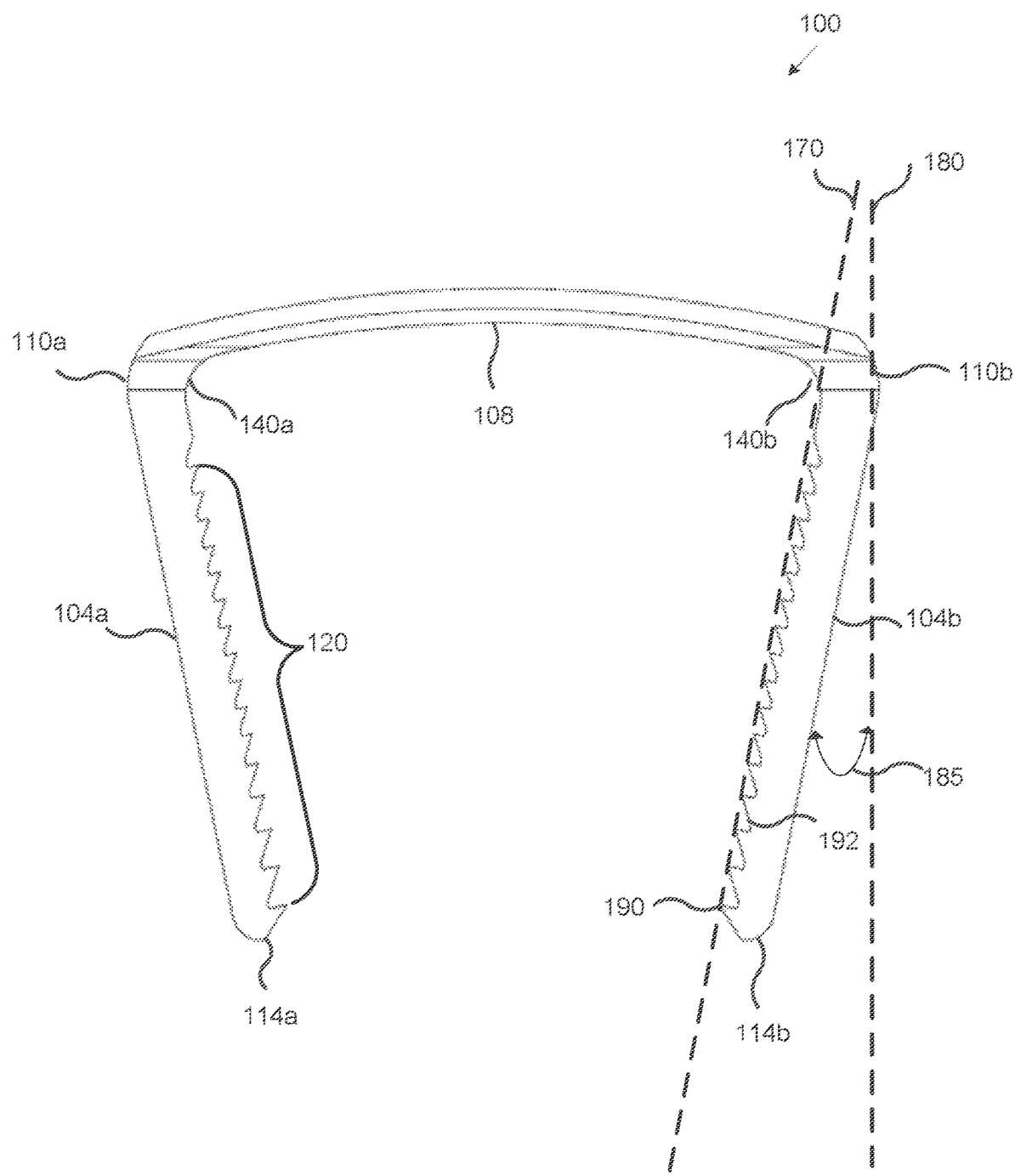
FIG. 6 illustrates a front view of an exemplary staple, according to one embodiment of the present disclosure.

Turning now to FIG. 6, a front view of a staple 100 is shown, according to one embodiment of the present disclosure. Reference lines 170 and 180 are shown in FIG. 6 to help explain how the teeth 120 are created and the angle of the leg 104b from vertical, respectively.

According to at least one embodiment, the teeth 120 are cut into the legs (104a, 104b). Stated another way, in a particular embodiment, the ends (e.g., sharpest points) of the teeth 120 lie in the same plane as an inner surface of a leg. The plane of the inner surface of leg 104b is shown approximately as reference line 170. In some embodiments, the legs (104a, 104b) of the staple 100 may have a various number of teeth 120 that may be greater than, less than, or equal to about 4, 6, 8, 10, 14, 16, or 18. The number of teeth included in the staple 100 may depend on the length of the legs of the staple 100 (e.g., a staple with longer legs may have more teeth).

In at least one embodiment, for the set of teeth 120, generally all of the teeth may be at 60 degrees. In particular embodiments, a tooth at the distal end of the legs is at an angle other than 60 degrees, such as for example, tooth 190 is at 45 degrees. In further embodiments, each tooth or a subset of teeth 120 may include any suitable angle or angles, including but not limited to about 20 to 85 degrees.

In some embodiments, each of the teeth 120 may have a depth 192 that may be greater than, less than, or equal to about 0.01 to 1.00 mm, 0.36 mm, 0.41 mm, 0.46 mm, 0.51 mm, 0.56 mm, or 0.58 mm.

As will be understood from discussions herein, all of the teeth 120 of the staple 100 may be substantially the same shape, depth, etc. In particular embodiments, the number of teeth, the size and depth of the teeth, etc. may vary along the length of the leg. In one embodiment, a leg may include a number of teeth near a distal end of a first depth and a number of teeth near a proximal end of a second depth, where the second depth is less than the first depth. In this embodiment (and others), the staple has larger teeth at the bottom of the staple and smaller teeth near the bridge of the staple.

In various embodiments, the legs (104a, 104b) are at an acute angle 185 of about 12 degrees from vertical (e.g., the angle between the legs is about 24 degrees), as indicated by reference line 180. In particular embodiments, the acute angle 185 may be any suitable angle within a range of about 5 to 15 degrees (e.g., the angle between the legs may be greater than 10 degrees). As will be understood from discussions herein, the angle of the legs 185 from vertical may be, in at least one embodiment, substantially similar to an angle measured from a horizontal line from the highest point on the bridge 108 (horizontal line not shown) to the end of the bridge 110a or 110b.

Figure 7:
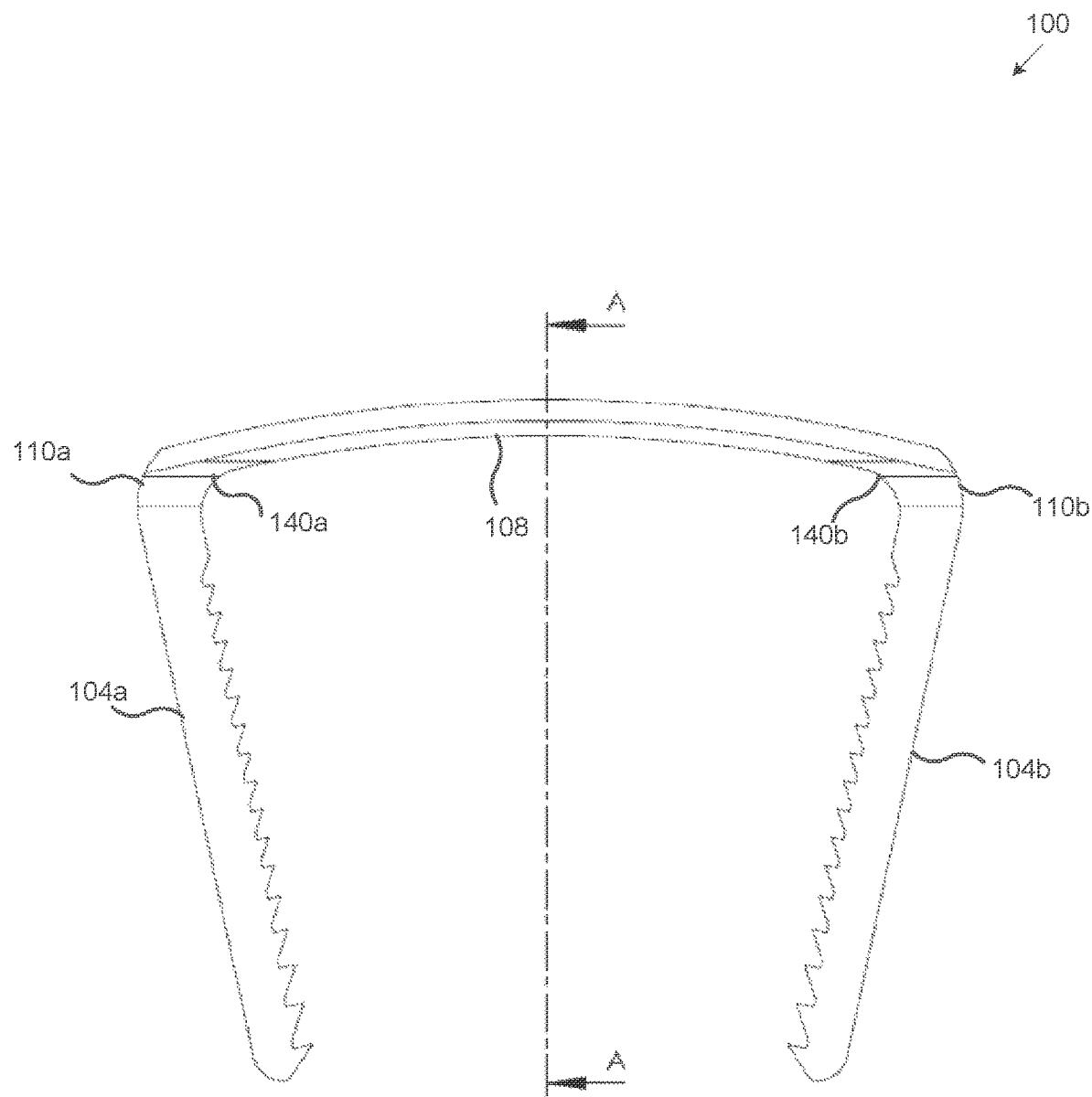
FIG. 7 illustrates a front view of an exemplary staple, according to one embodiment of the present disclosure.

FIG. 7 is a front view of a staple 100, according to one embodiment of the present disclosure. FIG. 7 shows a section line, A-A, which indicates a cross-section of the bridge 108. As shown, the section line A-A passes through an approximate midpoint of the bridge 108. As further discussed herein, the bridge 108, in particular embodiments, includes a constant cross-section. As such, although the section line A-A passes through a midpoint of the bridge 108, it should be understood that this cross-section represents any cross-section of the bridge 108. The cross-section will be further discussed below in relation to FIG. 8.

FIG. 8 is a cross-sectional view of the bridge 108 as indicated by section line A-A shown in FIG. 7, according to one embodiment of the present disclosure. As depicted, the staple 100 includes a low-profile bridge 108. In various embodiments, the bridge 108 includes a continuous radius with a smooth top surface. In at least one embodiment, the radius of the bridge cross-section top surface is about 3.00-4.00 mm. In a particular embodiment, the radius of the bridge cross-section top surface is about 3.38 mm or 3.86 mm.

As shown in FIG. 8, the bridge 108 includes a particular thickness 195. In some embodiments, the bridge 108 includes a thickness 195 that may be greater than, less than, or equal to about 1.00 mm to 3.00 mm. In particular embodiments, the bridge 108 has a thickness 195 that may be greater than, less than, or equal to about 1.00 mm, 1.08 mm, 1.17 mm, 1.25 mm, 1.42 mm, 1.50 mm or 1.75 mm.

FIGS. 9-22 show additional embodiments and features of exemplary staples discussed herein.

Figure 23:
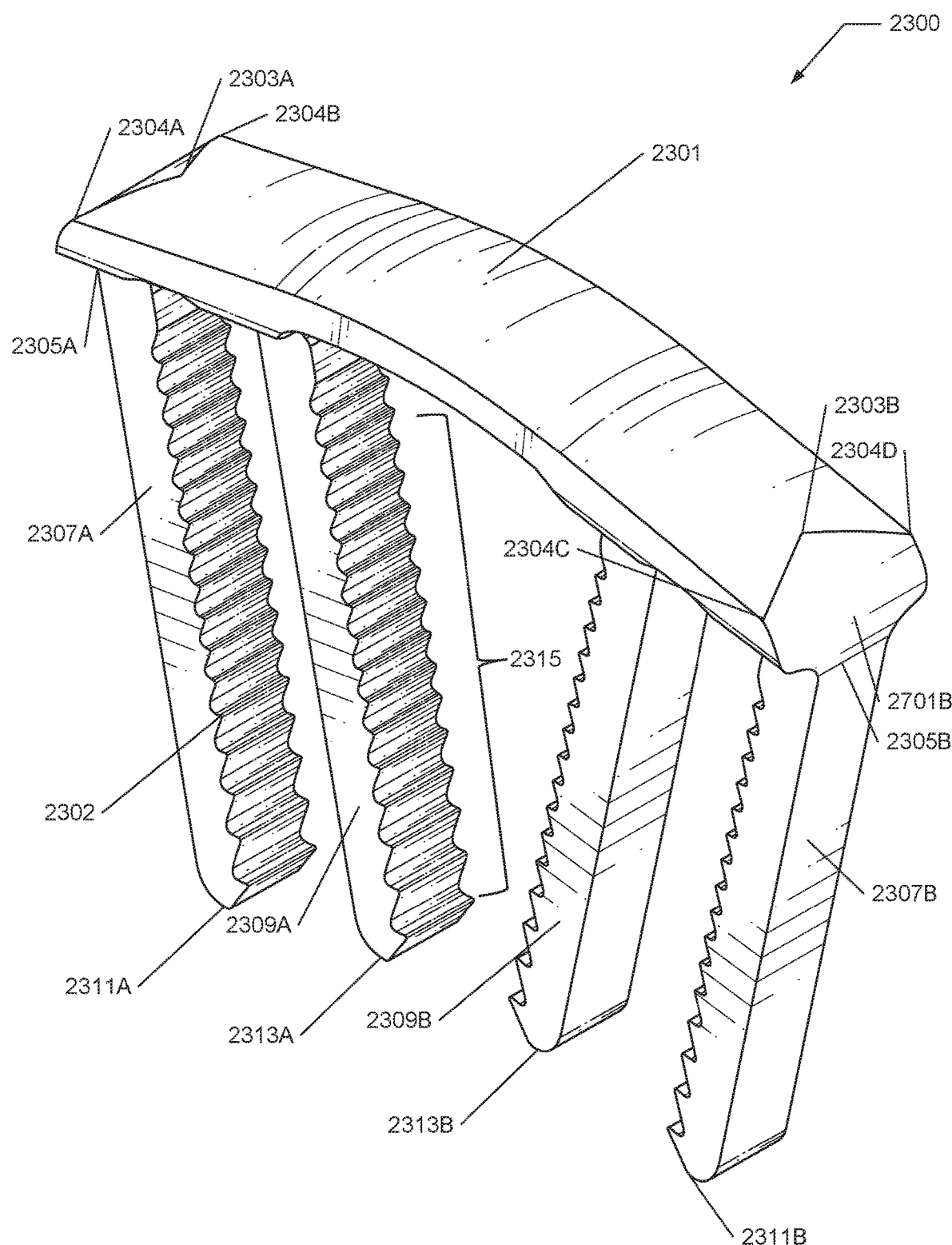
FIG. 23 is a perspective view of an exemplary low profile staple, according to one embodiment of the present disclosure.

FIG. 23 shows a perspective view of an exemplary staple 2300. In various embodiments, the staple 2300 includes a bridge 2301, at least two outer legs 2307A, 2307B, and at least two inner legs 2309A, 2309B. According to one embodiment, the staple 2300 size (bridge 2301 length×outer leg 2307 length×inner leg 2309 length) may be greater than, less than or equal to about 26.0 mm×20.0 mm×20.0 mm, 30.0 mm×20.0 mm×20.0 mm, 26.92 mm×23.28 mm×23.28 mm, or 30.86 mm×23.49 mm×23.49 mm. In various embodiments, the bridge 2301 includes a substantially rectangular shape defining four corners 2304A-D. In one or more embodiments, the corners 2304A-D are rounded to enhance a low profile feature of the bridge 2301, the roundedness reducing a likelihood of the corners 2304A-D piercing or lacerating tissue, or becoming caught on an external element (e.g., such as a wound wrapping, clothing, etc.).

Figure 28:
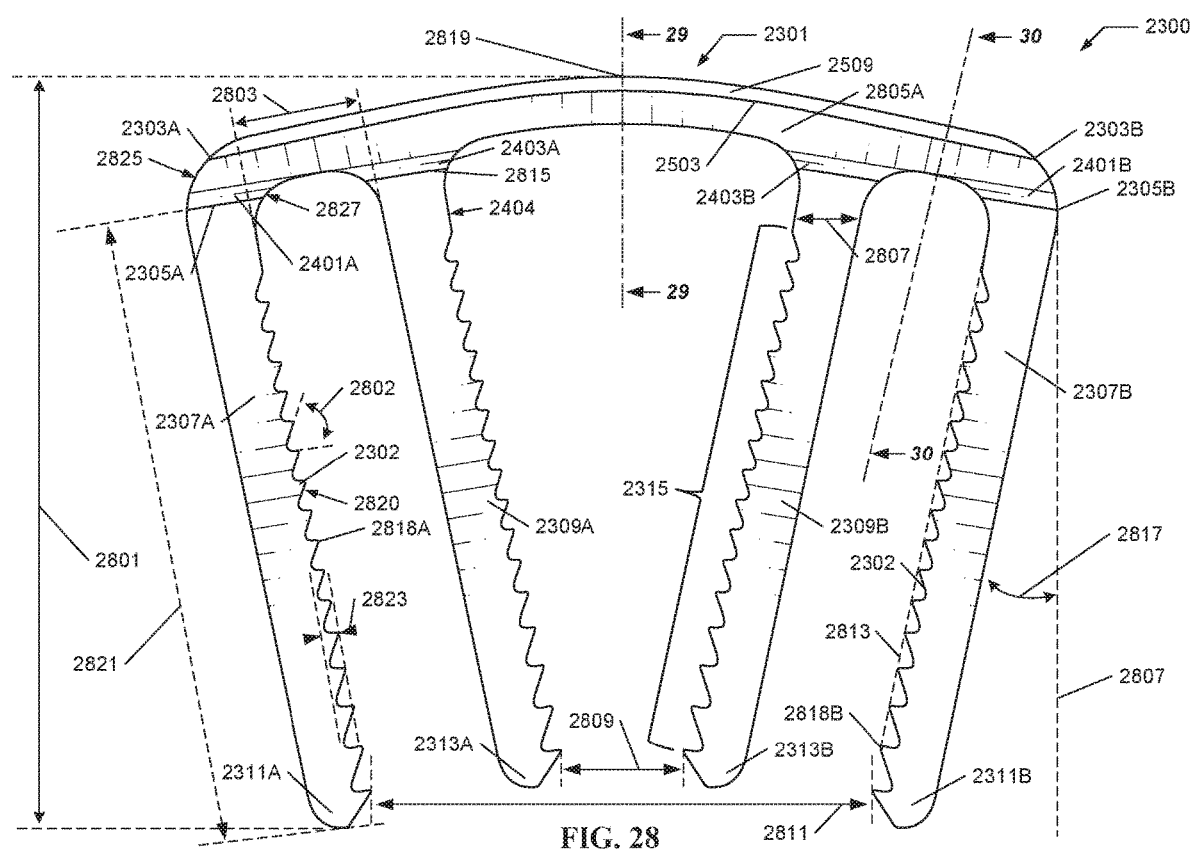
FIG. 28 is a front view of an exemplary low profile staple, according to one embodiment of the present disclosure.
Figure 29:
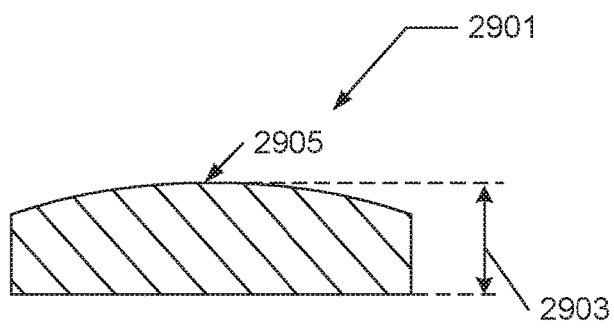
FIG. 29 is a cross-sectional view of an exemplary low profile staple, according to one embodiment of the present disclosure.
Figure 30:
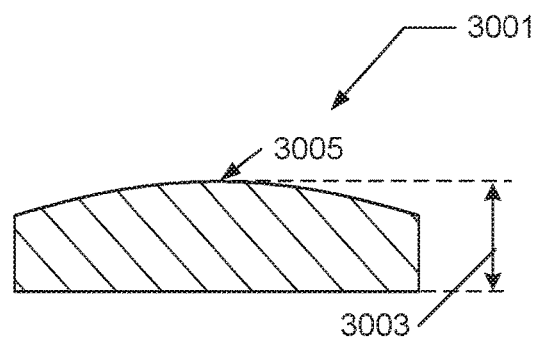
FIG. 30 is a cross-sectional view of an exemplary low profile staple, according to one embodiment of the present disclosure.

In one or more embodiments, the bridge 2301 has a first end 2303A and a second end 2303B and includes a substantially constant cross-section between the first end 2303A and the second end 2303B (as further discussed in relation to FIGS. 29-30). In at least one embodiment, the bridge 2301 is substantially smooth across a top surface (e.g., between the ends 2303A and 2303B). In some embodiments, the bridge 2301 includes one or more particular radii, which will be further discussed regarding FIG. 28. In at least one embodiment, portions of the bridge 2301 extend past the first and second ends 2303A, 2303B. In various embodiments, the extending portions include a top surface substantially coplanar with a top surface 2509 (FIG. 25) of the bridge 2301 and a bottom surface substantially coplanar or superior to a bottom surface 2602 (FIG. 26) of the bridge 2301. In one or more embodiments, the extending portions are for increasing ease of deforming staple 2300 between a first and a second position described herein by providing surfaces to which deforming forces are applied. According to one embodiment, the coplanar or superior position provides sufficient space for insertion of tools between the extending portions (and other features, as suitable) and a target region, such as a bone surface, thereby allowing for manipulation of the extending portions.

In various embodiments, the outer legs 2307A, 2307B and inner legs 2309A, 2309B are integrally formed with the bridge 2301. In some embodiments, the outer legs 2307A, 2307B may be generally straight from a proximal end 2305A, 2305B to a distal end 2311A, 2311B and may have a generally rectangular cross-section. In one or more embodiments, the inner legs 2309A, 2309B may be generally straight from a proximal end 2405A, 2405B (FIG. 24) to a distal end 2313A, 2313B and may have a generally rectangular cross-section. In at least one embodiment, the outer legs 2307A, 2307B and inner legs 2309A, 2309B may have any suitable shape (e.g. generally cylindrical, serpentine, obround, oval, tubular, etc.). According to one embodiment, the outer legs 2307A, 2307B are shaped differently from the inner legs 2309A, 2309B.

In one or more embodiments, the distal ends 2311A, 2311B and distal ends 2313A, 2313B include bone penetrating features, such as, for example, a wedge-like shape for easier insertion of a staple leg into tissue (e.g., bone). In various embodiments, the distal ends 2311A, 2311B and distal ends 2313A, 2313B include any suitable shape (e.g., points, rounded edges, blocked edges, etc.) or combination of suitable shapes.

In various embodiments, the staple 2300 includes one or more teeth sections 2315 cut into each of the outer legs 2307A, 2307B and/or inner legs 2309A, 2309B. According to one embodiment, the teeth section 2315 includes a plurality of teeth 2302. In some embodiments, the teeth section 2315 is located on an internal face of each of the outer legs 2307A, 2307B and inner legs 2309A, 2309B. In various embodiments, the teeth section 2315 extends along the entire length of the outer legs 2307A, 2307B and inner legs 2309A, 2309B. According to one embodiment, the teeth section 2315 may extend along a partial length of the outer legs 2307A, 2307B and inner legs 2309A, 2309B. In various embodiments, the teeth section 2315 may be wedge-shaped, curved, straight or any combination thereof. As will be understood, the staple 2300 may include two or more outer legs 2307A, 2307B (e.g., three, four, etc.) and/or two or more inner legs 2309A, 2309B. In one or more embodiments, a teeth section 2315 of each of the outer legs 2307A, 2307B and inner legs 2309A, 2309B may have a different (or the same) number of teeth 2302. In various embodiments, each of the outer legs 2307A, 2307B and inner legs 2309A, 2309B includes different sized or shaped teeth 2302 (e.g., for example, the inner legs 2309A, 2309B include teeth 2302 of a first shape and the outer legs 2307A, 2307B include teeth 2302 of a second shape).

In various embodiments, the staple 2300 demonstrates improved implanted torsional stability (e.g., compared to previous solutions), because the staple 2300 includes multiple points and surfaces of fixation, such as the teeth sections 2315 arranged on each of the outer legs 2307A, 2307B and inner legs 2309A, 2309B. In at least one embodiment, the curved and low profile geometry of the bridge 2301 contributes to the improved torsional stability of the bridge staple 2300 by reducing a risk of the bridge 2301 becoming caught on and/or disturbed by external surfaces. In one or more embodiments, the staple 2300 demonstrates increased and more sustained compression due to the inclusion of multiple pairs of legs (e.g., at least one pair of outer legs 2307A, 2307B and at least one pair of inner legs 2309A, 2309B) and multiple sets of fixating teeth. According to one embodiment, the increased prevalence of teeth and legs increases a total surface area of the staple 2300 that is in contact with tissue at an implantation site. In various embodiments, the increased total contracting surface area provides for more equal distribution of compressive forces and increases a pullout or pull-through force required to dislodge or remove the staple 2300, thereby advantageously improving the performance and translational stability of the staple 2300.

According to one embodiment, the staple 2300 demonstrates a torsional strength between about 2.0-3.0 N*m (newton-meters), thereby exceeding exemplary torsional strengths demonstrated in previous approaches. In one or more embodiments, the staple 2300 demonstrates a sustained compressive force of about 145.0-175.0 N, thereby exceeding compression strengths demonstrated in previous approaches. In various embodiments, in contrast to previous approaches, the staple 2300 demonstrates substantially consistent torsional strength and compressive force across a plurality of exemplary dimensions described herein. For example, an embodiment of the staple 2300 with a bridge length of about 26 mm and a leg length of about 20 mm may demonstrate substantially equal torsional strength and compressive force compared to a second embodiment of the staple 2300 with a bridge length of about 30 mm and a leg length of about 20 mm.

Figure 24:
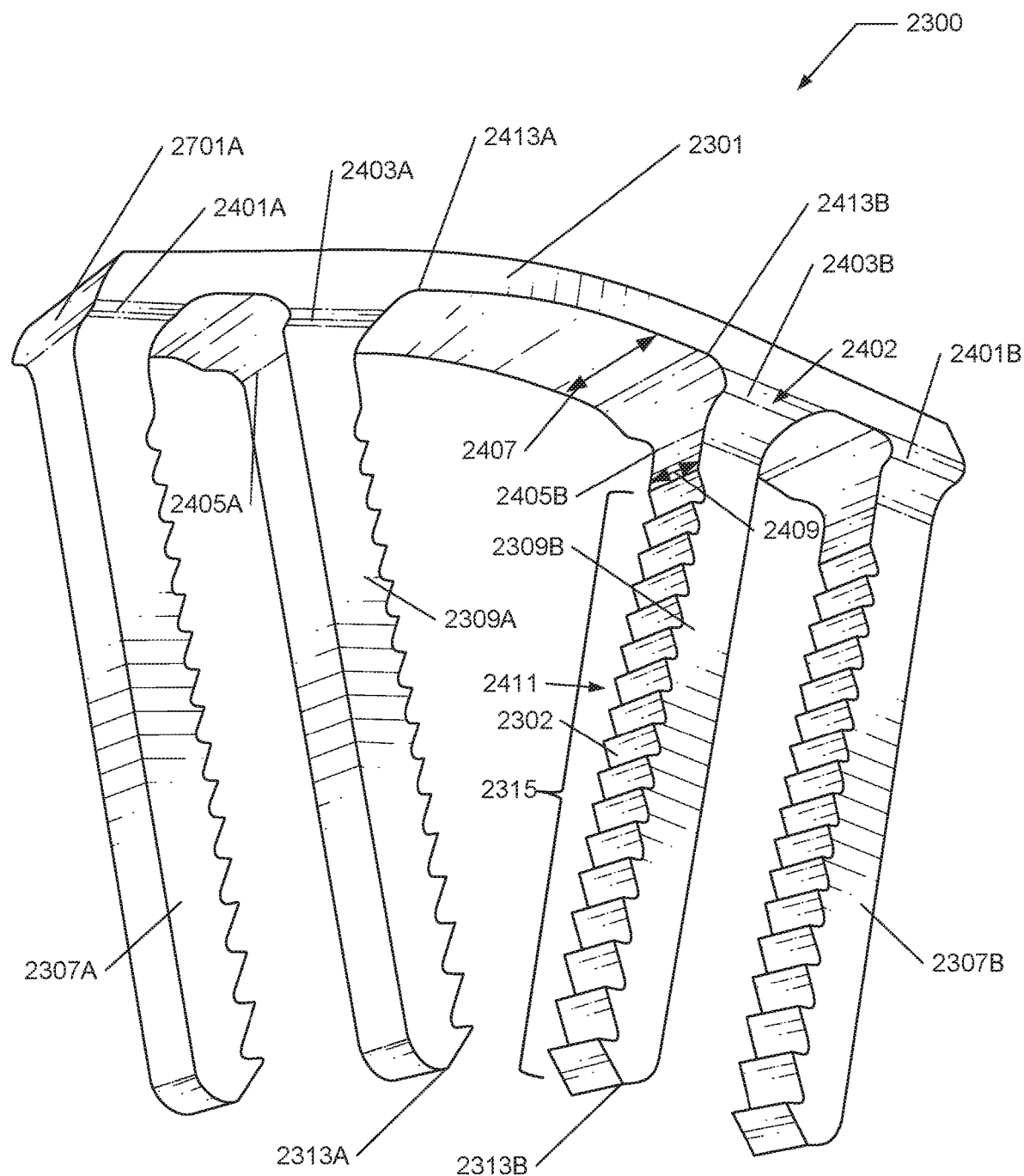
FIG. 24 is a perspective view of an exemplary low profile staple, according to one embodiment of the present disclosure.
Figure 25:
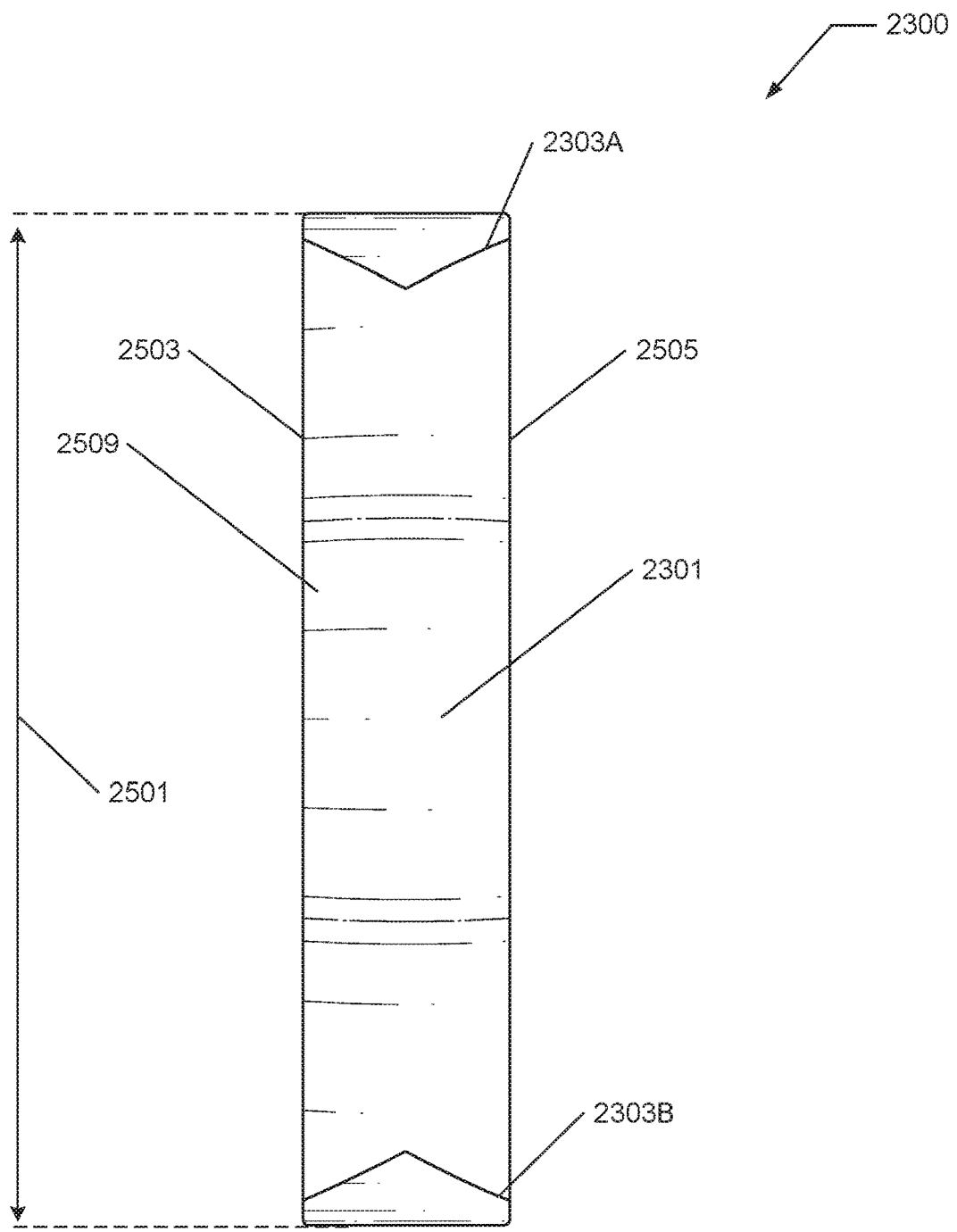
FIG. 25 is a top view of an exemplary low profile staple, according to one embodiment of the present disclosure.
Figure 26:
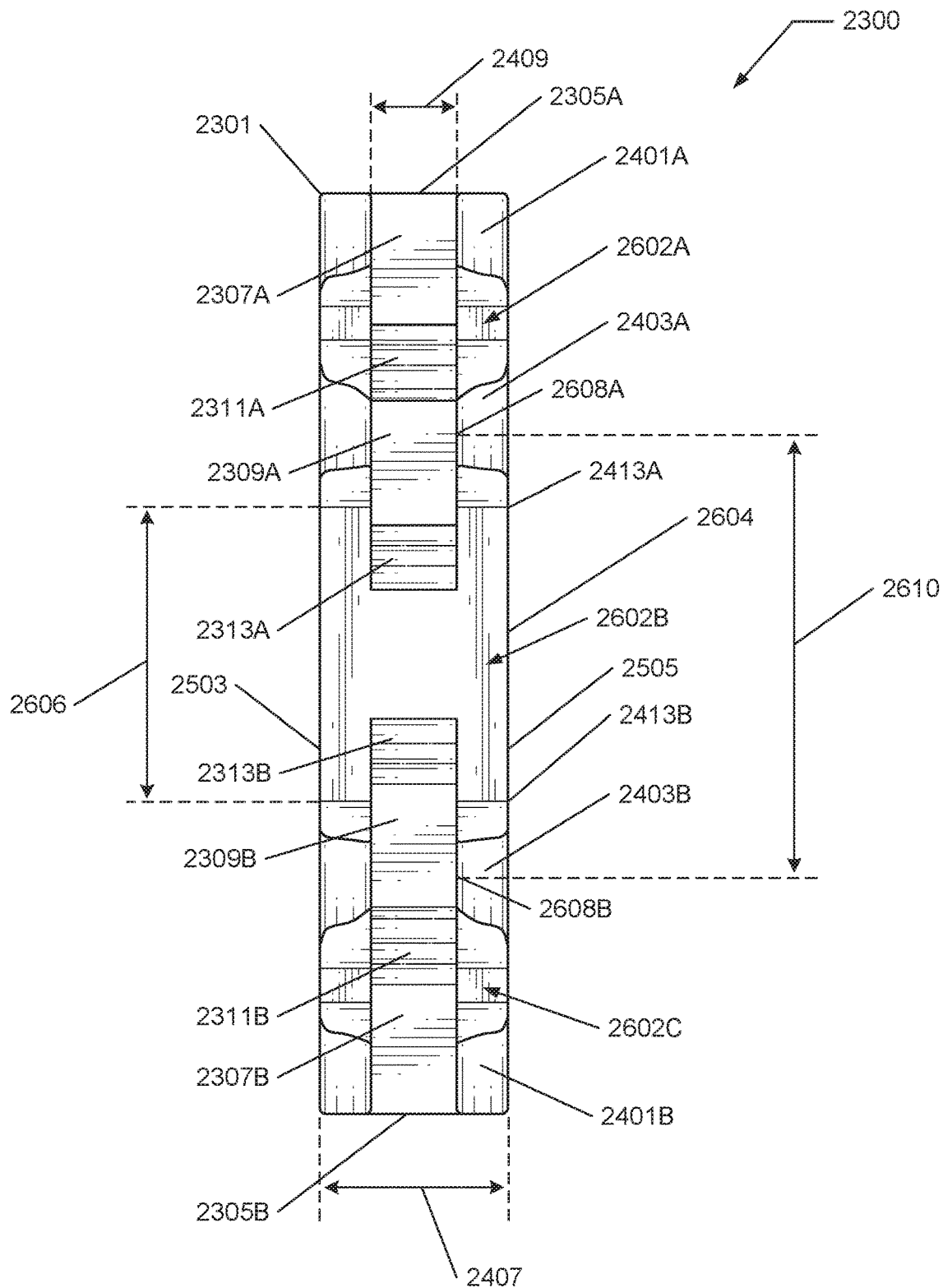
FIG. 26 is a bottom view of an exemplary low profile staple, according to one embodiment of the present disclosure.

In at least one embodiment, the substantially flat construction of the bridge 2301 (e.g., as provided via the substantially non-breaking top surface 2509 shown in FIG. 25) distributes strain substantially equally across the bridge 2301. According to one embodiment, the substantially even distribution of strain minimizes stress concentrations demonstrated in previous approaches and allows for greater durability of the staple 2300. In at least one embodiment, the bridge 2301 includes substantially curved or radial transitions between the outer legs 2307A, 2307B, inner legs 2309A, 2309B, outer shoulders 2401A, 2401B (FIG. 24), inner shoulders 2403A, 2403B (FIG. 24), and the bottom surface 2602 (FIG. 26). In at least one embodiment, the substantially curved construction of the transitions and the substantially flat construction of the bridge 2301 results in transfer of stress concentrations from undesirable regions, such as the connections between the staple bridge and staple legs, to more desirable regions, such as throughout the bridge 2301. In various embodiments, the movement of stress concentrations from undesirable to desirable regions advantageously reduces strain at the connections between the staple bridge and the staple legs, and, thus, reduces a likelihood of breakage between the staple bridge and one or more of the staple legs.

As described herein, the staple 2300 is deformable (e.g., bendable) between a first and a second position. Previous staples deform between first and second positions by undergoing bending substantially at the connections between the staple bridge and staple legs; however, this approach results in a large concentration of stress and, as a result, strain at the connections therebetween. The concentration of stress and strain at the transitions between the staple legs and staple bridge may reduce a durability of the staple and increase a likelihood of undesirable staple leg deformation or breakage. In at least one embodiment, the staple 2300 (and other staples described herein, such as the staple 3100) differ from previous approaches by undergoing bending substantially along the bridge 2301 (or bridge 3101), thereby moving stress and strain concentrations from the transitions between the bridge 2301 and staple legs to the bridge 2301 itself. Thus, in one or more embodiments, the staples described herein overcome deficits of previous staples by concentrating staple bending in the staple bridge and providing a substantially non-breaking bridge top surface to distribute strain substantially equally throughout the bridge and to preserve a low profile nature of the staple.

FIG. 24 shows a perspective view of the staple 2300. In various embodiments, the staple 2300 includes outer shoulders 2401A, 2401B and inner shoulders 2403A, 2403B. In at least one embodiment, each of the outer shoulders 2401A, 2401B and inner shoulders 2403A, 2403B transition from a depth 2407 of the bridge 2301 to a depth 2409 of the outer legs 2307A, 2307B and inner legs 2309A, 2309B. In one or more embodiments, the depth 2407 measures about 4.5-9.5 mm, about 4.5-5.0 mm, about 5.0-5.5 mm, about 5.0 mm, about 5.5-6.0 mm, about 6.0-6.5 mm, about 6.5-7.0 mm, about 7.0-7.5 mm, about 7.5-8.0 mm, about 8.0-8.5 mm, about 8.5-9.0 mm, or about 9.0-9.5 mm. In various embodiments, the depth 2409 measures about 1.0-4.0 mm, about 1.0-1.5 mm, about 1.5-2.0 mm, about 2.0-2.5 mm, about 2.5 mm, about 2.5-3.0 mm, about 3.0-3.5 mm, or about 3.5-4.0 mm.

Figure 27:
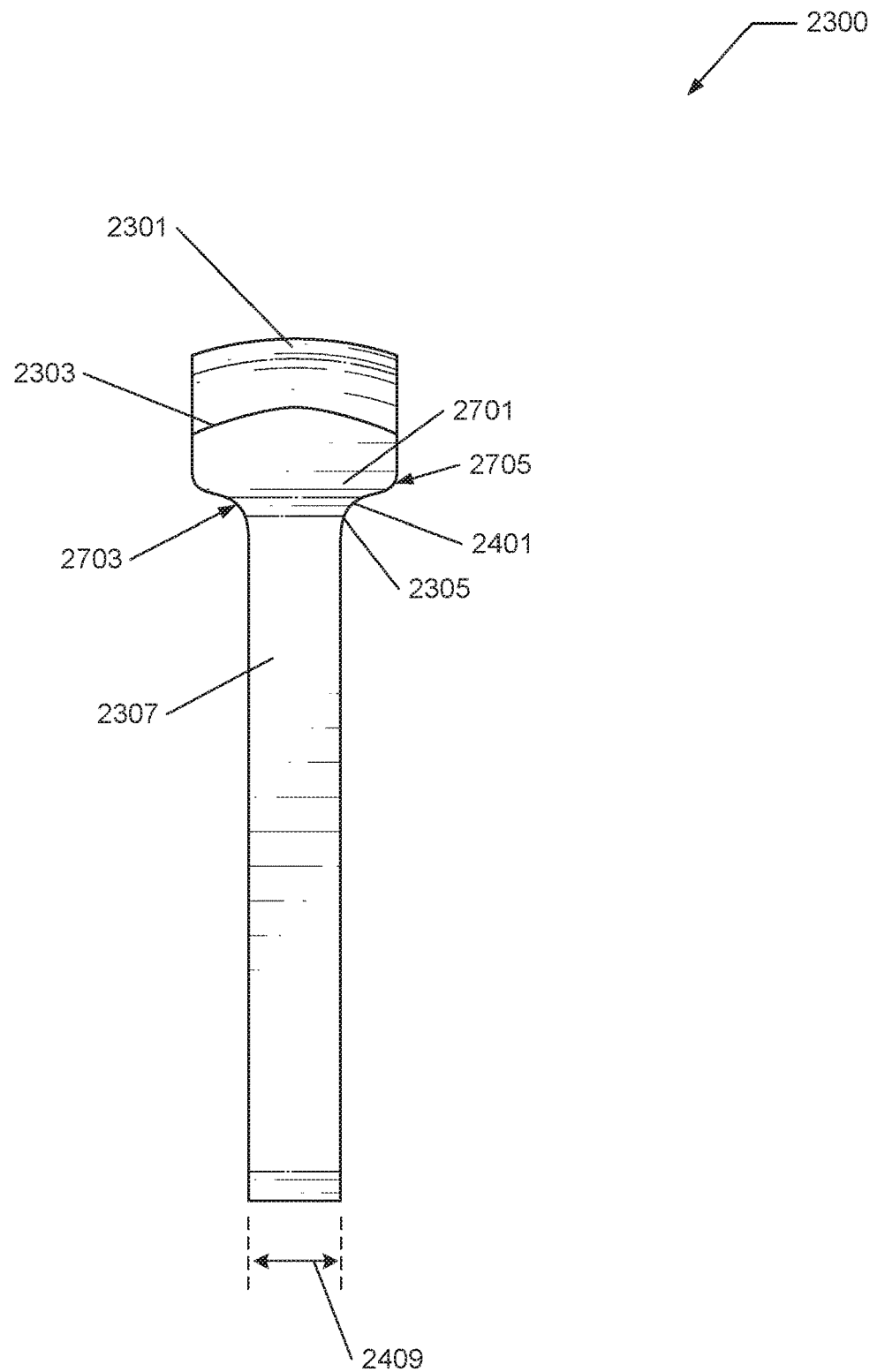
FIG. 27 is a side view of an exemplary low profile staple, according to one embodiment of the present disclosure.

According to one embodiment, the outer shoulders 2401A, 2401B and inner shoulders 2403A, 2403B include a substantially rectangular shape and/or include a shape substantially similar to a shape of the outer legs 2307A, 2307B and inner legs 2309A, 2309B. In one or more embodiments, the outer shoulders 2401A, 2401B and inner shoulders 2403A, 2403B include a radius 2703 (FIG. 27). In at least one embodiment, the outer shoulders 2401A, 2401B and inner shoulders 2403A, 2403B each include a substantially convex surface 2402 between the bridge 2301 and a corresponding outer leg 2307A, 2307B or inner leg 2309A, 2309B. According to one embodiment, the outer shoulders 2401A, 2401B and inner shoulders 2403A, 2403B each form a curved transition between the bridge 2301 and a corresponding outer leg 2307A, 2307B or inner leg 2309A, 2309B. In various embodiments, the curved transitions result in stress concentrations (e.g., that act as structural weak or failure points in previous approaches) at or throughout the bridge 2301. In other words, in at least one embodiment, the elimination of angular transitions between the bridge 2301 and outer legs 2307A, 2307B and inner legs 2309A, 2309B minimizes stress concentrations and, in combination with the flat construction of the bridge 2301, moves a substantial proportion of stress concentrations still present from the connections to the bridge 2301 where they are equally distributed throughout the length thereof.

In one or more embodiments, each of the outer legs 2307A, 2307B and inner legs 2309A, 2309B includes an inner surface 2411. According to one embodiment, the teeth section 2315 of each of each of the outer legs 2307A, 2307B and inner legs 2309A, 2309B is formed into the corresponding inner surface 2411. In various embodiments, each tooth 2302 of the teeth sections 2315 is integrally formed along the inner surface 2411 of the corresponding outer leg 2307 or inner leg 2309. In at least one embodiment, the inner surface 2411 is substantially smooth and flat (e.g., apart from teeth sections 2315 formed therein).

According to one embodiment, the inner shoulders 2403A, 2403B each include a radial point 2413A, 2413B. In one or more embodiments, the radial points 2413A, 2413B are innermost points of radii formed between the inner shoulders 2403A, 2403B and the bridge 2301. In various embodiments, the radial points 2413A, 2413B define a central portion of the bridge 2301 that includes a substantially continuous cross-section. In at least one embodiment, the inner legs 2309A, 2309B each include a mid-point 2608A, 2608B. According to one embodiment, a length 2610 between the midpoints 2608A, 2608B measures about 10-22 mm, about 10-12 mm, about 12-14 mm, about 14 mm, about 14-16 mm, about 16-18 mm, about 18 mm, about 18-20 mm, or about 20-22 mm.

FIG. 25 shows a top view of the staple 2300. According to one embodiment, the bridge 2301 includes a bridge length 2501 that measures about 25.0-32.0 mm, about 25.0-25.5 mm, about 25.5-26.0 mm, about 26.0-26.5 mm, about 26.92 mm, about 26.5-27.0 mm, about 27.0-27.5 mm, about 27.5-28.0 mm, about 28.0-28.5 mm, about 28.5-29.0 mm, about 29.0-29.5 mm, about 29.5-30.0 mm, about 30.0-30.5 mm, about 30.87 mm, about 30.5-31.0 mm, about 31.0-31.5 mm, or about 31.5-32.0 mm. In at least one embodiment, the bridge 2301 includes a low profile cross-section that is substantially constant throughout the entire bridge length 2501.

In various embodiments, the bridge 2301 includes a top surface 2509 formed between two edges 2503 and 2505. In at least one embodiment, the top surface 2509 is substantially smooth and non-breaking. According to one embodiment, the construction of the top surface 2509 (along with other features, such as arched features described herein)

result in concentration of stress throughout the bridge 2301, instead of, as in previous approaches, at the connections between the staple bridge and the staple legs. In at least one embodiment, the concentration and distribution of stress throughout the bridge 2301 offloads stress from the outer legs 2307A, 2307B and inner legs 2309A, 2309B to the bridge 2301, thereby reducing strain at connections therebetween and reducing a risk of leg deformation or breakage.

FIG. 26 shows a bottom view of the staple 2300. In one or more embodiments, the bridge 2301 includes a bottom surface 2602A, 2602B, 2602C that is substantially smooth. In one or more embodiments, the depth 2407 of the bridge 2301 is greater than the depth 2409 of the outer legs 2307A, 2307B and inner legs 2309A, 2309B. Accordingly, in various embodiments, the outer shoulders 2401A, 2401B and inner shoulders 2403A, 2403B transition from the depth 2407 to the depth 2409 in a direction from the bridge 2301 towards the distal ends 2311A, 2311B and distal ends 2313A, 2313B. In at least one embodiment, the outer shoulders 2401A, 2401B and inner shoulders 2403A, 2403B include a slope, arch, or other transition from each edge 2503, 2505 of the bridge 2301 to an edge of each of the outer legs 2307A, 2307B and inner legs 2309A, 2309B. According to one embodiment, the transition from the depth 2407 to the depth 2409 is substantially gradual and constant (e.g., a gradual slope or a constant radius arch). In one or more embodiments, the slope includes more than one slope of varying pitch or multiple arches of varying transition radii 2703 (FIG. 27).

In at least one embodiment, the bridge 2301 includes a central portion 2604 between radial points 2413A, 2413B. According to one embodiment, the central portion 2604 includes a length 2606 that measures about 6-20 mm, about 6-8 mm, about 8 mm, about 8-10 mm, about 8.6 mm, about 9 mm, about 10-12 mm, about 12 mm, about 12-14 mm, about 12.6 mm, about 13 mm, about 14-16 mm, about 16-18 mm, or about 18-20 mm. In various embodiments, the central portion 2604 includes a substantially continuous cross-section.

FIG. 27 shows a side view of the staple 2300. In various embodiments, the bridge 2301 is smooth and with a low-profile geometry that enables more curvature of the bridge 2301, which may create greater sustained compression when the staple 2300 is inserted into tissue (as further discussed herein).

In various embodiments, the outer leg 2307 is connected to a bottom portion of bridge 2301 at the corresponding proximal end 2305 of the outer leg 2307. In at least one embodiment, the staple 2300 includes transitional regions 2701 (see 2701B in FIG. 23, 2701A in FIG. 24) that transitions the ends 2303 to the proximal ends 2305. According to one embodiment, the transitional regions 2701 are sloped or curved. In one or more embodiments, the transitional regions 2701 include a radius 2703 that transitions the transitional regions 2701 between the ends 2303 and proximal ends 2305. In at least one embodiment, the radius 2703 transitions the outer shoulders 2401A, 2401B (shown as 2401 in FIG. 27) and inner shoulders 2403A, 2403B (not shown in FIG. 27) from the depth 2407 (FIG. 24) to the depth 2409 (FIG. 24). In various embodiments, the transition radius 2703 measures about 0.5-1.5 mm, about 0.25-0.5 mm, about 0.5-0.75 mm, about 0.75-1.0 mm, about 1.0 mm, about 1.0-1.25 mm, about 1.25-1.5 mm, or about 1.5-1.75 mm.

In at least one embodiment, the transitional regions 2701 include a radius 2705 that forms a curvature of the outer shoulders 2401A, 2401B (shown as 2401 in FIG. 27) and inner shoulders 2403A, 2403B. In one or more embodiments the radius 2705 measures about 0.25-1.0 mm, about 0.25-0.5 mm, about 0.5 mm, about 0.5-0.75 mm, or about 0.75-1.0 mm.

FIG. 28 shows a front view of the staple 2300. In one or more embodiments, the staple 2300 includes a height 2801. According to one embodiment, the height 2801 measures about 22.0-25.0 mm, about 22.0-22.5 mm, about 22.5-23.0 mm, about 23.31 mm, about 23.0-23.5 mm, about 23.51 mm, about 23.5-24.0 mm, about 24.0-24.5 mm, or about 24.5-25.0 mm.

In various embodiments, the bridge 2301 includes the top surface 2509 that connects to a side surface 2805A at the edge 2503 (e.g., on a front side of the staple 2300), and, while not shown in FIG. 28, connects to a side surface 2805B at the edge 2505 (FIG. 25). In at least one embodiment, the side surfaces 2805A, 2805B are parallel. In one or more embodiments the side surfaces 2805A, 2805B and are substantially smooth and vertically oriented.

In various embodiments, the outer legs 2307A, 2307B and inner legs 2309A, 2309B each include a leg width 2807 that measures about 1.0-3.0 mm, about 1.0-1.5 mm, about 1.5-2.0 mm, about 2.0 mm, about 2.0-2.5 mm, or about 2.5-3.0 mm.

According to one embodiment, towards the distal ends 2313A, 2313B, the inner leg 2309A is separated from the inner leg 2309B by a separation length 2809 that measures about 2.0-9.0 mm, about 2.0-2.5 mm, about 2.5-3.0 mm, about 3.0-3.5 mm, about 3.8 mm, about 3.5-4.0 mm, about 4.0-4.5 mm, about 4.5-5.0 mm, about 5.0-5.5 mm, about 5.5-6.0 mm, about 6.0-6.5 mm, about 6.5-7.0 mm, about 7.0-7.5 mm, about 7.7 mm, about 7.5-8.0 mm, about 8.0-8.5 mm, or about 8.5-9.0 mm.

According to one embodiment, towards the distal ends 2311A, 2311B, the outer leg 2307A is separated from the outer leg 2307B by a separation length 2811 that measures about 14.0-21.0 mm, about 14.0-14.5 mm, about 14.5-15.0 mm, about 15.0-15.5 mm, about 15.5 mm, about 15.5-16.0 mm, about 16.0-16.5 mm, about 16.5-17.0 mm, about 17.0-17.5 mm, about 17.5-18.0 mm, about 18.0-18.5 mm, about 18.5-19.0 mm, about 19.0-19.5 mm, about 19.5 mm, about 19.5-20.0 mm, about 20.0-20.5 mm, or about 20.5-21.0 mm.

In one or more embodiments, a separation length 2803 separates the outer leg 2307A from the inner leg 2309A and the outer leg 2307B from the inner leg 2309B. According to one embodiment, the separation length 2803 measures about 3.0-6.0 mm, about 3.0-3.5 mm, about 3.5-4.0 mm, about 4.0 mm, about 4.0-4.5 mm, about 4.5-5.0 mm, about 5.0-5.5 mm, or about 5.5-6.0 mm.

Reference lines 2807 and 2813 are shown in FIG. 28 to help explain how the teeth 2302 of the one or more teeth sections 2315 are created and to explain an angle 2817 of each of the outer legs 2307A, 2307B and inner legs 2309A, 2309B from vertical, respectively.

According to at least one embodiment, a plurality of the teeth 2302 are cut into the outer legs 2307A, 2307B and inner legs 2309A, 2309B. Stated another way, in a particular embodiment, ends 2818A, 2818B (e.g., sharpest points) of each tooth 2302 lie in the same plane as the inner surface of the corresponding outer leg 2307 or inner leg 2309. According to one embodiment, the plane of the inner surface of outer leg 2307B is shown approximately as the reference line 2813 and is representative of the planes of the outer leg 2307B and inner leg 2309B as can be appreciated.

In various embodiments, each teeth section 2315 includes a variable number of teeth 2302, the variable number being greater than, less than, or equal to about 4, 6, 8, 10, 14, 16, 18, or 20 (and including values therebetween). In one or more embodiments, the number of teeth 2302 included in the teeth section 2315 depends on a length 2821 of the outer legs 2307A, 2307B and inner legs 2309A, 2309B (e.g., a staple with longer legs may have more teeth 2302).

In one or more embodiments, the outer legs 2307A, 2307B and inner legs 2309A, 2309B include the length 2821 as measured, for example, from the proximal end 2305A of the outer leg 2307A to the distal end 2311A thereof or from a proximal end 2815 of the inner leg 2309A to the distal end 2313A thereof. In the embodiment shown, the outer legs 2307A, 2307B and inner legs 2309A, 2309B are the same length 2821. In various embodiments, the outer legs 2307A, 2307B and inner legs 2309A, 2309B have different lengths 2821, depending on the application of the staple 100. In one example, the outer legs 2307A, 2307B are of a first length 2821 and the inner legs 2309A, 2309B are of a second length 2821 measuring less than the first length 2821. In another example, the outer leg 2307A and inner leg 2309A are of a first length 2821 and the outer leg 2307B and inner leg 2309B are of a second length 2821 measuring less than the first length 2821.

According to one embodiment, the length 2821 measures about 15.0-23.0 mm, about 15.0-16.0 mm, about 16.0-17.0 mm, about 17.0-18.0 mm, about 18.0-19.0 mm, about 20.0 mm, about 19.0-20.0 mm, about 20.0-21.0 mm, about 21.0-22.0 mm, or about 22.0-23.0 mm.

In various embodiments, the outer legs 2307A, 2307B and inner legs 2309A, 2309B are at an acute angle 2817 of about 12.0-24.0 degrees from vertical (e.g., the angle between the inner legs 2309A and 2309B and between the outer legs 2307A and 2307B is about 24.0-48.0 degrees), as indicated by the reference line 2807. As will be understood from discussions herein, the angle 2817 from vertical may be, in at least one embodiment, substantially similar to an angle measured from a horizontal line from a highest point 2819 on the bridge 2301 (or, as in FIG. 36, the highest point 3608 on the bridge 3101) to the ends 2303A, 2303B of the bridge 2301 (or ends 3103A, 3103B of the bridge 3101).

FIG. 28 shows a section line, 29, which indicates a cross-section 2901 of the bridge 2301 shown in FIG. 29. FIG. 30 shows a section line, 30, which indicates a cross-section 3001 of the bridge 2301 shown in FIG. 30. As shown, the section line 29 passes through an approximate midpoint of the bridge 2301 and the section line 30 passes through an approximate midpoint on the bridge 2301 between the inner leg 2309B and the outer leg 2307B. As further discussed herein, the bridge 2301, in various embodiments, includes a constant cross-section. As such, it should be understood that, in various embodiments, the cross-sections 2901 and 3001 indicated by the section lines 29 and 30 represent any cross-section of the bridge 2301. The cross-sections 2901 and 3001 are further discussed below in relation to FIG. 29 and FIG. 30 respectively.

In at least one embodiment, each tooth 2302 includes a tooth angle 2802 that generally refers to an angle between the end 2818A and a sloped surface 2820 of the tooth 2302. According to one embodiment, the tooth angle 2802 measures about 45.0-60.0 degrees, about 45.0 degrees, about 45.0-48.0 degrees, about 44.0-48.0 degrees, about 48.0-52.0 degrees, about 52.0-56.0 degrees, about 56.0-60.0 degrees, or about 60.0 degrees. In one or more embodiments, all of the teeth 2302 include the tooth angle 2802 of the same magnitude. In various embodiments, a tooth 2302 at the distal end 2311A of the outer leg 2307A (or other distal end of another leg described herein) is at a tooth angle 2802 other than 60 degrees, such as for example, 45 degrees. In one or more embodiments, each tooth 2302 may include any suitable angle or angles, including but not limited to about 20.0-85.0 degrees. According to one embodiment, the tooth angle 2802 of each respective tooth 2302 in a teeth section 2315 (FIG. 23) decreases towards the distal end 2311A.

In one or more embodiments, each tooth 2302 includes a width 2823 that measures greater than, less than, or equal to about 0.01-1.00 mm, 0.36 mm, 0.41 mm, 0.46 mm, 0.51 mm, 0.56 mm, or about 0.58 mm. According to one embodiment, the width 2823 of each respective tooth 2302 in a teeth section 2315 (FIG. 23) increases towards the distal end 2311A. For example, a tooth 2302 at a bottom of a teeth section 2315 (e.g., at the distal end 2311A) includes a width 2823 of about 0.58 mm and a second tooth 2302 at a top of the teeth section 2315 (e.g., towards the proximal end 2305A) includes a width 2823 of about 0.36 mm. In the same example, a plurality of the teeth 2302 located toward the bottom of the teeth section 2315 are larger (e.g., wider) than a plurality of the teeth 2302 located toward the top of the teeth section 2315.

As will be understood from discussions herein, all of the teeth 2302 of the staple 100 may be substantially the same shape, depth, etc. In various embodiments, the number of teeth 2302, width 2823, angle 3001, etc. may vary along the length of a connected leg (e.g., outer leg 2307A or 2307B, or inner leg 2309A or 2309B).

In one or more embodiments, the staple 2300 includes an outer radius 2825 defining an external curvature between the top surface 2509 of the bridge 2301 and outer legs 2307A, 2307B. According to one embodiment, the outer radius 2825 measures about 1.0-4.0 mm, about 1.0-1.5 mm, about 1.5-2.0 mm, about 2.0-2.5 mm, about 2.5 mm, about 2.5-3.0 mm, about 3.0-3.5 mm, or about 3.5-4.0 mm. In various embodiments, the staple 2300 includes an inner radius 2827 defining an internal curvature between the bottom surface 2602 (FIG. 26) of the bridge 2301 and outer legs 2307A, 2307B and inner legs 2309A, 2309B. In at least one embodiment, the inner radius 2827 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm.

FIG. 29 shows a cross-sectional view of the bridge 2301 (FIG. 23). According to one embodiment, the cross-section 2901 shown in FIG. 29 is a cross-section taken from a midpoint of the bridge 2301 as indicated in section line 29 of FIG. 28. In at least one embodiment, the cross-section 2901 is representative of a continuous cross-section of a central portion of the bridge 2301 (e.g., central portion 2604 shown in FIG. 26).

In various embodiments, the cross-section 2901 includes a height 2903 representative of a total height of the bridge 2301. According to one embodiment, the height 2903 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm. According to one embodiment, the height 2903 and depth 2407 of the bridge 2301 are selected such that the bridge 2301 demonstrates a substantially constant moment of inertia, (regardless of a deformation state of the staple 2300) that is located at a central region of the bridge 2301. In at least one embodiment, the substantially constant moment of inertia allows the staple 2300 to demonstrate substantially constant mechanical properties (e.g., bending properties) regardless of a current deformation state. According to one embodiment, the substantially constant mechanical properties provide for continuous concentration and equal distribution of stresses at the bridge 2301.

In various embodiments, the cross-section 2901 includes a continuous radius 2905 that defines a curvature of the top surface 2509 (shown in FIG. 25). In at least one embodiment, the radius 2905 measures about 2.0-9.0 mm, about 2.0-2.5 mm, about 2.5-3.0 mm, about 3.0-3.5 mm, about 3.8 mm, about 3.5-4.0 mm, about 4.0-4.5 mm, about 4.5-5.0 mm, about 5.0-5.5 mm, about 5.5-6.0 mm, about 6.0-6.5 mm, about 6.5-7.0 mm, about 7.0-7.5 mm, about 7.7 mm, about 7.5-8.0 mm, about 8.0-8.5 mm, about 8.4 mm, or about 8.5-9.0 mm.

FIG. 30 shows a cross-sectional view of the bridge 2301 (FIG. 23). According to one embodiment, the cross-section 3001 shown in FIG. 30 is a cross-section taken from a midpoint of the bridge 2301 as indicated in section line 30 of FIG. 28.

In various embodiments, the cross-section 3001 includes a height 3003 representative of a total height of the bridge 2301, and is substantially identical to the height 2903. According to one embodiment, the height 3003 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm.

In various embodiments, the cross-section 3001 includes a continuous radius 3005 that defines the curvature of the top surface 2509 (shown in FIG. 25) and is substantially identical to the radius 2905 (FIG. 29). In at least one embodiment, the radius 3005 measures about 2.0-9.0 mm, about 2.0-2.5 mm, about 2.5-3.0 mm, about 3.0-3.5 mm, about 3.8 mm, about 3.5-4.0 mm, about 4.0-4.5 mm, about 4.5-5.0 mm, about 5.0-5.5 mm, about 5.5-6.0 mm, about 6.0-6.5 mm, about 6.5-7.0 mm, about 7.0-7.5 mm, about 7.7 mm, about 7.5-8.0 mm, about 8.0-8.5 mm, about 8.4 mm, or about 8.5-9.0 mm.

Figure 31:
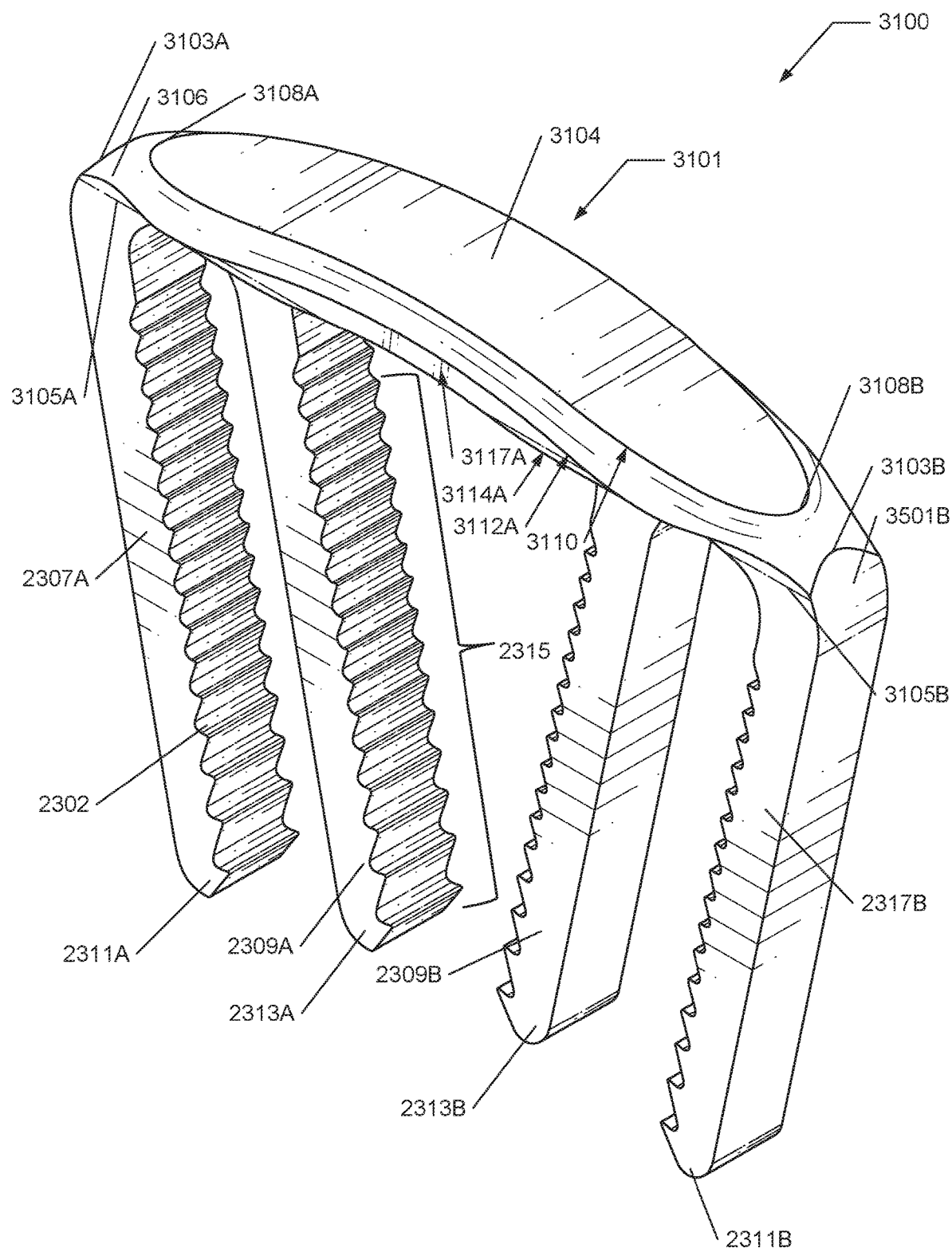
FIG. 31 is a perspective view of an exemplary low profile staple, according to one embodiment of the present disclosure.

FIG. 31 shows a perspective view of an exemplary staple 3100. In various embodiments, the staple 3100 includes a bridge 3101, at least two outer legs 2307A, 2307B, and at least two inner legs 2309A, 2309B. According to one embodiment, the staple 3100 size (bridge 3101 length×outer leg 2307 length×inner leg 2309 length) may be greater than, less than or equal to about 26.0 mm×20.0 mm×20.0 mm, 30.0 mm×20.0 mm×20.0 mm, 26.93 mm×23.32 mm×23.32 mm, or 30.88 mm×23.51 mm×23.51 mm.

In one or more embodiments, the bridge 3101 has a first end 3103A and a second end 3103B opposite the first end 3103A. In various embodiments, the bridge 3101 includes a first intermediary end 3108A and a second intermediary end 3108B opposite the first intermediary end 3108A. In at least one embodiment, the bridge 3101 includes a top surface 3104 between the first and second intermediary ends 3108A, 3108B. According to one embodiment, the top surface 3104 tapers in depth towards each intermediary end 3108A, 3108B. As further discussed herein, in one or more embodiments, the bridge 3101 includes a transition region 3106 that includes the area of bridge 3101 between the first intermediary end 3108A and first end 3103A and between the second intermediary end 3108B and second end 3103B. In alternate embodiments, the bridge 3101 excludes the transition region 3106 and, thus, the top surface 3104 extends between the first end 3103A and second end 3103B and extends between the edges 3112A, 3112B.

In at least one embodiment, portions of the bridge 3101 extend past the first and second ends 3103A, 3103B. In various embodiments, the extending portions include a top surface substantially coplanar with the top surface 3104 and a bottom surface substantially coplanar or superior to a bottom surface 3402 (FIG. 34) of the bridge 3101. In one or more embodiments, the extending portions are for increasing ease of deforming staple 3300 between a first and a second position described herein by providing surfaces to which deforming forces are applied.

Figure 32:
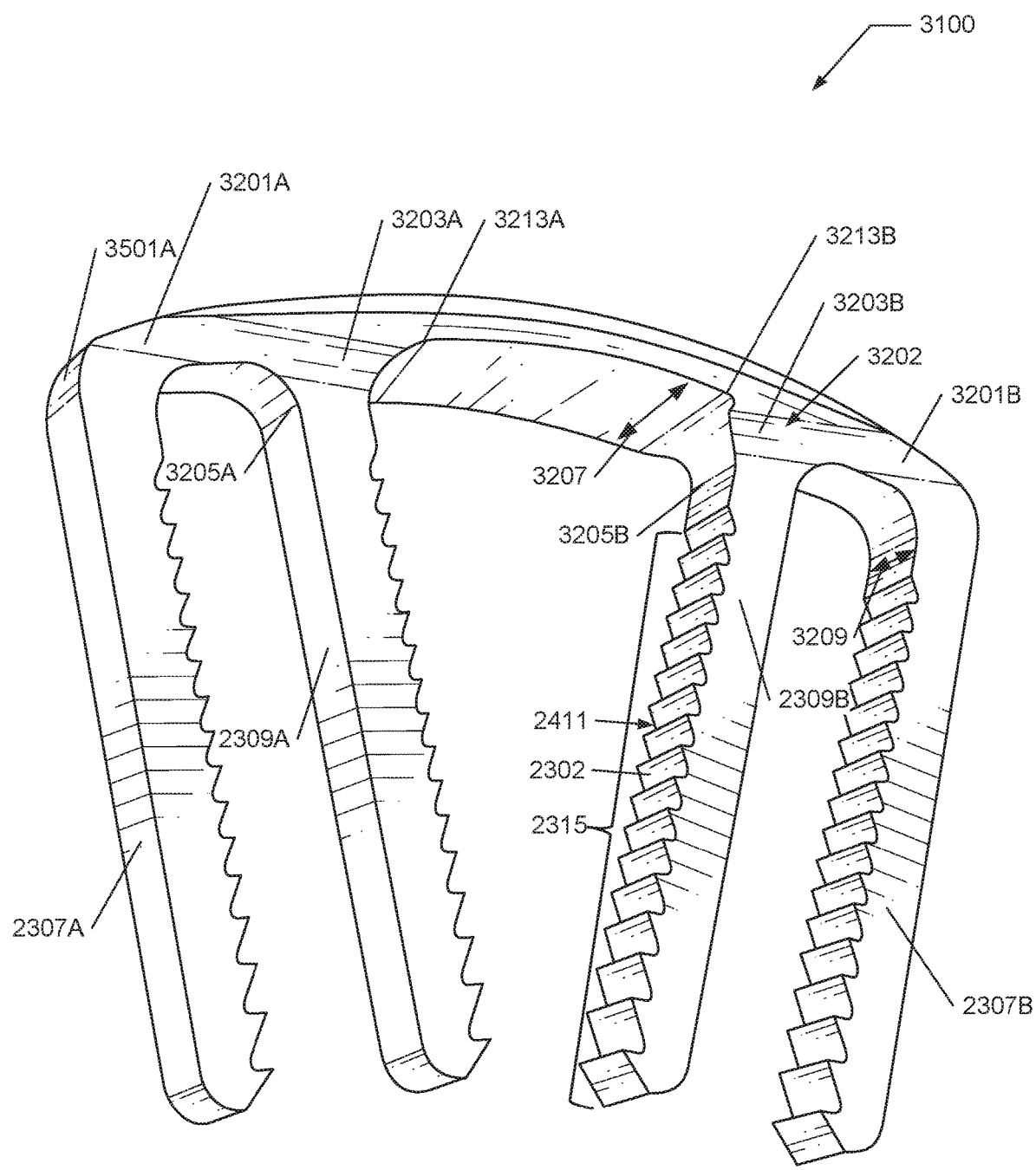
FIG. 32 is a perspective view of an exemplary low profile staple, according to one embodiment of the present disclosure.
Figure 33:
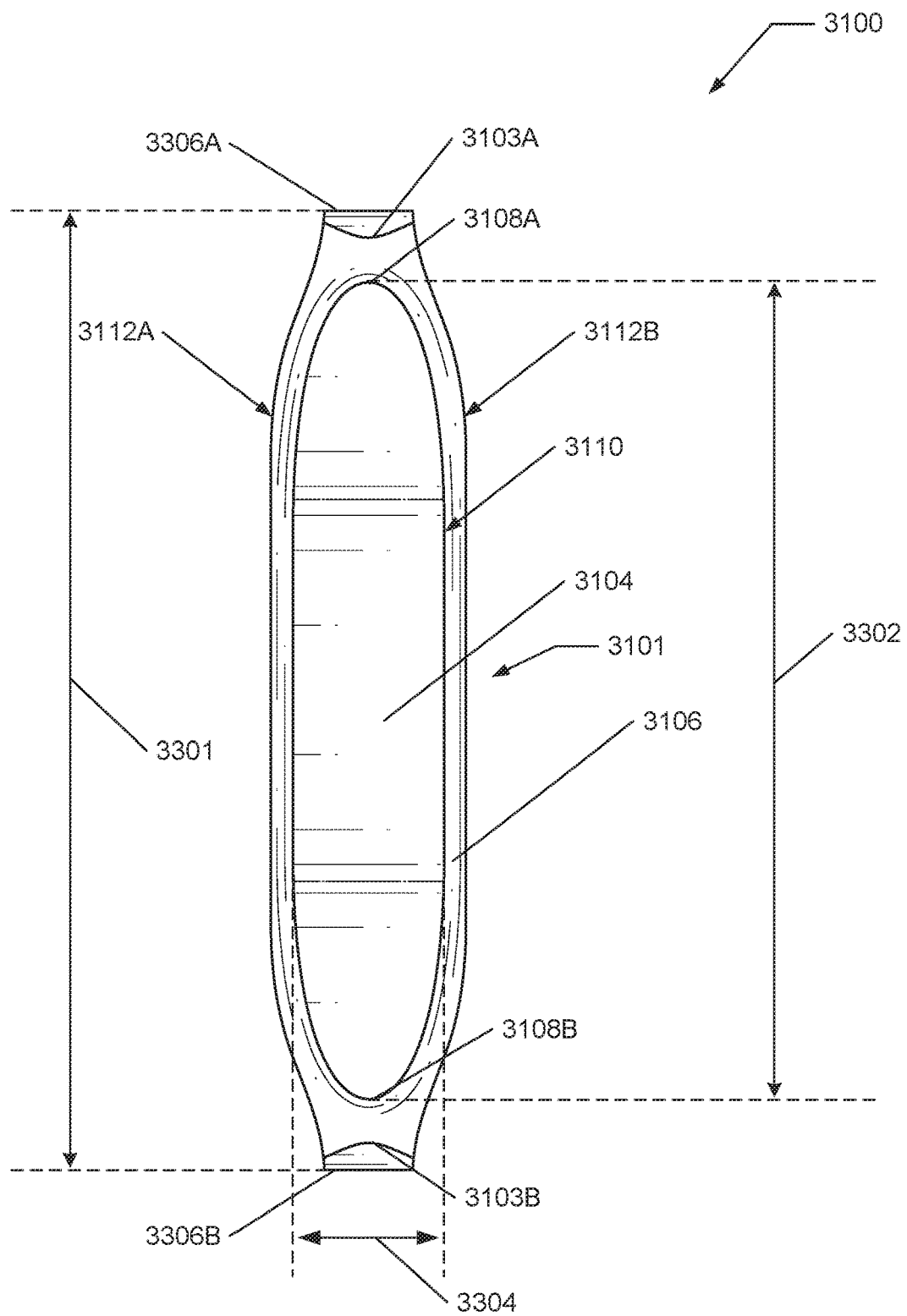
FIG. 33 is a top view of an exemplary low profile staple, according to one embodiment of the present disclosure.

In one or more embodiments, the bridge 3101 includes an edge 3110 that defines a transition from the top surface 3104 to the transition region 3106. In various embodiments, the transition region 3106 is curved between the edge 3110 and edges 3112A, 3112B. In at least one embodiment, the edge 3110 is substantially rounded or chamfered to provide a low profile, curved transition between the top surface 3104 and the transition region 3106. According to one embodiment, the bridge 3101 includes the edge 3112A that defines a transition from the transition region 3106 to a side surface 3117A. In at least one embodiment, as shown in FIG. 33, the bridge 3101 includes the edge 3112B that defines a transition from the transition region 3106 to a side surface 3117B (e.g., that is parallel to and opposite the side surface 3117A). In one or more embodiments, the edges 3112A, 3112B are substantially rounded or chamfered to provide a low profile, curved transition between the transition region 3106 and side surfaces 3117A, 3117B. In various embodiments, the side surfaces 3117A, 3117B include edges 3114A, 3114B (see FIG. 33) that define a transition between the side surfaces 3117A, 3117B and inner shoulders 3203A, 3203B (FIG. 32). In at least one embodiment, the edges 3114A, 3114B are substantially curved or rounded to contribute to the low profile of the staple 3100. In at least one embodiment, the side surfaces 3117A, 3117B are substantially smooth and vertically oriented.

Figure 34:
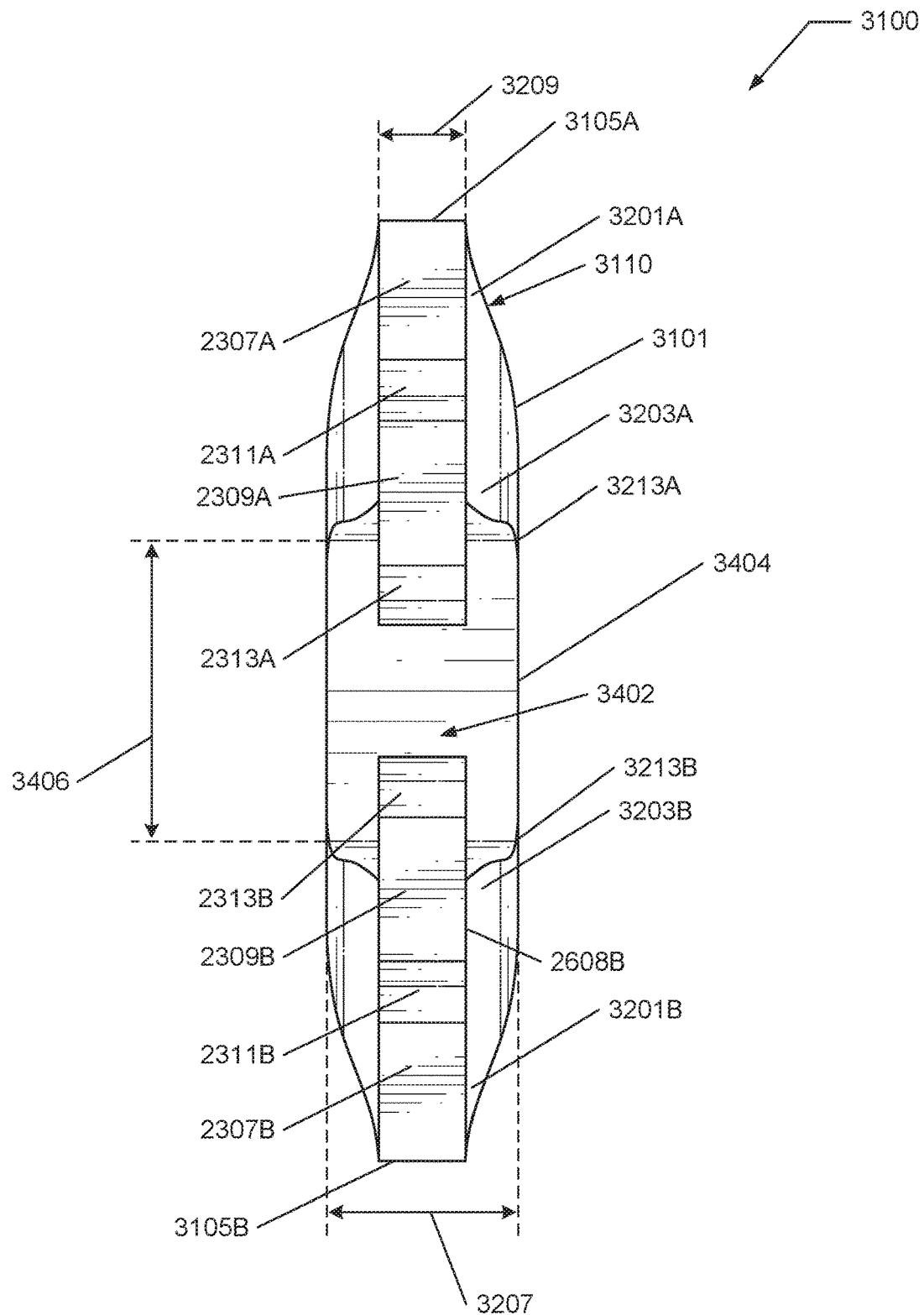
FIG. 34 is a bottom view of an exemplary low profile staple, according to one embodiment of the present disclosure.

In at least one embodiment, the substantially flat construction of the bridge 3101 (e.g., as provided via the substantially non-breaking top surface 3104) distributes strain substantially equally across the bridge 3101. According to one embodiment, the substantially even distribution of strain minimizes stress concentrations demonstrated in previous approaches and allows for greater durability of the staple 3100. In at least one embodiment, the bridge 3101 includes substantially curved or radial transitions between the outer legs 2307A, 2307B, inner legs 2309A, 2309B, outer shoulders 3201A, 3201B (FIG. 32), inner shoulders 3203A, 3203B (FIG. 32), and the bottom surface 3402 (FIG. 34). In at least one embodiment, the substantially curved construction of the transitions and the substantially flat construction of the bridge 3101 results in transfer of stress concentrations from undesirable regions, such as the connections between the staple bridge and staple legs, to desirable regions, such as throughout the bridge 3101. In various embodiments, the movement of stress concentrations from undesirable to desirable regions advantageously reduces strain at the connections between the staple bridge and the staple legs, and, thus, reduces a likelihood of breakage between the staple bridge and one or more of the staple legs.

According to one embodiment, in an inner section of the bridge 3101, between the inner legs 2309A and 2309B, the bridge 3101 includes a substantially constant cross-section. In at least one embodiment, at least partially due to the substantially constant cross-section, the inner section of the bridge 3101 experiences proportionally greater stresses than outer sections of the bridge 3101 between the outer leg 2307A and inner leg 2309A and between the outer leg 2307B and inner leg 2309B. In various embodiments, the concentration of stresses to the inner section of the bridge 3101 provides greater stability to the staple 3100. For example, due to a reduction of stress concentrations at connections between the legs 2309A, 2309B and the bridge 3101, a likelihood of breakage or other undesired deformations of the staple components may be reduced.

In one or more embodiments, the outer leg 2307A and inner leg 2309A may remain in a relatively fixed position relative to each other during and following deformation of the staple 3100 (e.g., as may also occur for the outer leg 2307B and inner leg 2309B). According to one embodiment, at least partially due to the relatively fixed position of the legs of each outer section, the deformation of the staple 3100 is relatively confined to the inner section of the bridge 3101 and, therefore, the introduction of deformation forces to the outer sections is minimized (e.g., though some degree of deformation may occur). In various embodiments, the outer sections of the bridge 3101 may be subjected to less physiological loading between bony fragments as compared to physiological loading experienced at the inner section of the bridge 3101. For example, following implantation of the staple 3100 into a first and a second bony fragment, the outer leg 2307A and inner leg 2309B are located in the first bony fragment and the outer leg 2307B and inner leg 2309B are located in the second bony fragment. In the same example, a substantial magnitude of bending forces experienced by the staple 3100, due to physiological loads, is translated to the inner section of the bridge 3101 because the legs of each outer section may not bend significantly relative to each other. In some embodiments, the bridge 3101 includes one or more particular radii, which will be further discussed regarding FIG. 36. In various embodiments, the outer legs 2307A, 2307B and inner legs 2309A, 2309B are integrally formed with the bridge 3101. In various embodiments, the staple 3100 includes one or more teeth sections 2315 cut into each of the outer legs 2307A, 2307B and inner legs 2309A, 2309B. According to one embodiment, the teeth sections 2315 includes a plurality of teeth 2302.

In various embodiments, the staple 3100 demonstrates improved implanted torsional stability (e.g., compared to previous solutions) in a manner substantially similar to the staple 2300 (FIG. 23). According to one embodiment, the staple 3100 demonstrates mechanical performance properties substantially similar to mechanical performance properties demonstrated by the staple 2300 described herein. In one or more embodiments, the staple 3100 includes an overall low-profile shape such that, upon implantation at a target site, the staple 3100 demonstrates a reduced likelihood of being caught on or disturbed by external surfaces. For example, the low-profile shape may reduce a likelihood of additional corrective fixtures, such as braces, and other instrumentation disturbing an implanted position of the staple 3100 in instances of contact.

FIG. 32 shows a perspective view of the staple 3100. In various embodiments, the staple 3100 includes outer shoulders 3201A, 3201B and inner shoulders 3203A, 3203B. In at least one embodiment, each of the outer shoulders 3201A, 3201B and inner shoulders 3203A, 3203B transitions from a depth 3207 of the bridge 3101 to a depth 3209 of the outer legs 2307A, 2307B and inner legs 2309A, 2309B. In one or more embodiments, the depth 3207 measures about 4.5-7.5 mm, about 4.5-5.0 mm, about 5.0-5.5 mm, about 5.0 mm, about 5.5-6.0 mm, about 6.5-7.0 mm, or about 7.0-7.5 mm. In various embodiments, the depth 3209 measures about 1.0-4.0 mm, about 1.0-1.5 mm, about 1.5-2.0 mm, about 2.0-2.5 mm, about 2.5 mm, about 2.5-3.0 mm, about 3.0-3.5 mm, or about 3.5-4.0 mm.

Figure 35:
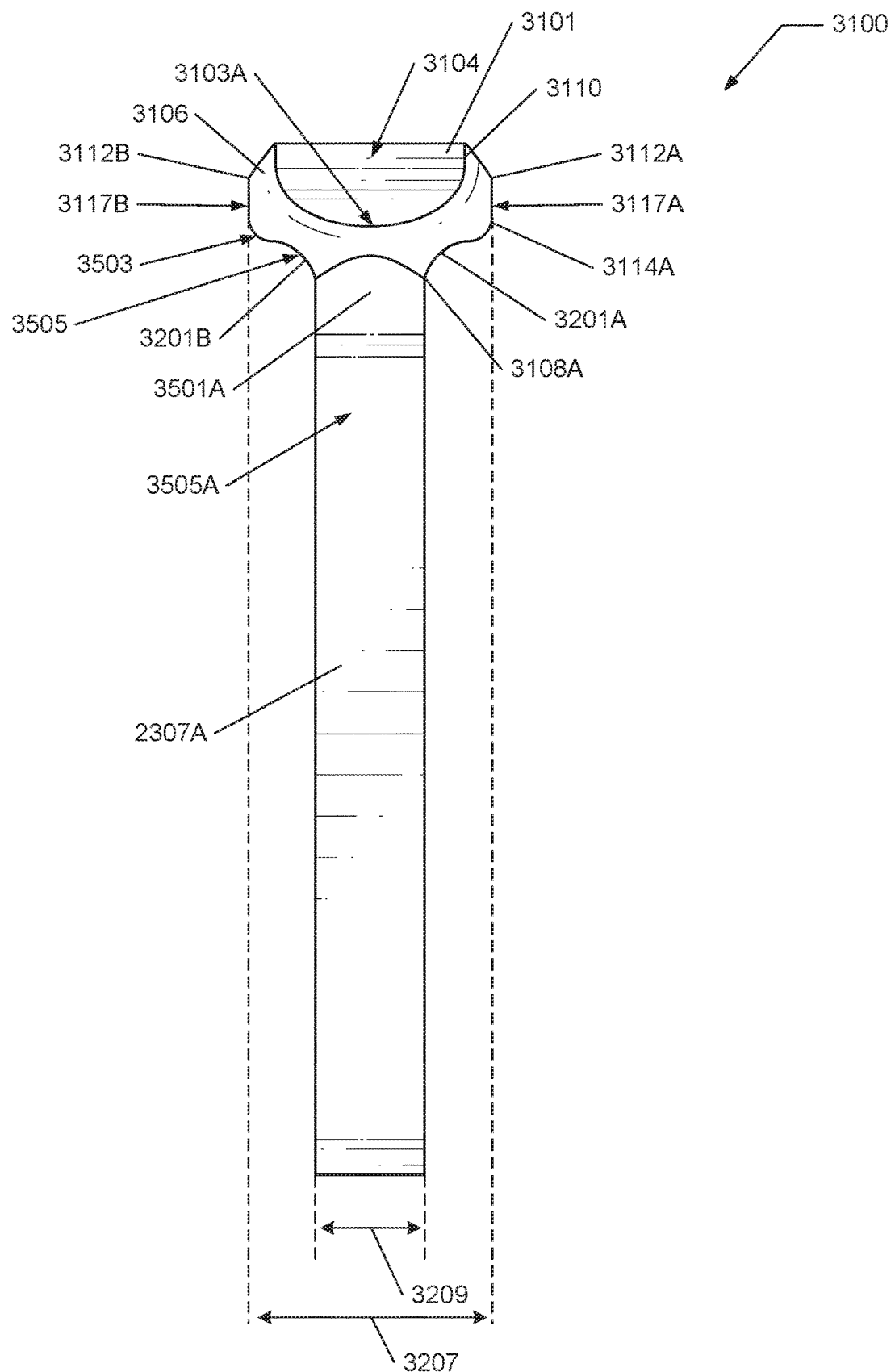
FIG. 35 is a side view of an exemplary low profile staple, according to one embodiment of the present disclosure.

According to one embodiment, the outer shoulders 3201A, 3201B and inner shoulders 3203A, 3203B include a substantially rectangular shape and/or include a shape substantially similar to a shape of the outer legs 2307A, 2307B and inner legs 2309A, 2309B. In one or more embodiments, the outer shoulders 3201A, 3201B and inner shoulders 3203A, 3203B include a radius 3503 (FIG. 35). In at least one embodiment, the outer shoulders 3201A, 3201B and inner shoulders 3203A, 3203B each include a substantially convex surface 3202 between the bridge 3101 and a corresponding outer leg 2307A, 2307B or inner leg 2309A, 2309B. According to one embodiment, the outer shoulders 3201A, 3201B and inner shoulders 3203A, 3203B each form a substantially curved or radial transition between the bridge 3101 and a corresponding outer leg 2307A, 2307B or inner leg 2309A, 2309B. In various embodiments, the curved transitions result in movement of stress concentrations (e.g., that act as structural weak or failure points in previous approaches) from connections between the bridge 3101 and the staple legs to the bridge 2301. In other words, in at least one embodiment, the elimination of angular transitions between the bridge 3101 and outer legs 2307A, 2307B and inner legs 2309A, 2309B minimizes stress concentrations and, in combination with the flat construction of the bridge 3101, moves a substantial proportion of stress concentrations still present from the connections to the bridge 3101 where they are equally distributed throughout the length thereof.

According to one embodiment, the inner shoulders 3203A, 3203B each include a radial point 3213A, 3213B. In one or more embodiments, the radial points 3213A, 3213B are innermost points of radii formed between the inner shoulders 3203A, 3203B and the bridge 3101. In various embodiments, the radial points 3213A, 3213B define a central portion of the bridge 3101 that includes a substantially continuous cross-section.

FIG. 33 shows a top view of the staple 3100. According to one embodiment, the staple 3100 includes a staple length 3301 defining a length of the staple 3100 between ends 3306A, 3306B. According to one embodiment, the staple length 3301 measures about 25.0-32.0 mm, about 25.0-25.5 mm, about 25.5-26.0 mm, about 26.0-26.5 mm, about 26.93 mm, about 26.5-27.0 mm, about 27.0-27.5 mm, about 27.5-28.0 mm, about 28.0-28.5 mm, about 28.5-29.0 mm, about 29.0-29.5 mm, about 29.5-30.0 mm, about 30.0-30.5 mm, about 30.88 mm, about 30.5-31.0 mm, about 31.0-31.5 mm, or about 31.5-32.0 mm.

In one or more embodiments, the top surface 3104 includes a length 3302 that measures about 15.0-25.0 mm, about 15.0-16.0 mm, about 16.0-17.0 mm, about 17.0-18.0 mm, about 18.0-19.0 mm, about 19.0-20.0 mm, about 20.0-21.0 mm, about 21.0-22.0 mm, about 22.0-23.0 mm, about 23.0 mm, about 23.0-24.0 mm, about 24.0-25.0 mm, about 25.0-26.0 mm, about 26.0-27.0 mm, about 26.9 mm, or about 27.0-28.0 mm. In at least one embodiment, the top surface 3104 includes a maximum depth 3304 that represents a depth of the top surface 3104 prior to the top surface 3104 tapering to the intermediary ends 3108A, 3108B. According to one embodiment, the maximum depth 3304 measures about 3.0-5.0 mm, about 3.0-3.5 mm, about 3.5-4.0 mm, about 4.0-4.5 mm, about 4.2 mm, about 4.5-5.0 mm, or about 5.0-5.5 mm.

In various embodiments, the transition region 3106 includes a curved (e.g., concave) surface between the edge 3110 and edges 3112A, 3112B. In at least one embodiment, the top surface 3104 is substantially non-breaking and centrally located on the bridge 3101. In one or more embodiments, the transition region 3106 and top surface 3104 are substantially smooth. According to one embodiment, the construction of the top surface 3104 (along with other features, such as curved leg transitions described herein) result in concentration of stress throughout the bridge 3101, instead of, as in previous approaches, at the connections between the staple bridge and the staple legs. In at least one embodiment, the concentration and distribution of strain throughout the bridge 3101 moves stress concentrations from the outer legs 2307A, 2307B and inner legs 2309A, 2309B to the bridge 3101, thereby reducing strain at connections therebetween and reducing a risk of leg deformation or breakage.

FIG. 34 shows a bottom view of the staple 3100. In one or more embodiments, the bridge 3101 includes a bottom surface 3402 that is substantially smooth. In one or more embodiments, the depth 3207 of the bridge 3101 is greater than the depth 3209 of the outer legs 2307A, 2307B and inner legs 2309A, 2309B. Accordingly, in various embodiments, the outer shoulders 3201A, 3201B and inner shoulders 3203A, 3203B transition from the depth 3207 to the depth 3209 in a direction from the bridge 3101 towards the distal ends 2311A, 2311B and distal ends 2313A, 2313B. In at least one embodiment, the outer shoulders 3201A, 3201B and inner shoulders 3203A, 3203B include a slope, arch, or other transition from each edge 3114A, 31314B, or 3110 of the bridge 3101 to the corresponding proximal end 3105A, 3105B (FIG. 31) or proximal end 3205A, 3205B (FIG. 32) of the outer legs 2307A, 2307B and inner legs 2309A, 2309B.

According to one embodiment, the transition from the depth 3207 to the depth 3209 is substantially gradual and constant (e.g., a gradual slope or a constant radius arch). In one or more embodiments, the slope includes more than one slope of varying pitch or multiple arches of varying transition radii 3503 (FIG. 35).

In at least one embodiment, the bridge 3101 includes a central portion 3404 between radial points 3213A, 3213B. According to one embodiment, the central portion 3404 includes a length 3406 that measures about 6-20 mm, about 6-8 mm, about 8-10 mm, about 9 mm, about 10-12 mm, about 12-14 mm, about 13 mm, about 14-16 mm, about 16-18 mm, or about 18-20 mm. In various embodiments, the central portion 3404 includes a substantially continuous cross-section.

FIG. 35 shows a side view of the staple 3100. In various embodiments, the bridge 3101 is smooth and with a low-profile geometry that enables more curvature of the bridge 3101, which may create greater sustained compression when the staple 3100 is inserted into tissue.

In various embodiments, each outer leg 2307A, 2307B (not shown) is connected to a bottom portion of bridge 3101 at the corresponding proximal end 3105A, 3105B of the outer legs 2307A, 2307B (e.g., proximal end 3105A connects to outer leg 2307A, etc.). In at least one embodiment, the staple 3100 includes transitional regions 3501A (and 3501B, not shown) that transition the end 3103A and the end 3103B (not shown) to side surfaces 3505A and 3505B (not shown) of the outer legs 2307. According to one embodiment, the transitional regions 3501A, 3501B are sloped or curved according to one or more radii described herein.

As described herein, in one or more embodiments, the edge 3110 transitions the top surface 3104 to the transition region 3106, and the edges 3112A, 3112B transition the transition region 3106 to the side surfaces 3117A, 3117B. In at least one embodiment, the transition region 3106 includes a first slope towards the edge 3110 and includes a second slope, greater than the first slope, towards the edges 3112A, 3112B.

In at least one embodiment, a radius 3503 forms a curvature of the outer shoulders 3201A, 3201B and inner shoulders 3203A, 3203B (not shown in FIG. 35). According to one embodiment, the radius 3503 transitions the side surfaces 3117A, 3117B to the outer shoulders 3201A, 3201B and inner shoulders 3203A, 3203B. According to one embodiment, the radius 3503 transfers the transition region 3106 to the transitional regions 3501A, 3501B (e.g., 3501B located on the outer leg 2307B, not shown). In one or more embodiments, the radius 3503 measures about 0.25-1.0 mm, about 0.25-0.5 mm, about 0.5 mm, about 0.5-0.75 mm, or about 0.75-1.0 mm.

In one or more embodiments, a radius 3505 forms a second curvature of the outer shoulders 3201A, 3201B and inner shoulders 3203A, 3203B. According to one embodiment, the radius 3505 transitions the outer shoulders 3201A, 3201B and inner shoulders 3203A, 3203B to the outer legs 2307A, 2307B and inner legs 2309A, 2309B. In one or more embodiments, the radius 3505 measures about 0.25-2.0 mm, about 0.25-0.5 mm, about 0.5-0.75 mm, about 0.75-1.0 mm, about 1.0 mm, about 1.0-1.25 mm, about 1.25-1.5 mm, about 1.5-1.75 mm, or about 1.75-2.0 mm.

According to one embodiment, the radius 3503 and radius 3505 transition the transition region 3106, the outer shoulders 3201A, 3201B (shown as 3201 in FIG. 35) and the inner shoulders 3203A, 3203B (not shown in FIG. 35) from the depth 3207 (FIG. 32) to the depth 3209 (FIG. 32).

Figure 36:
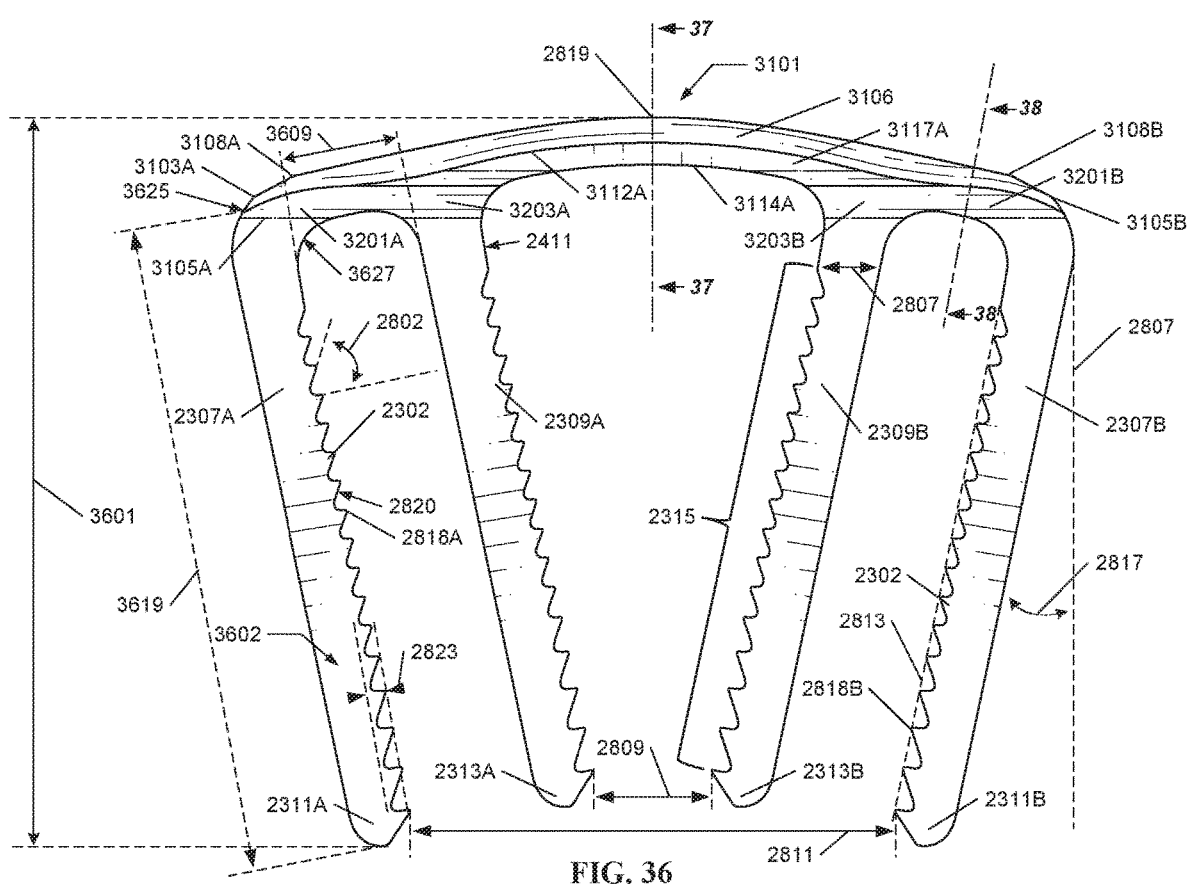
FIG. 36 is a front view of an exemplary low profile staple, according to one embodiment of the present disclosure.

FIG. 36 shows a front view of the staple 3100. In one or more embodiments, the staple 3100 includes a height 3601. According to one embodiment, the height 3601 measures about 22.0-25.0 mm, about 22.0-22.5 mm, about 22.5-23.0 mm, about 23.32 mm, about 23.0-23.5 mm, about 23.51 mm, about 23.5-24.0 mm, about 24.0-24.5 mm, or about 24.5-25.0 mm.

In one or more embodiments, the outer legs 2307A, 2307B and inner legs 2309A, 2309B include the length 3619 as measured, for example, from the proximal end 3105A of the outer leg 2307A to the bottom thereof or from a proximal end 3906 of the inner leg 2309A to the bottom thereof. In the embodiment shown, the outer legs 2307A, 2307B and inner legs 2309A, 2309B are the same length 3619. In various embodiments, the outer legs 2307A, 2307B and inner legs 2309A, 2309B have different lengths 3619, depending on the application of the staple 3100. In one example, the outer legs 2307A, 2307B are of a first length 3619 and the inner legs 2309A, 2309B are of a second length 3619 measuring less than the first length 3619. According to one embodiment, the length 3619 measures about 15.0-23.0 mm, about 15.0-16.0 mm, about 16.0-17.0 mm, about 17.0-18.0 mm, about 18.0-19.0 mm, about 19.6 mm, about 19.0-20.0 mm, about 20.0-21.0 mm, about 21.0-22.0 mm, or about 22.0-23.0 mm.

In one or more embodiments, the staple 3100 includes an outer radius 3625 defining an external curvature between the transition region 3106 of the bridge 2301 and outer legs 2307A, 2307B. In at least one embodiment, the outer radius 3625 defines a curvature of the transitional regions 3501 (see FIGS. 31, 32, 35). According to one embodiment, the outer radius 3625 measures about 1.0-4.0 mm, about 1.0-1.5 mm, about 1.5-2.0 mm, about 2.0-2.5 mm, about 2.5 mm, about 2.5-3.0 mm, about 3.0-3.5 mm, or about 3.5-4.0 mm. In various embodiments, the staple 3100 includes an inner radius 3627 defining an internal curvature between the bottom surface 3402 (FIG. 34) of the bridge 3101 and outer legs 2307A, 2307B and inner legs 2309A, 2309B. In at least one embodiment, the inner radius 3627 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm.

Figures 37, 38:
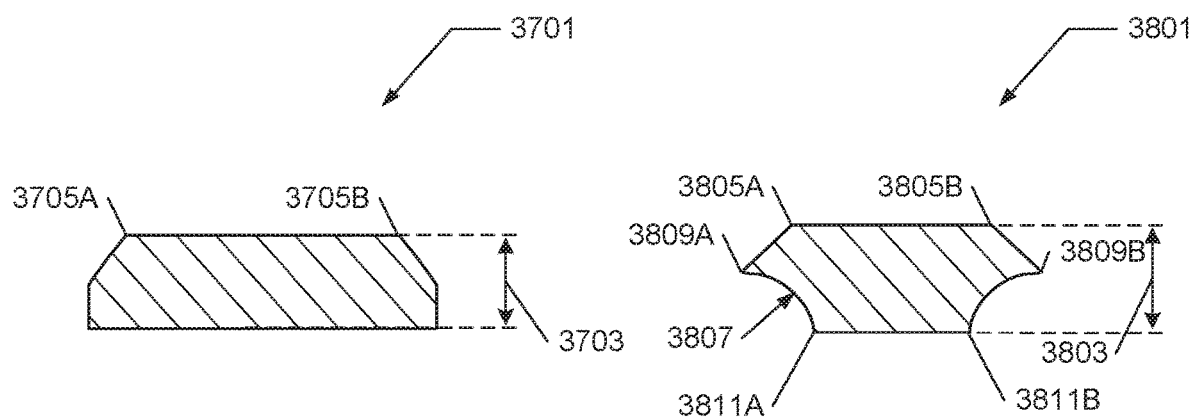
FIG. 37 is a cross-sectional view of an exemplary low profile staple, according to one embodiment of the present disclosure.
FIG. 38 is a cross-sectional view of an exemplary low profile staple, according to one embodiment of the present disclosure.
Figure 39:
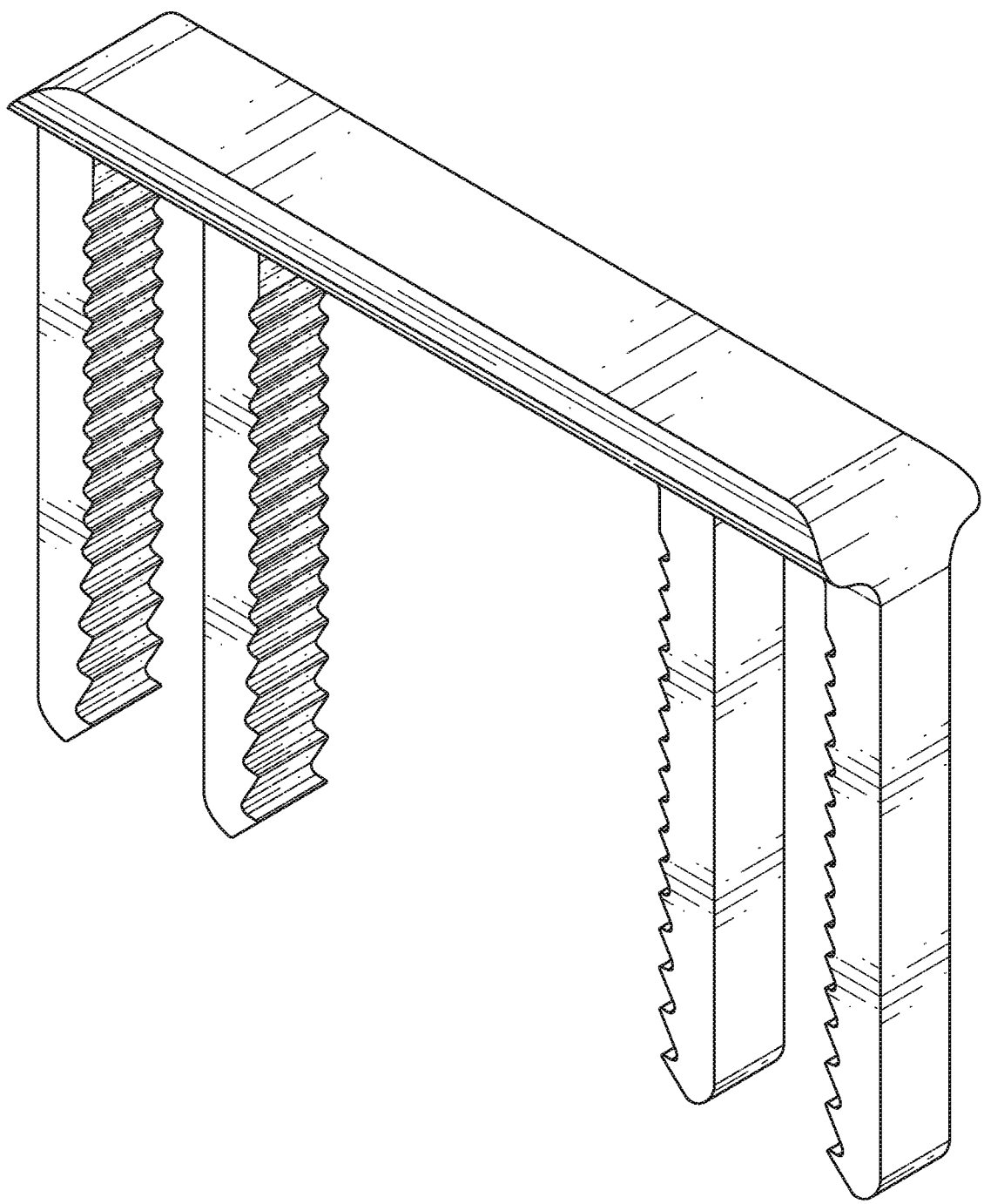
FIG. 39 is a perspective view of an exemplary low profile staple in a second position, according to one embodiment of the present disclosure.
Figure 40:
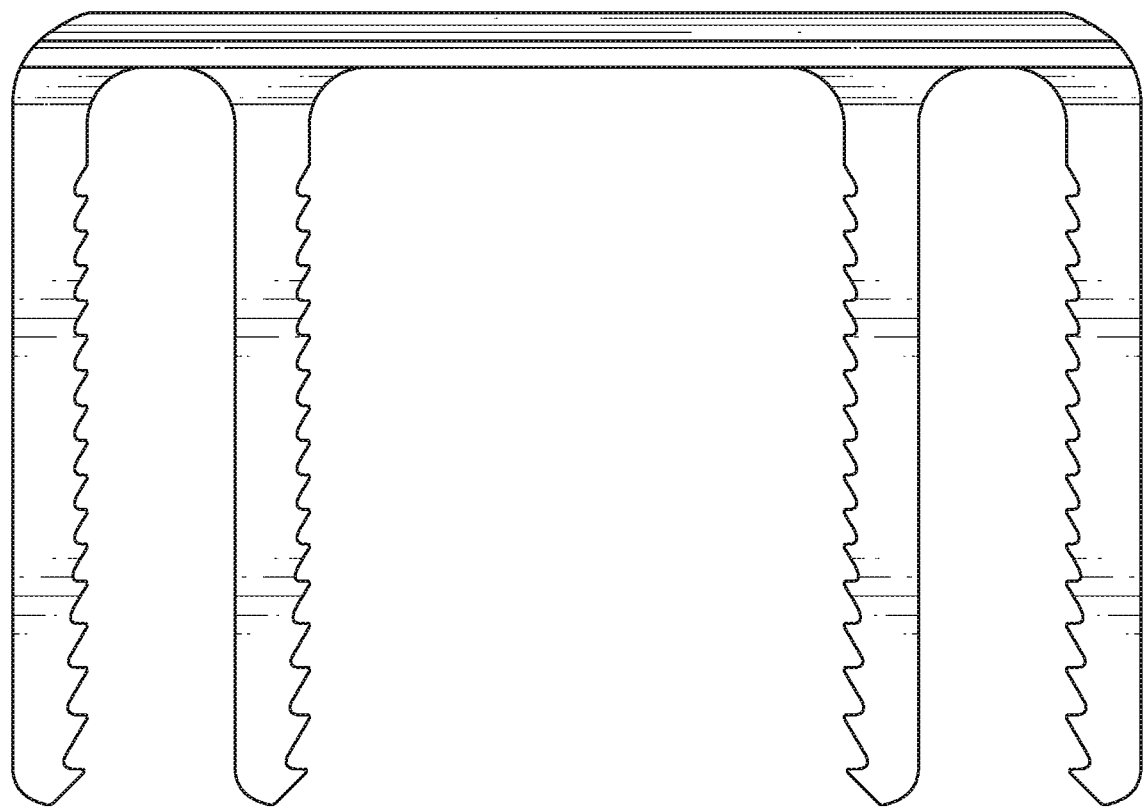
FIG. 40 is a front view of an exemplary low profile staple in a second position, according to one embodiment of the present disclosure.
Figure 41:
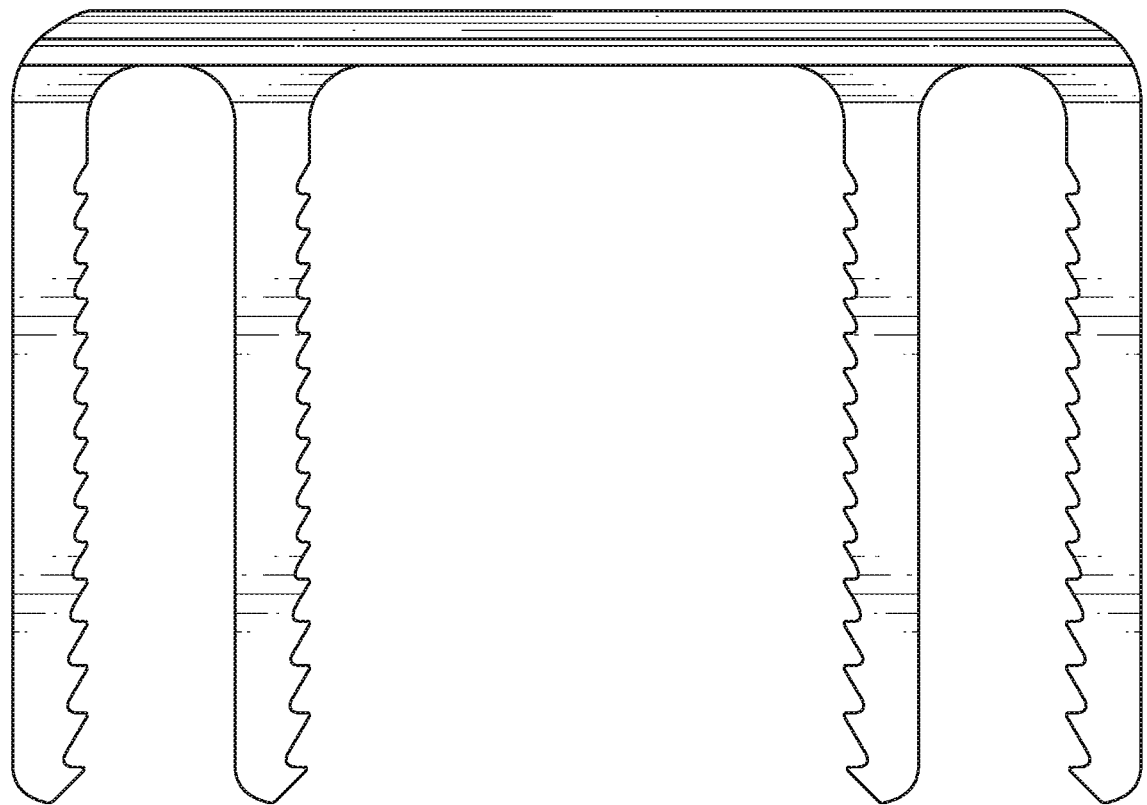
FIG. 41 is a back view of an exemplary low profile staple in a second position, according to one embodiment of the present disclosure.
Figure 42:
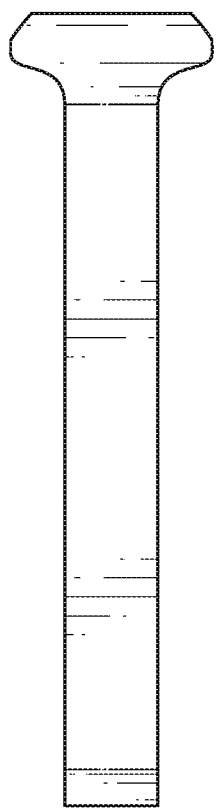
FIG. 42 is a side view of an exemplary low profile staple in a second position, according to one embodiment of the present disclosure.
Figure 43:
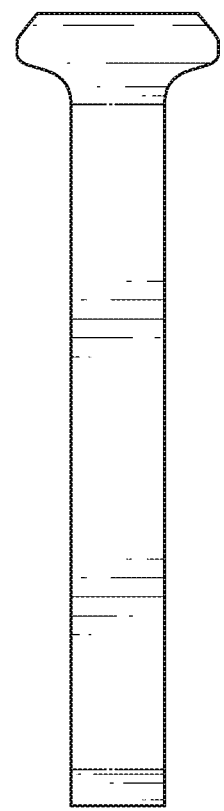
FIG. 43 is a side view of an exemplary low profile staple in a second position, according to one embodiment of the present disclosure.
Figure 44:
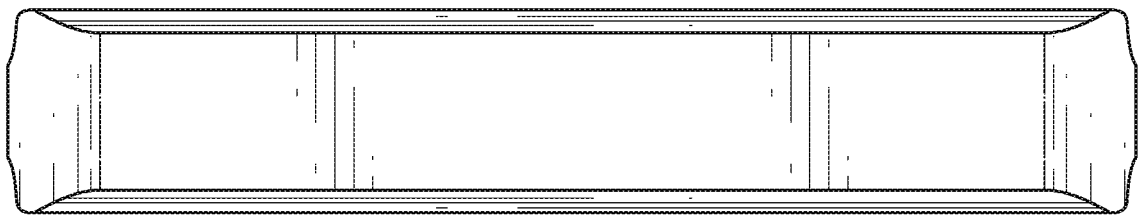
FIG. 44 is a top view of an exemplary low profile staple in a second position, according to one embodiment of the present disclosure.
Figure 45:
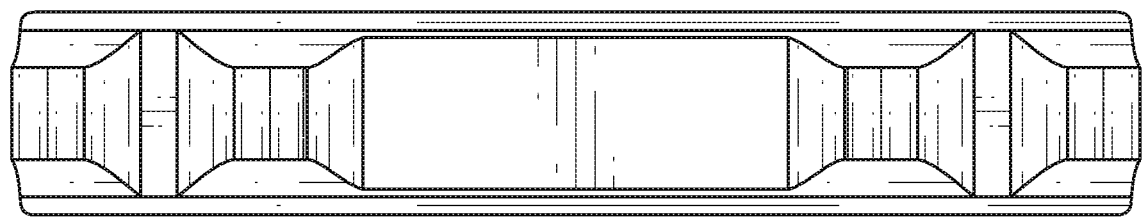
FIG. 45 is a bottom view of an exemplary low profile staple in a second position, according to one embodiment of the present disclosure.
Figure 46:
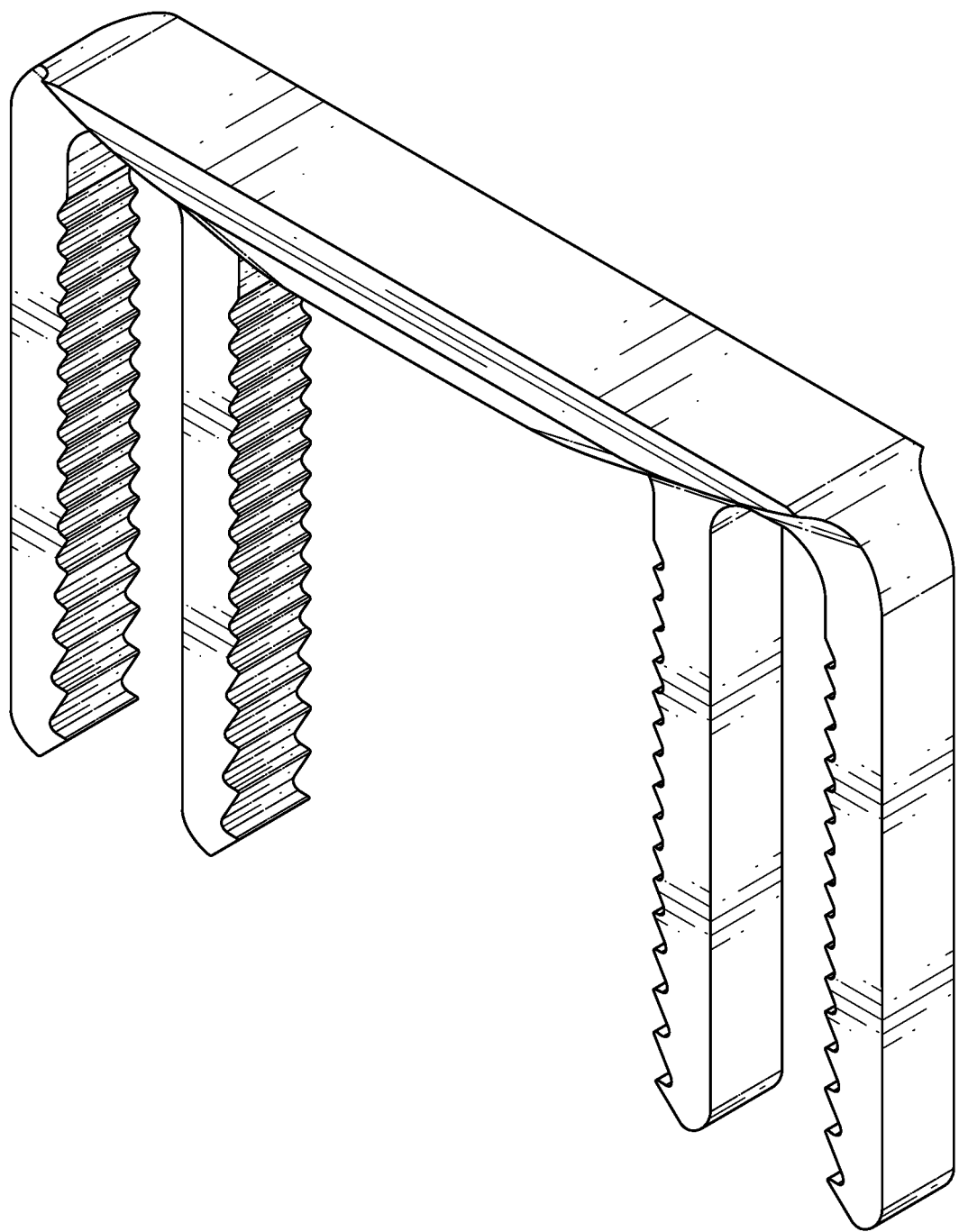
FIG. 46 is a perspective view of an exemplary low profile staple in a second position, according to one embodiment of the present disclosure.
Figure 47:
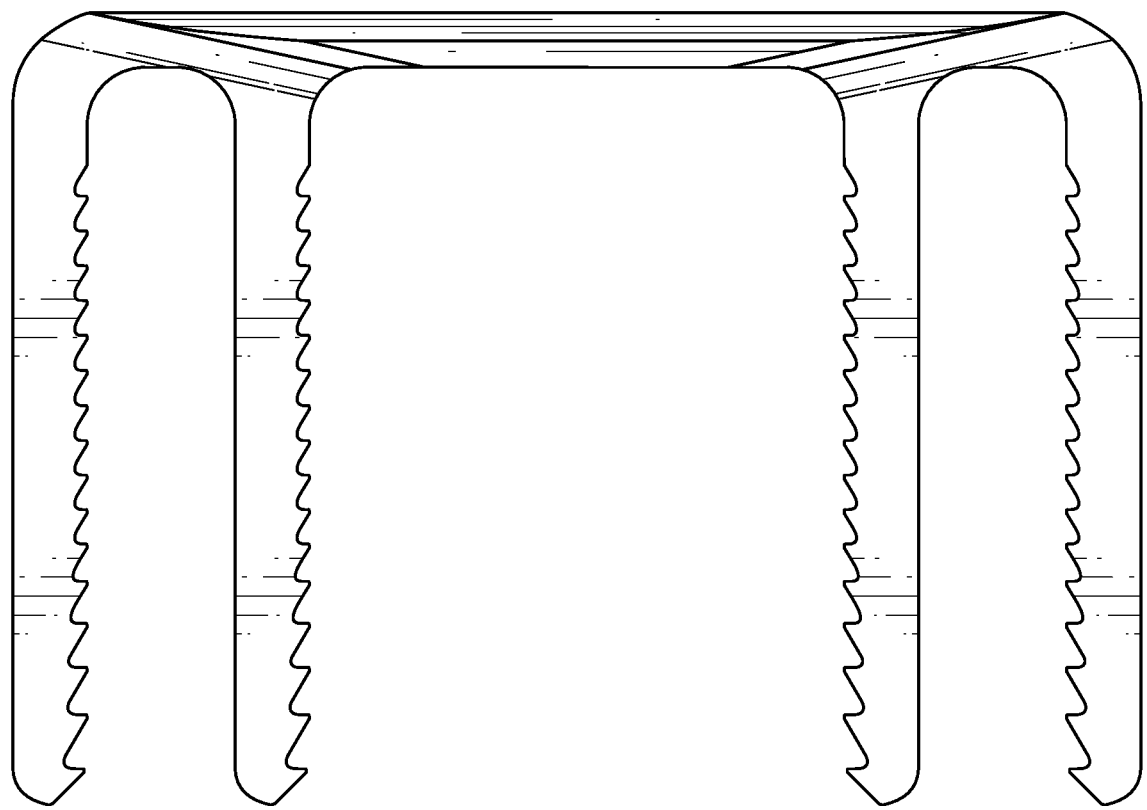
FIG. 47 is a front view of an exemplary low profile staple in a second position, according to one embodiment of the present disclosure.
Figure 48:
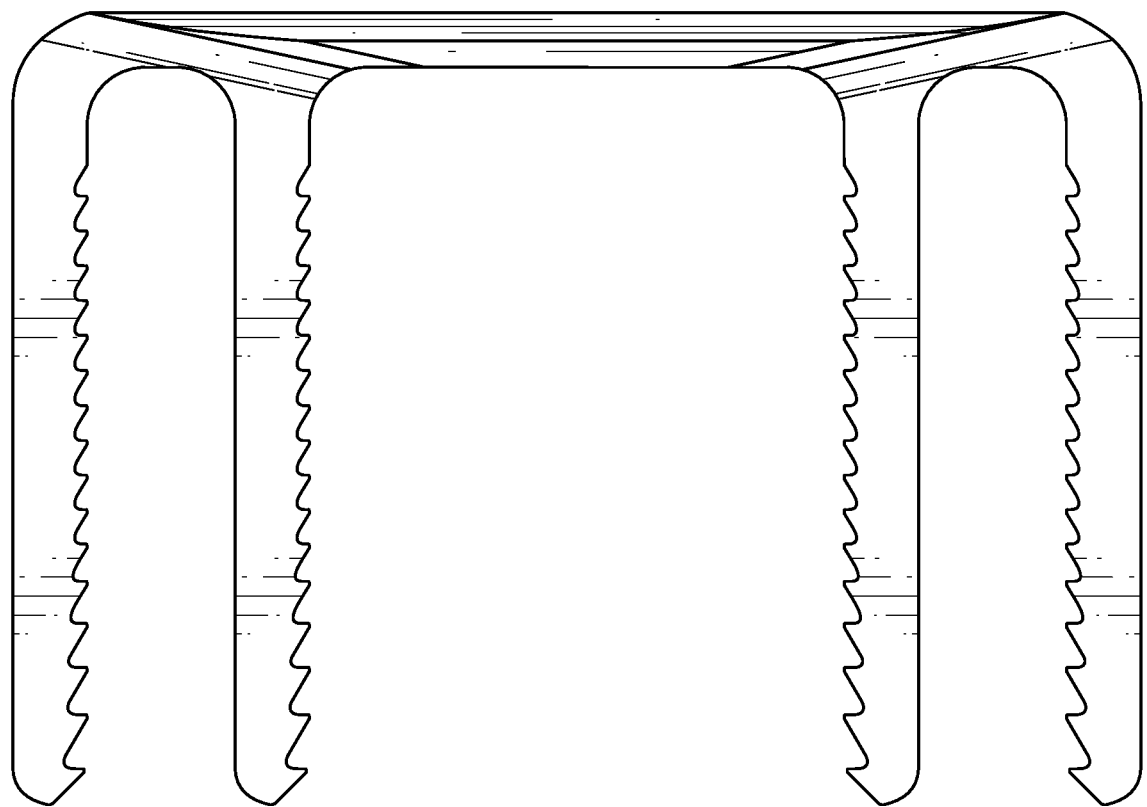
FIG. 48 is a back view of an exemplary low profile staple in a second position, according to one embodiment of the present disclosure.
Figure 49:
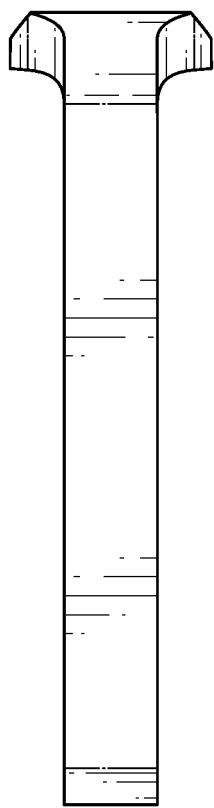
FIG. 49 is a side view of an exemplary low profile staple in a second position, according to one embodiment of the present disclosure.
Figure 50:
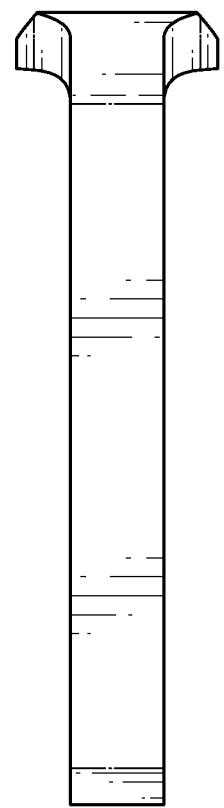
FIG. 50 is a side view of an exemplary low profile staple in a second position, according to one embodiment of the present disclosure.
Figure 51:
FIG. 51 is a top view of an exemplary low profile staple in a second position, according to one embodiment of the present disclosure.
Figure 52:
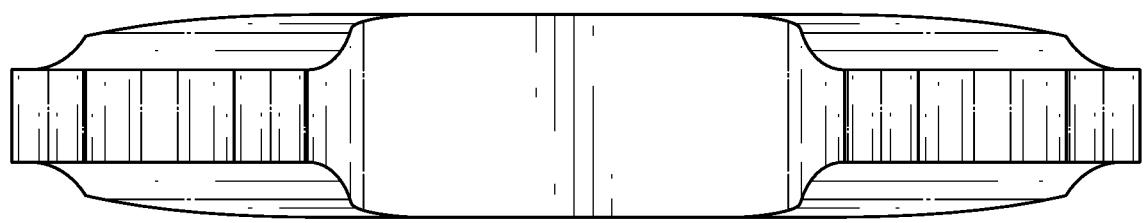
FIG. 52 is a bottom view of an exemplary low profile staple in a second position, according to one embodiment of the present disclosure.

FIG. 36 shows a section line, 37, which indicates a cross-section 3701 of the bridge 3101 shown in FIG. 37.

FIG. 36 shows a section line, 38, which indicates a cross-section 3601 of the bridge 3101 shown in FIG. 38. As shown, the section line 37 passes through an approximate midpoint of the bridge 3101 and the section line 38 passes through an approximate midpoint on the bridge 3101 between the inner leg 2309B and the outer leg 2307B.

FIG. 37 shows a cross-sectional view of the bridge 3101 (FIG. 31). According to one embodiment, the cross-section 3701 shown in FIG. 37 is a cross-section taken from a midpoint of the bridge 3101 as indicated in section line 37 of FIG. 36. In at least one embodiment, the cross-section 3701 is representative of a continuous cross-section of a central portion of the bridge 3101 (e.g., central portion 3404 shown in FIG. 34). In various embodiments, the cross-section 3701 includes a height 3703 representative of a total height of the bridge 3101. According to one embodiment, the height 3703 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm.

According to one embodiment, the bridge 3101 demonstrates a substantially constant moment of inertia (e.g., regardless of a deformation state of the staple 3100) that is located at a central region of the bridge 3101. In at least one embodiment, at least partially due to the substantially constant moment of inertia, the staple 3100 demonstrates substantially constant mechanical properties, such as bending properties, regardless of a current deformation state. According to one embodiment, the substantially constant mechanical properties provide for relatively equal distribution and continuous concentration of stresses at an inner section of the bridge 3101 between the inner legs 2309A, 2309B. In various embodiments, the cross-section 3701 includes corners 3705A, 3705B. In at least one embodiment, the corners 3705A, 3705B are rounded. In alternate embodiments, the corners 3705A, 3705B are angular.

FIG. 38 shows a cross-sectional view of the bridge 3101 (FIG. 31). According to one embodiment, the cross-section 3801 shown in FIG. 38 is a cross-section taken from a midpoint of the bridge 3101 as indicated in section line 38 of FIG. 36.

In various embodiments, the cross-section 3801 includes a height 3803 representative of a total height of the bridge 3101, and is substantially identical to the height 3703. According to one embodiment, the height 3803 measures about 0.5-3.0 mm, about 0.5-1.0 mm, about 1.0-1.5 mm, about 1.5 mm, about 1.5-2.0 mm, about 2.0-2.5 mm, or about 2.5-3.0 mm. In various embodiments, the cross-section 3801 includes corners 3805A, 3805B. In one or more embodiments, the corners 3805A, 3805B are rounded. In alternate embodiments, the corners 3805A, 3805B are angular.

According to one embodiment, the cross-section 3801 includes a radius 3807 defining a curve between corners 3809A and 3811A and between corners 3809B and 3811B. In at least one embodiment, the radius 3807 defines a radius of curvature of outer shoulders 3201A, 3201B and inner shoulders 3203A, 3203B (FIG. 32). In various embodiments, the radius 3807 measures about 0.5-3.0 mm, about 0.5-1.0 mm, about 1.0-1.5 mm, about 1.0 mm, about 1.5-2.0 mm, about 2.0-2.5 mm, or about 2.5-3.0 mm.

FIGS. 39-52 show views of exemplary low profile staples described herein.

According to one embodiment, FIGS. 39-52 show views of exemplary low profile staples in a second position, as described herein.

Exemplary Manufacturing Methods

The exemplary staples described herein may be manufactured in any suitable way. In at least one embodiment, a staple (e.g., staple 100, staple 2300, staple 3100, and other staples discussed herein) is produced from a solid piece of metal via a combination of wire electrical discharge machining (EDM) and grinding. In these embodiments (and others), the staple is a substantially uniform piece of material with each component or portion integrally connected.

Description of Alternative Embodiments

In at least one embodiment, teeth of the staples (e.g., staples 100, 2300, or 3100) described herein are formed out of an inner surface of a staple leg such that ends thereof are not coplanar to the inner surface of the leg. In various embodiments, one or more teeth of teeth sections described herein project outward from an integrally formed inner surface, as opposed to being formed (e.g., "cut") into the inner surface. According to one embodiment, teeth with ends that are coplanar with a leg inner surface are referred to herein as "coplanar teeth," and teeth with ends that are superior to a plane defined by a leg inner surface are referred to herein as "non-coplanar teeth." In one or more embodiments, a staple leg described herein may include: 1) a set of coplanar teeth formed into a first portion of an inner surface of the staple leg; and 2) a set of non-coplanar teeth formed out of a second portion of the inner surface of the staple leg. In at least one embodiment, the staples described herein include coplanar teeth on one or more inner legs, and include the non-coplanar teeth on one or more outer legs. As will be understood by one of ordinary skill in the art, the teeth sections, inner legs, or outer legs may include only coplanar teeth or only non-coplanar teeth, or combinations thereof.

In one example, a staple includes two or more legs, each of the two or more legs including non-coplanar teeth integrally formed into inner surfaces thereof. In a second example, a staple includes two or more legs, each of the two or more legs including: 1) non-coplanar teeth integrally formed along a first portion of inner surfaces thereof; and 2) coplanar teeth integrally formed into a second portion of the inner surfaces. In a third example, a staple includes a first leg and a second leg, the first leg including coplanar teeth and the second leg including non-coplanar teeth.

According to one embodiment, a bridge described herein may include a first depth between the ends thereof and include a second depth, measuring less than the first depth, in portions of the bridge that extend past the ends. In at least one embodiment, the extending portions of the bridge allow the staple to be deformed without applying forces to a portion of the bottom bridge surface between the ends. In one or more embodiments, the extending portions of the bridge reduce a likelihood of deforming forces causing deformation or breakage of transitional structures located therein, such as shoulders.

While various aspects have been described in the context of a preferred embodiment, additional aspects, features, and methodologies of the claimed medical devices and methods for making and using the same will be readily discernible from the description herein, by those of ordinary skill in the art. Many embodiments and adaptations of the disclosure and claimed medical devices and methods other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed medical devices and methods. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed medical devices and methods. In addition, some steps may be carried out simultaneously, contemporaneously, or in synchronization with other steps.

The embodiments were chosen and described in order to explain the principles of the claimed medical devices and methods and their practical application so as to enable others skilled in the art to utilize the medical devices and methods and various embodiments and with various modifications as are suited to the particular use contemplated. Alternative embodiments will become apparent to those skilled in the art to which the claimed medical devices and methods pertain without departing from their spirit and scope. Accordingly, the scope of the claimed medical devices and methods is defined by the appended claims rather than the foregoing description and the exemplary embodiments described therein.

What is claimed is:

1. A staple comprising:
a first leg connected to a bridge at a first shoulder; and
a second leg connected to the bridge at a second shoulder, wherein:
 the bridge comprises a central bridge portion between a radial point of the first shoulder and a radial point of the second shoulder, the central bridge portion comprising:
  a continuous cross-section comprising a continuously curved top edge;
  a first edge and a second edge; and
  a constant width that is greater than a thickness of the central bridge portion and a non-breaking surface between the first edge and the second edge.

2. The staple of claim 1, wherein one or more of the first leg and the second leg comprises a proximal end and a distal end and each distal end includes a wedge-shaped tip.

3. The staple of claim 2, wherein:
one or more of the first leg and the second leg comprises an inner surface and a plurality of teeth;
each of the plurality of teeth are cut out of a respective leg such that a point of each tooth lies in a plane; and
the inner surface of the respective leg lies in the plane.

4. The staple of claim 3, wherein:
a length of the central bridge portion is at least 9 mm; and
a radius of the non-breaking surface of the bridge is at least 8 mm.

5. The staple of claim 4, wherein the length of the central bridge portion is at least 13 mm.

6. The staple of claim 5, wherein the constant width of the central bridge portion is approximately 3.0-7.5 mm.

7. The staple of claim 6, wherein the thickness of the central bridge portion is approximately 0.5-2.9 mm.

8. The staple of claim 7, wherein the first leg forms an angle of greater than approximately 16 degrees with the second leg in a relaxed position.

9. The staple of claim 8, wherein the first leg is parallel with the second leg in a stressed position.

10. The staple of claim 9, wherein strain is distributed evenly throughout the bridge in the stressed position.

11. The staple of claim 10, wherein the staple comprises two legs.

12. The staple of claim 11, wherein the staple comprises more than two legs.

13. The staple of claim 12, wherein the staple comprises four legs.

14. The staple of claim 13, wherein the staple comprises more than four legs.

15. The staple of claim 1, wherein:
the continuously curved top edge comprises a first end opposite a second end; and
the continuous cross-section comprises:
 a first side edge; and
 a second side edge opposite the first side edge, wherein:
  the continuously curved top edge transitions to a) the first side edge at the first end, and b) to the second side edge at the second end; and
  the first side edge and the second side edge are orthogonal to a bottom edge of the continuous cross-section.

16. A method of using a surgical staple, the method comprising:
deforming a nitinol staple from a first position to a second position for inserting the nitinol staple into tissue of a patient, wherein:
 the nitinol staple comprises:
  a bridge comprising a central bridge portion between a radial point of a first inner shoulder and a radial point of a second inner shoulder, the central bridge portion comprising:
   a continuous cross-section;
   a first edge and a second edge; and
   a constant width that is greater than a thickness of the central bridge portion and a non-breaking surface between the first edge and the second edge;
  two or more inner legs integrally formed with the bridge, wherein a first inner leg of the two or more inner legs connects to the bridge at the first inner shoulder and a second inner leg of the two or more legs connects to the bridge at the second inner shoulder; and
  two or more outer legs integrally formed with the bridge;
 in the first position, each of the two or more inner legs forms an angle of greater than approximately 16 degrees with at least one other leg of the two or more inner legs;
 in the second position, each of the two or more inner legs are parallel with the at least one other leg of the two or more inner legs and strain is distributed evenly throughout the bridge; and
 the nitinol staple, when inserted into the tissue of the patient, exerts compressive force on the tissue of the patient.

17. The method of claim 16, wherein:
one or more of the two or more inner legs comprises an inner surface and a plurality of teeth;
each of the plurality of teeth are cut out of a respective leg such that a point of each tooth lies in a plane; and
the inner surface of the respective leg lies in the plane.

18. The method of claim 17, wherein:
a length of the central bridge portion is at least 9 mm; and
a radius of the non-breaking surface of the bridge is at least 8 mm.

19. The method of claim 18, wherein the nitinol staple comprises four legs.

20. The method of claim 15, wherein the bridge comprises two outer shoulders and each of the two or more outer legs connect to the bridge at one of the two outer shoulders.

* * * * *